(12) United States Patent
Ding et al.

(10) Patent No.: US 10,034,929 B2
(45) Date of Patent: Jul. 31, 2018

(54) RNA INTERFERENCE FUNCTIONS AS AN ANTIVIRAL IMMUNITY IN MAMMALS

(71) Applicant: THE REGENTS OF THE UNIVERSITY OF CALIFORNIA, Oakland, CA (US)

(72) Inventors: Shou-Wei Ding, Riverside, CA (US); Yang Li, Shanghai (CN)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/775,938

(22) PCT Filed: Mar. 17, 2014

(86) PCT No.: PCT/US2014/030830
§ 371 (c)(1),
(2) Date: Sep. 14, 2015

(87) PCT Pub. No.: WO2014/145968
PCT Pub. Date: Sep. 18, 2014

(65) Prior Publication Data
US 2017/0028051 A1 Feb. 2, 2017

Related U.S. Application Data

(60) Provisional application No. 61/800,536, filed on Mar. 15, 2013.

(51) Int. Cl.
*C07H 21/02* (2006.01)
*C07H 21/04* (2006.01)
*A61K 48/00* (2006.01)
*A61K 39/12* (2006.01)
*C12N 15/113* (2010.01)
*C12N 7/00* (2006.01)
*A61K 39/00* (2006.01)

(52) U.S. Cl.
CPC ............... *A61K 39/12* (2013.01); *C12N 7/00* (2013.01); *C12N 15/1131* (2013.01); *A61K 2039/5254* (2013.01); *A61K 2039/57* (2013.01); *C12N 2310/14* (2013.01); *C12N 2760/14122* (2013.01); *C12N 2760/14162* (2013.01); *C12N 2770/30022* (2013.01); *C12N 2770/30034* (2013.01); *C12N 2770/30062* (2013.01); *C12N 2770/32222* (2013.01); *C12N 2770/32262* (2013.01)

(58) Field of Classification Search
CPC .. C12N 15/113; C12N 2310/11; C12N 15/67; A61K 31/713
See application file for complete search history.

(56) References Cited

U.S. PATENT DOCUMENTS

| | | | |
|---|---|---|---|
| 7,211,378 B2 * | 5/2007 | Kawaoka | C07K 14/005 424/204.1 |
| 2005/0260166 A1 | 11/2005 | Prins et al. | |
| 2006/0094055 A1 | 5/2006 | Ding et al. | |
| 2012/0045471 A1 | 2/2012 | Haller et al. | |

OTHER PUBLICATIONS

Korber et al. (Biochemistry, 2009, 48 (11), 2307-2309).*
Copenheaver, Blaine R., International Search Report and Written Opinion, PCT/US2014/030830, dated Sep. 8, 2014.
Shimura et al., "A strategy for screening an inhibitor of viral silencing suppressors, which attenuates symptom development of plant viruses", FEBS Letters, Nov. 7, 2008, vol. 582, pp. 4047-4052.
Wittmann-Regis, Agnes, International Preliminary Report on Patentability and Written Opinion, PCT/US2014/030830, dated Sep. 24, 2015.

\* cited by examiner

*Primary Examiner* — Amy H Bowman
(74) *Attorney, Agent, or Firm* — Kilpatrick Townsend & Stockton LLP

(57) ABSTRACT

The disclosure provides recombinant viral vectors and attenuated viruses and viral vaccines comprising a virus lacking a functional viral RNA suppressor of host RNAi.

11 Claims, 46 Drawing Sheets

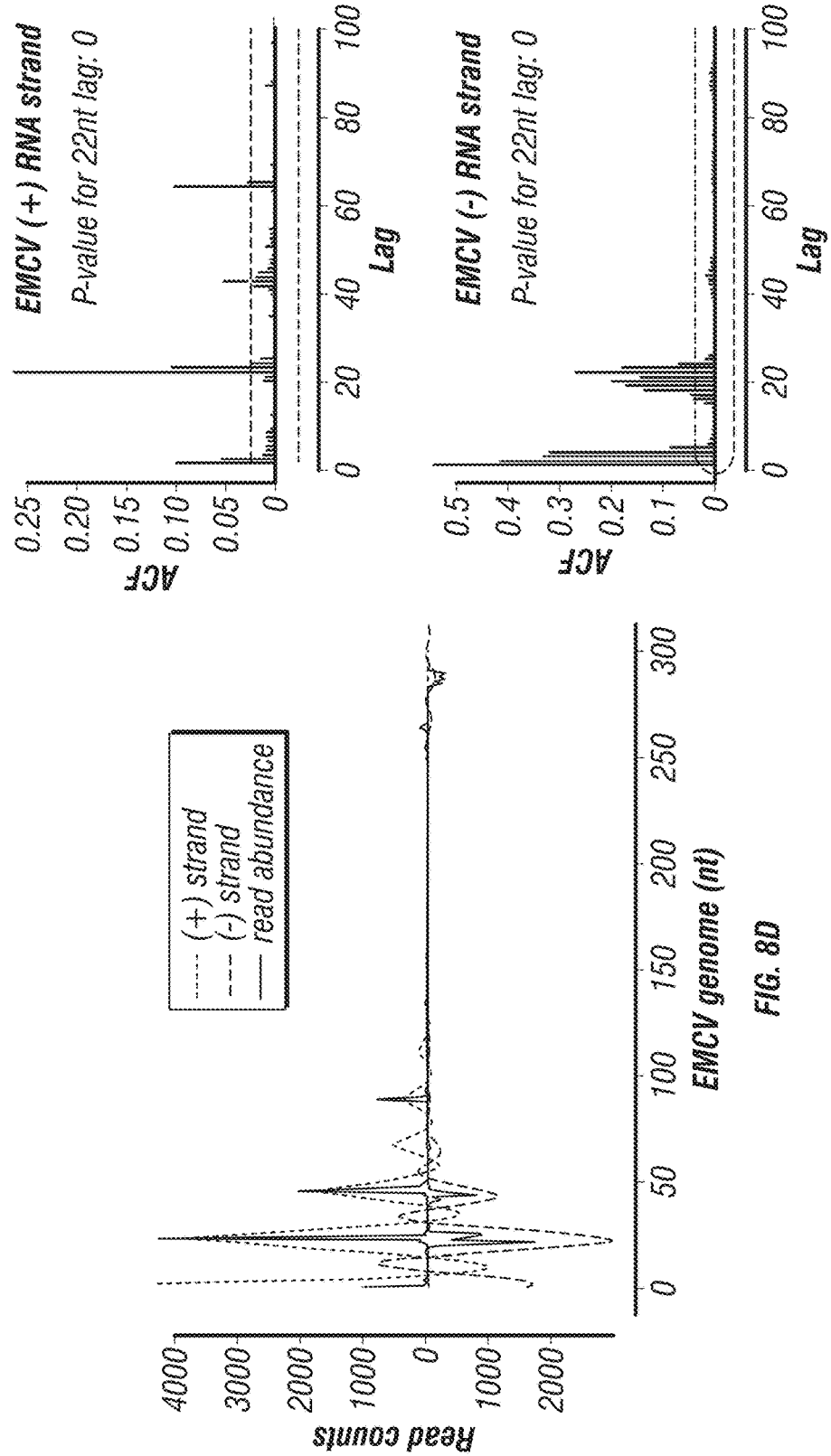

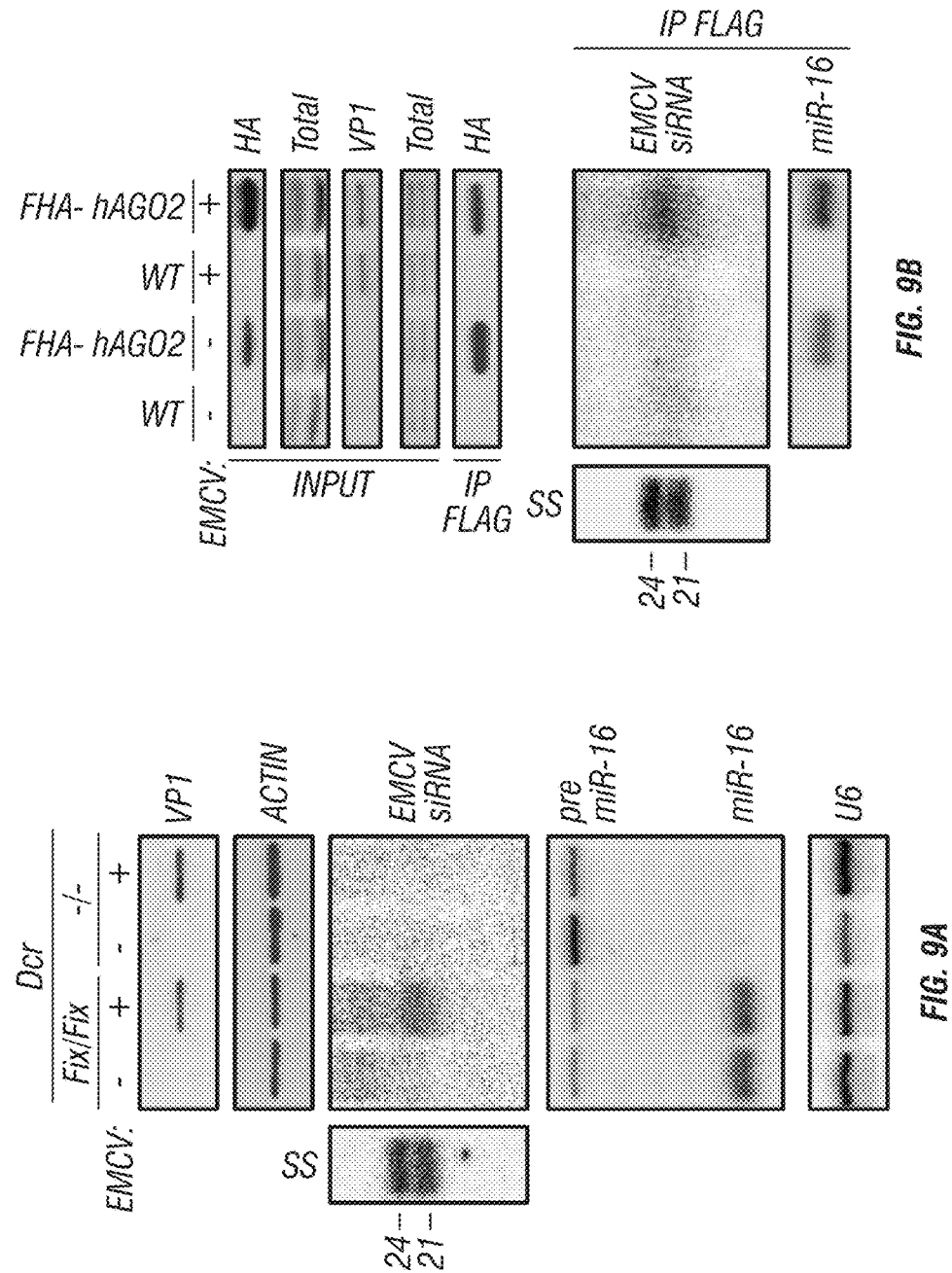

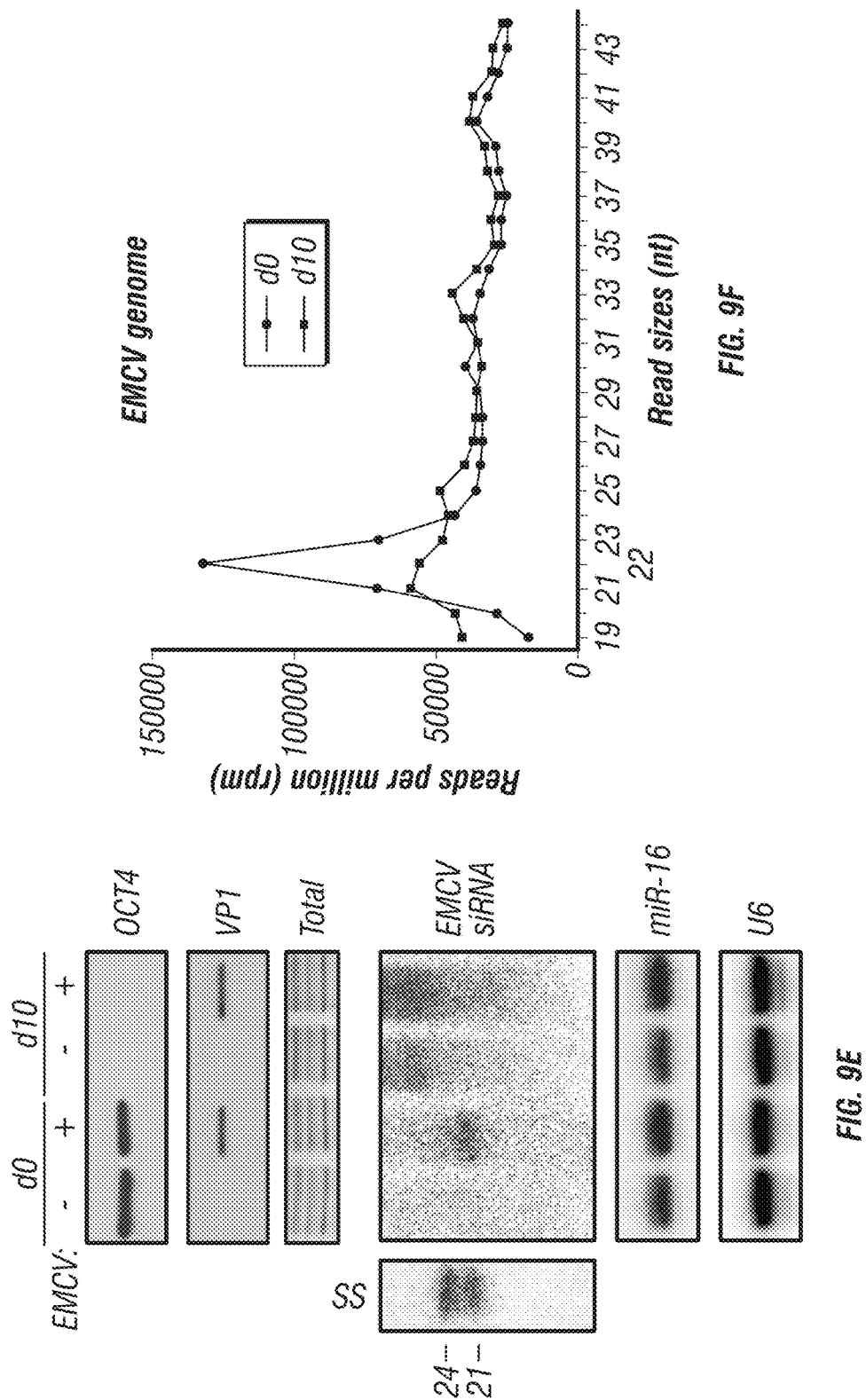

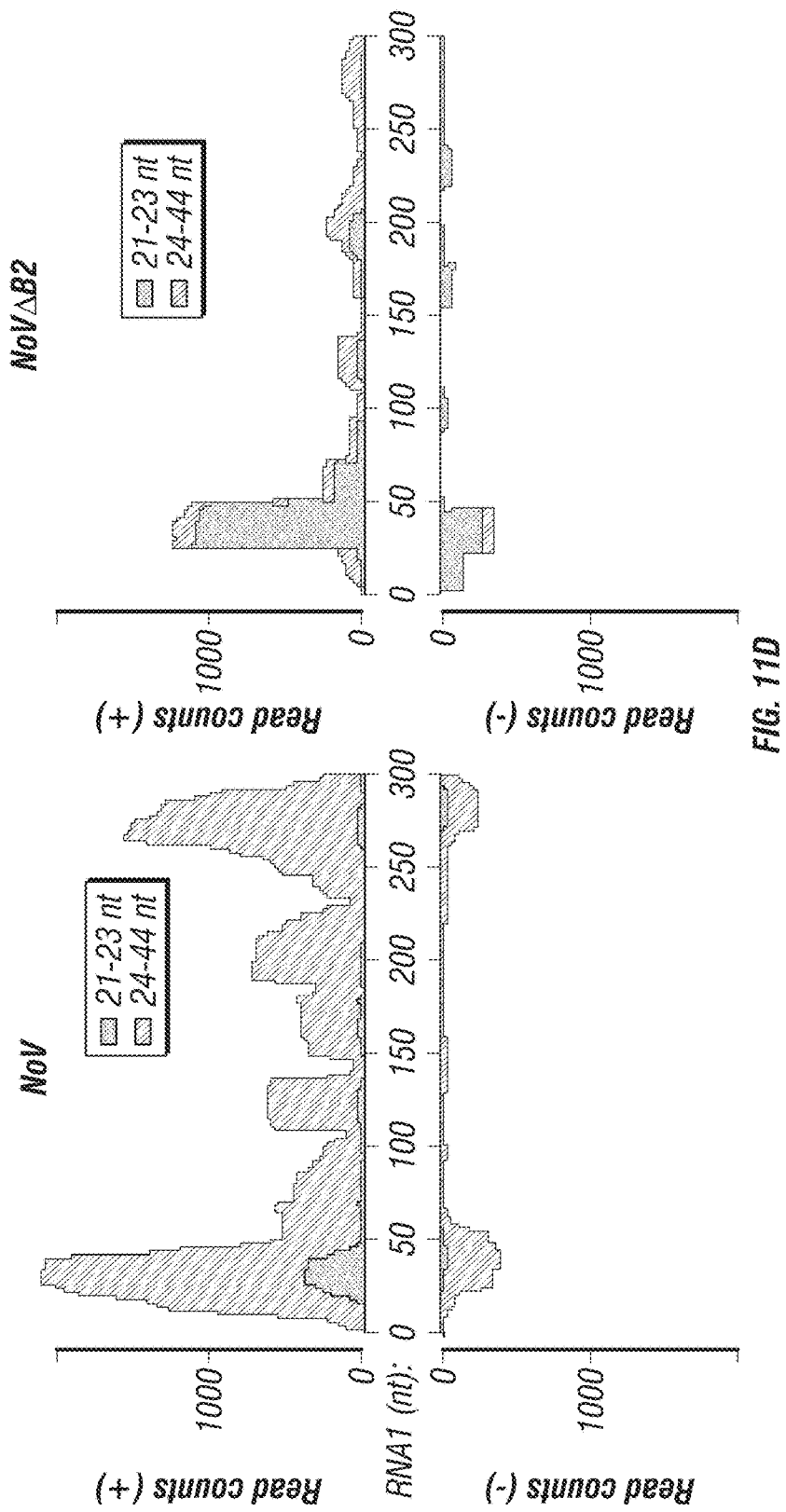

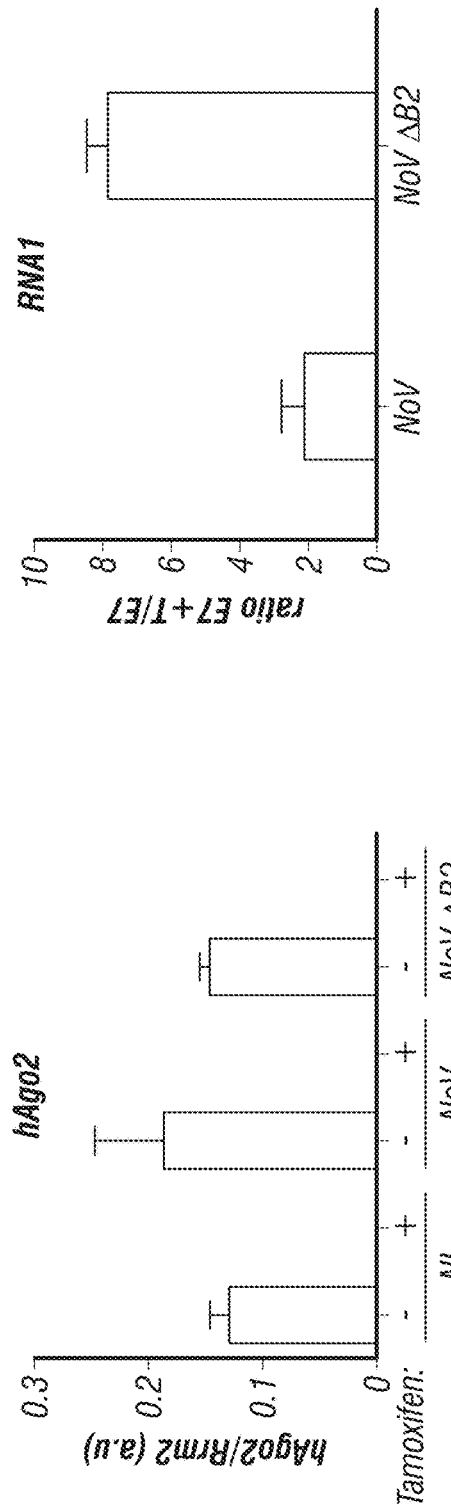
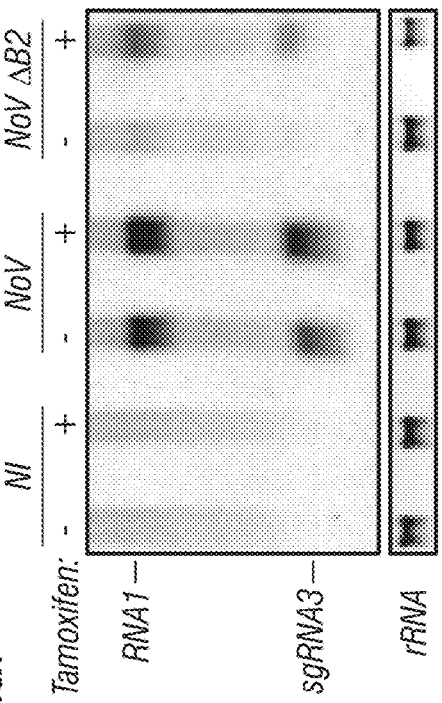
FIG. 13A
FIG. 13B
FIG. 13C

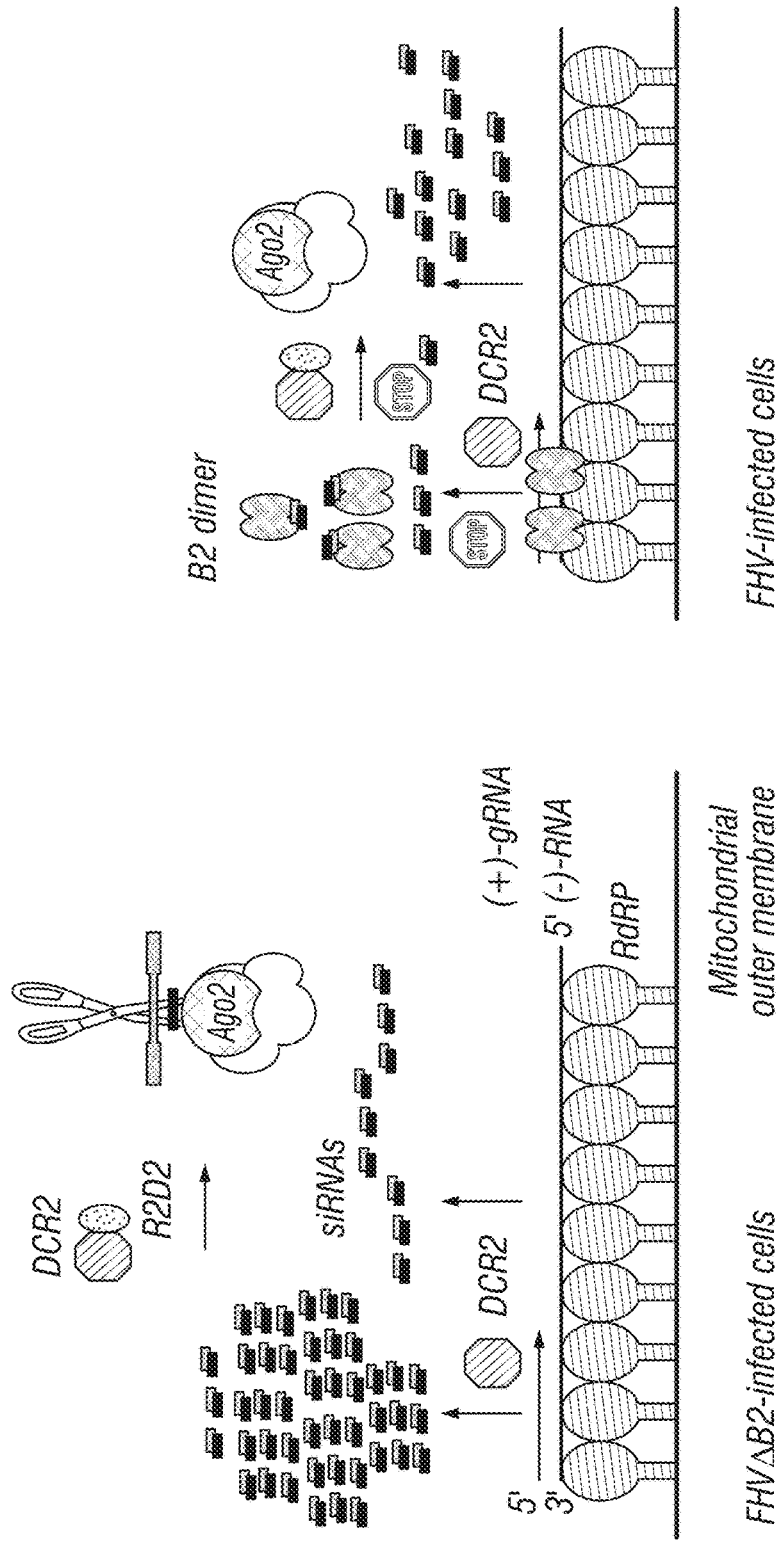

RNA INTERFERENCE FUNCTIONS AS AN ANTIVIRAL IMMUNITY IN MAMMALS

CROSS REFERENCE TO RELATED APPLICATIONS

This application is a U.S. National Stage Application filed under 35 U.S.C. § 371 and claims priority to International Application No. PCT/US2014/030830, filed Mar. 17, 2014, which application claims priority under 35 U.S.C. § 119 from Provisional Application Ser. No. 61/800,536, filed Mar. 15, 2013, the disclosures of which are incorporated herein by reference.

GOVERNMENT LICENSE RIGHTS

This invention was made with Government support under Grant No. AI052447, awarded by the National Institutes of Health. The Government has certain rights in the invention.

TECHNICAL FIELD

The disclosure provides for vaccines and methods to treat or prevent a viral infection or reduce viral load.

BACKGROUND

RNA interference (RNAi) acts as a natural antiviral defense in plants, insects, nematodes, and fungi; accordingly, virulent infection in these organisms requires suppression of antiviral RNAi by a virus-encoded suppressor of RNAi (VSR). It remains unknown whether a virus infection triggers production of canonical viral siRNAs in mammals or if mammalian virus infections require specific suppression of an antiviral RNAi response.

SUMMARY

RNA viruses such as West Nile, Dengue and influenza viruses are among the important and emerging human pathogens and exhibit distinct genetic and immune properties as compared to viruses and cellular pathogens using DNA as the genetic material. The disclosure provides that infection in both mammalian cell culture and mice with a mosquito-transmissible positive-strand RNA virus triggers strong antiviral RNAi response, which must be suppressed by the virus before productive and/or virulent infection is established. The disclosure further provides that induction of the mammalian antiviral RNAi response is accompanied with production of the canonical Dicer-dependent virus-derived siRNAs. These findings provide direct evidence that RNAi acts as a natural antiviral defense in mammals. Thus, the disclosure demonstrates in the first instance, a new RNA-based antiviral immunity in mammals where host cell death is not necessary for reducing pathogen burden.

Highly conserved innate immunity mechanisms, such as Toll-like receptor pathway, mediate natural defense against pathogens in the fruit fly and mammals. However, although RNA interference (RNAi) is a conserved mechanism in eukaryotes and functions as an antiviral immunity in fruit flies, nematodes and plants, studies in the last decade have not yet provided conclusive evidence for an antiviral function of RNAi in mammals. The disclosure shows that cultured mammalian cells produce virus-specific, canonical small interfering RNAs (siRNAs) in response to the challenge by a mosquito-transmissible RNA virus, Nodamura virus (NoV), which is known to encode a viral suppressor of RNAi (VSR). The disclosure further demonstrate that the VSR-deficient NoV mutant induces accumulation of abundant viral siRNAs and becomes non-virulent in suckling mice unlike wild type NoV, which is lethal to suckling mice, indicating that viral suppression of the RNAi response is important for disease induction in mice. Together, the findings reveal a new RNA-based antiviral immunity in mammals.

Furthermore, the disclosure demonstrates that NoV infection of cultured human cells also induces production of virus-derived siRNAs and requires viral suppression of the RNAi response. These findings show for the first time that humans use an immunity mechanism, RNAi, for defense against virus infection and further that virus infection in mammals, including humans, is facilitated by the expression of a virus-encoded protein to suppress the mammal's RNAi response.

The disclosure further demonstrates that up-regulating the RNAi defense will increase immunity against virus infection. Furthermore, the disclosure presents a new class of drug targets to prevent or control a viral infection in humans, the virus-encoded suppressor of RNAi (VSR).

Additionally, viruses which have been made to be VSR-deficient represent a new type of live attenuated virus vaccines. This idea was tested by vaccinating suckling mice with VSR-deficient NoV and challenging them two days later by a lethal dose of wildtype NoV. The immunized mice were fully protected compared to control mice.

In a certain embodiment, the disclosure provides for an attenuated virus that lacks a functional virus-encoded suppressor of RNAi (VSR) of a mammalian subject's RNAi. In a further embodiment, the attenuated virus comprises one or more mutations in the coding sequence for a VSR polypeptide, such as deletions, insertions, substitutions or a combination of any of the foregoing. In another embodiment, the attenuated virus is incapable of inhibiting siRNA biogenesis in a subject. In yet another embodiment, the attenuated virus is selected from Nodamura virus, Ebola virus, HIV-1, HIV-2, measles virus, influenza virus, papillomaviruses, picornaviruses and hepadnaviruses.

In a particular embodiment, the disclosure provides for a vaccine comprising an attenuated virus disclosed herein. In a further embodiment, a vaccinated subject produces canonical siRNAs upon exposure to the vaccine of the disclosure. In a further embodiment, the canonical siRNAs are produced in an Argonaute-dependent manner. In yet a further embodiment, the canonical viral siRNAs produced by administering the vaccine prevent or reduce the likelihood of an infection of a mammalian subject's cells by a virus. Examples of viruses include Nodamura virus, Ebola virus, HIV-1, HIV-2, measles virus, influenza virus, papillomaviruses, picornaviruses and hepadnaviruses.

In a certain embodiment, the disclosure further provides for a VSR inhibiting agent that reduces or inhibits the activity of a viral RNA suppressor of a mammalian subject's RNAi. In a further embodiment, the VSR inhibiting can be used to treat or prevent a viral infection in a mammalian subject. In yet a further embodiment, the VSR inhibiting agent is administered to a subject with a viral infection the production of canonical viral siRNAs by the subject is increased. In another embodiment, by administering a VSR inhibiting agent to a subject with a viral infection, the severity of a viral infection is reduced. In yet another embodiment, the VSR inhibiting agent is an antibody to the viral RNA suppressor of a mammalian subject's RNAi. In an alternate embodiment, the VSR inhibiting agent is a siRNA to the viral RNA suppressor of a mammalian subject's RNAi.

In a certain embodiment, the disclosure provides for a recombinant replication competent viral vector comprising an attenuated virus of the disclosure and a heterologous gene of interest. In a further embodiment, the heterologous gene of interest is an antigen.

The disclosure provides for one or more embodiments set forth in the accompanying drawings and the description below. Other features, objects, and advantages of the invention will be apparent from the description and drawings, and from the claims.

DESCRIPTION OF DRAWINGS

Figures 4A, 4B:
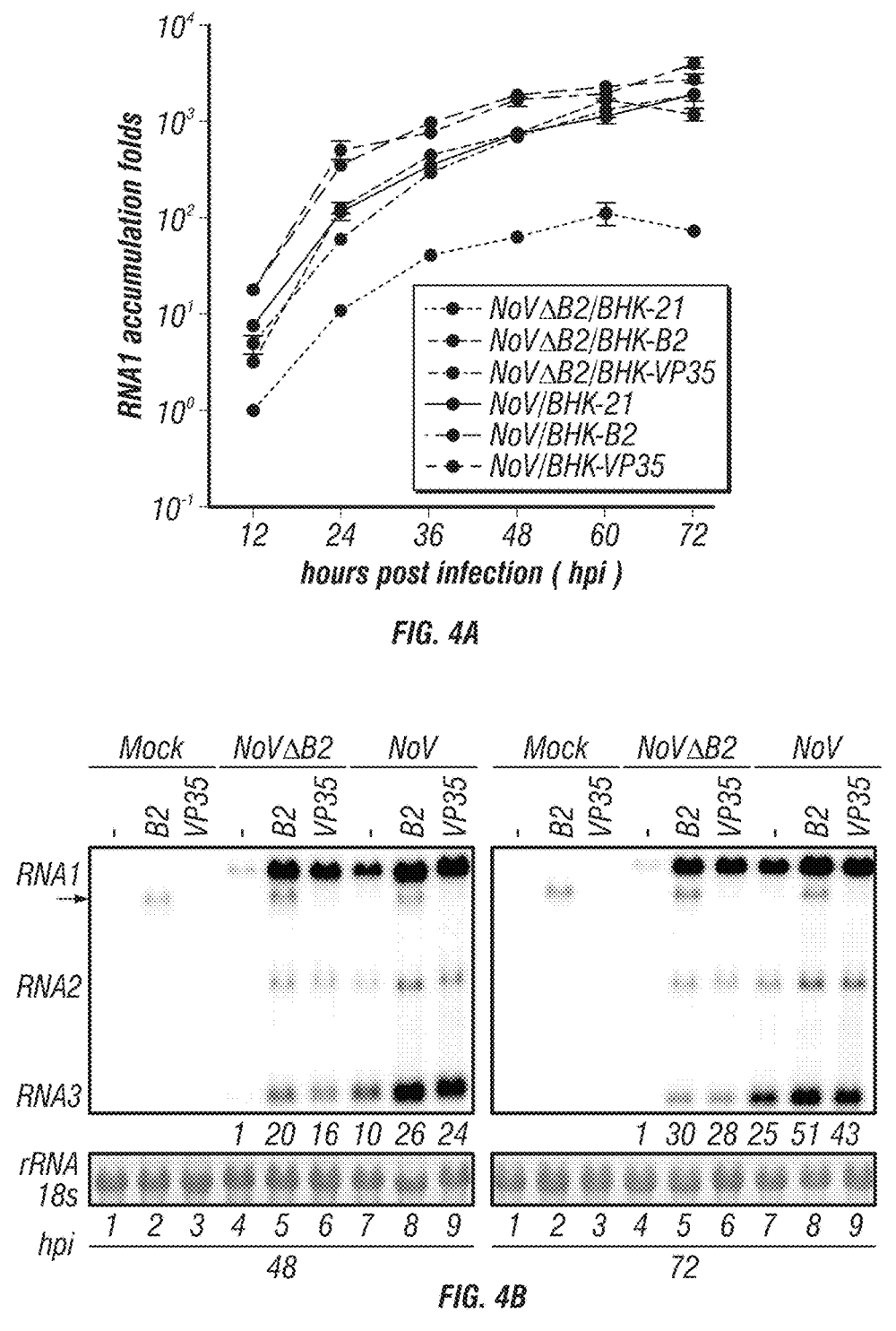

FIG. 4A-B demonstrates that NoV infection requires RNAi suppression. (A) BHK-21 cells (−) or BHK cells stably expressing B2 (B2) or VP35 (VP35) were mocked infected or infected by NoVΔB2 or NoV of the same titer. Every 12 hours post infection (hpi), the viral genomic RNA-1 levels were determined by quantitative RT-PCR with the accumulation level of NoVΔB2 in BHK-21 cells at 12 hpi set as 1. Error bars indicate standard deviation of three replicates. (B) Accumulation of NoV and NoVΔB2 RNAs 1-3 in the infected cells detected by Northern blotting. RNA-1 signal quantified by phosphorimager was shown with that of NoVΔB2 in BHK-21 cells at 48 hpi set as 1. Detection of B2 transgene mRNA (arrow) was visible. 18S rRNA staining served as loading control.

FIG. 8A-E provides for the characterization of mESC lines infected with EMCV. (A) Western analysis of EMCV viral protein 1 (VP1) in various mESC lines (E14, PGK, HM1) in non-infected (−) or at 3 hours or 6 hours post-infection (hpi) with the indicated virus titer determined on BHK-21 cells. TCID50/cell: 50% tissue culture infective dose per cell. (B) Schematic representation of the EMCV genome (top) and quantitative realtime PCR analysis (qRT-PCR) (bottom) of pluripotency factors Oct4, Nanog and EMCV RNA (5' UTR, VP3 and 2A) in mESCs infected (+) or not (−) in ES or Glasgow media. Positions of the 3 pairs of primers used to quantify EMCV RNA by qRT-PCR analysis are indicated with black bars on the EMCV genome map. Results are mean and standard deviations (SD) of two independent experiments. (C) Sequences of reads 21-23-nt along the first 5'-terminal 110-nt of the EMCV RNA (+) and (−) strands. For each sequence the corresponding number of reads (in bold italic) with its position (in nt) along the viral genome and its sequenced variants are indicated. Read sequences not detected by deep sequencing are depicted with each nucleotide symbolized by X and assembled following the apparent phased production of viRNAs with the ~22-nt periodicity. The 2-nt 3' overhangs are represented in red. (D) Model periodic signals reconstructed by a singular spectrum analysis from the 10 top contributors to the total variance extracted from the raw data by a singular spectrum analysis (see methods). The model periodic signals for the 5'-end reads of the EMCV RNA (+) strand and the 3'-end reads for the (−) strand are indicated by red and blue lines, respectively. Corresponding raw count for (+) and (−) strands are indicated with a black line. (E) Auto-correlation plot displaying the periodicity of the 5'-end reads of the EMCV RNA (+) strand and of the 3'-end reads for the (−) strand. Confidence interval of 0.95 is indicated with red dashed lines. ACF: autocorrelation function.

FIG. 9A-G demonstrates that EMCV siRNAs are loaded into AGO2 and are strongly reduced in Dcr$^{-/-}$ mESCs and after differentiation. (A) Western and Northern analysis of VP1 (top), EMCV 5'-end siRNAs (middle) and miR-16 (bottom) in Dcr$^{Flx/Flx}$ and Dcr$^{-/-}$ mESCs infected (+) or not (−) with EMCV. SS siRNAs were used as size-markers as in FIG. 7E. ACTIN and U6: loading controls for proteins and RNA, respectively. (B) Northern analysis of EMCV 5'-end siRNAs at 6 hpi in FLAG-specific immunoprecipitates isolated from WT mESCs or mESCs stably expressing FHA-hAGO2 infected (+) or not (−) with EMCV. SS: as in (A). Western analyses show comparable infection levels and confirm FHA-hAGO2 immunoprecipitation. Total: Coomassie-stained proteins provide a loading control. (C) 21-23-nt read distribution along the EMCV genome upon deep-sequencing of RNA isolated from endogenous AGO2 IP 6 hpi of mESCs. Asterisks indicate the reads analyzed in FIG. 10E. (D) Same as (C), but along the first 5'-terminal 150-nt. (E) Western and Northern analysis of OCT4, EMCV VP1, EMCV 5'-end siRNAs and miR-16 in undifferentiated (d0) or after 10 days-of-differentiation (d10) of mESCs infected (+) or not (−) with EMCV. Total: as in (B); U6, SS: as in (A). (F) Size distribution of vsRNA deep-sequencing reads mapping the EMCV genome in the samples from (E). Read abundance was normalized to the total number of reads mapping the EMCV genome. (G) Read mapping the EMCV genome in infected d0 and d10 mESCs as in FIG. 7D. Note the scale change in read counts, highlighted in red. Inset: the duplex 1-2 is still detectable in d10 cells.

Figure 11F:
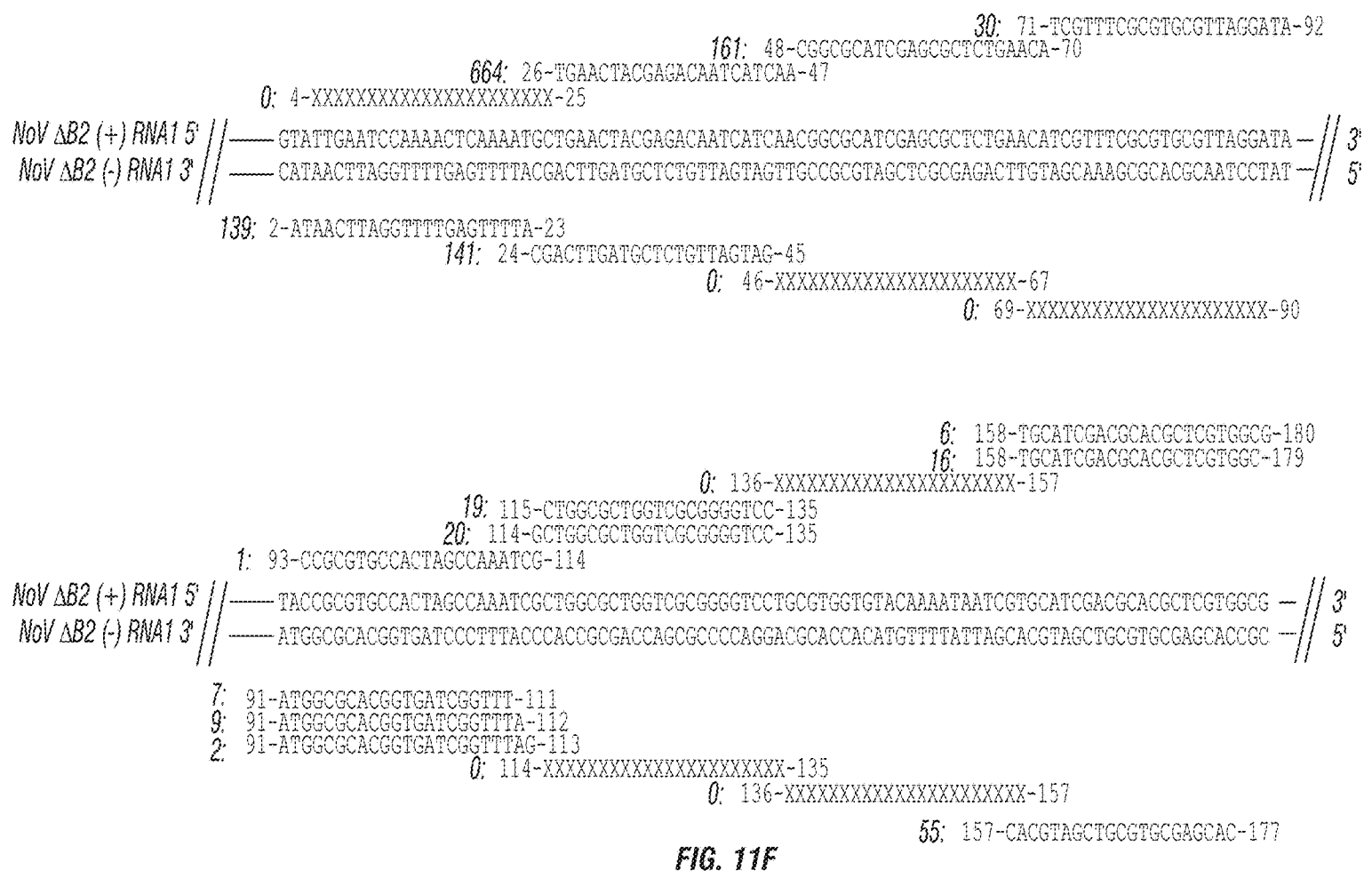

FIG. 11A-F demonstrates that NoV-encoded B2 antagonizes processing of NoV-derived dsRNA. (A) Northern analysis of genomic RNA1 and subgenomic RNA3 72 hpi of mESCs with NoV or NoVΔB2. rRNA: ethidium bromide staining of ribosomal RNA; NI, non-infected; sgRNA3: subgenomic RNA3. (B) Normalized size distribution of deep-sequencing reads mapping the NoV or NoVΔB2 genome in the infected mESCs used in (A). (C) 21-23-nt and 24-44-nt read distributions along the (+) and (−) strands of the NoV (left) and NoVΔB2 (right) RNA1 in infected mESCs. (D) Same as (C), but along the first 5'-terminal 300-nt of NoV (left) or NoVΔB2 (right) RNA1. (E) Radar plots as in FIG. 7D, but for NoV and NoVΔB2; the 5' first nucleotide of RNA1 defines register #1. (F) Sequences of reads along the first 5'-terminal 180-nt of NoVΔB2 RNA1 (+) and (−) strands. The number of each read with its position (in nt) along the viral genome and its sequenced variants are indicated. Read sequences not detected by deep-sequencing are depicted with nucleotides symbolised by 'X' assembled following the phased production of viRNAs within the ~22-nt periodicity. Identical reads detected in both BHK-21 cells and mice infected with NoVΔB2 are depicted in blue. 2-nt 3' overhangs are indicated in red.

Figure 12B:
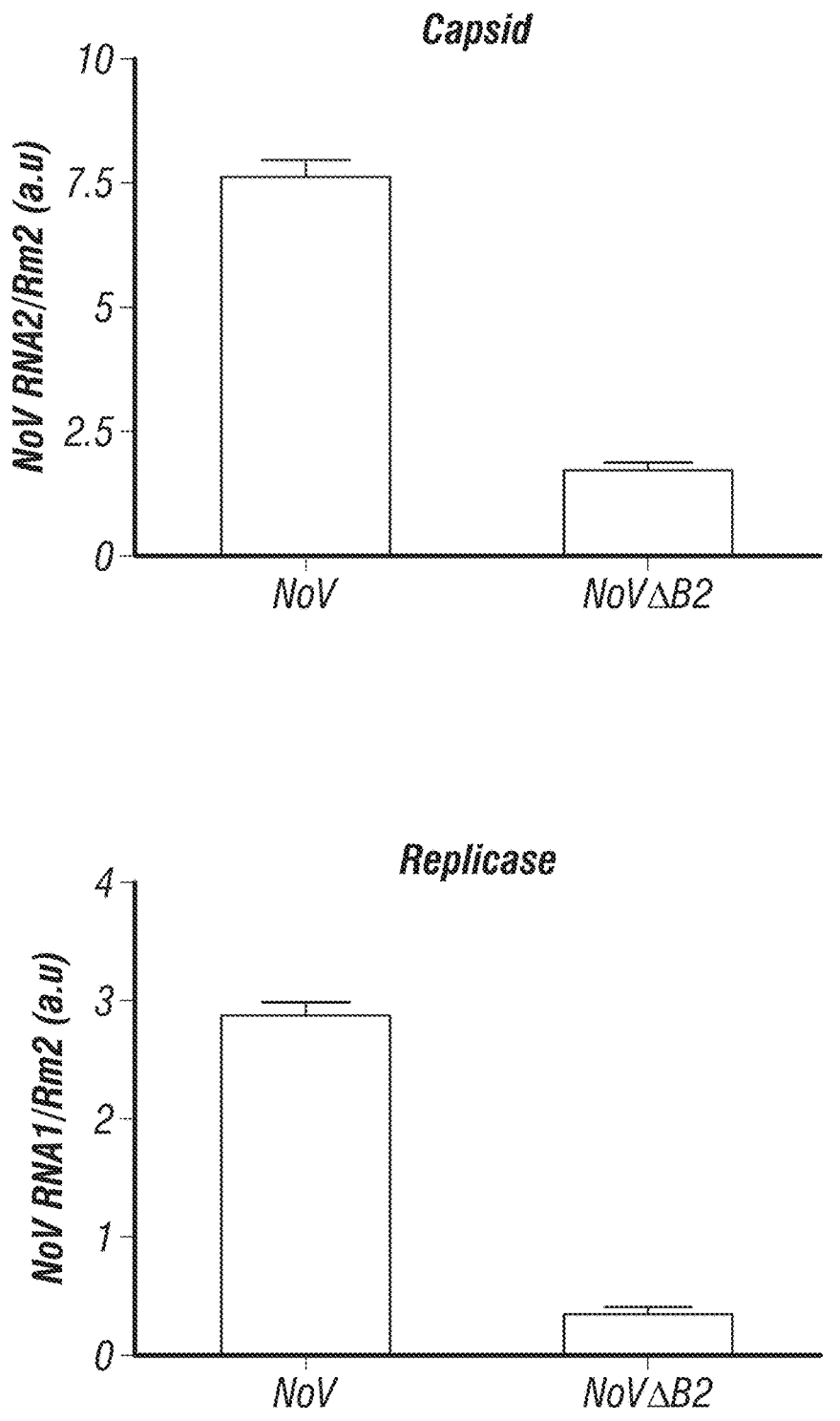

FIG. 12A-E demonstrates the construction of NoVΔB2 by mutating the NoV-derived dsRNA and a characterization of NoVΔB2 activity. (A) Schematic representation of the two NoV genomic (RNA-1 and RNA-2) and single subgenomic RNA (RNA-3, from which the B2 protein is produced). The mutations engineered in RNA-1 to create NoVΔB2 are depicted: U2745C and U2754C disrupt the start codons of both B2 open reading frames (B2-137 and B2-134), while C2757G generates a stop codon. None of these 3 mutations affects the overlapping Protein A/B1 ORF. The absence of B2 production from NoVΔB2 was previously determined. The positions of the oligonucleotide primers used in (B) for qRT-PCR analysis are indicated with black bars. (B) Quantification of Replicase (left) and Capsid (right) by qRT-PCR analysis in mESCs infected with NoV or NoVΔB2. Results are mean and SD of two independent experiments. (C) Same as in main FIG. 11C, but with deep-sequencing reads mapping to the RNA2 of NoV and NoVΔB2. (D) Same as in FIG. 8D, but with deep-sequencing reads mapping to the RNA1 of NoV and NoVΔB2. (E) Same as in FIG. 8E, but with deep-sequencing reads mapping to the RNA-1 of NoV and NoVΔB2.

FIG. 13A-C demonstrates the rescue of NoVΔB2 accumulation in AGO2-deficient mESCs. (A) qRT-PCR analysis of the hAgo2 transgene mRNA levels in non-infected (NI), NoV-infected and NoVΔB2-infected E7 mESC treated (+) or not (−) with tamoxifen for 5 days. Results show the mean and standard deviation (s.d) of two independent experiments. (B) Relative accumulation of NoV or NoVΔB2 RNA1 72 hpi in E7 mESC treated (+T) or not with tamoxifen, assessed by qRT-PCR on samples used in (A). Results show the mean of the ratio and the s.d calculated from two independent experiments. (C) Northern analysis of NoV and NoVΔB2 genomic RNA-1 and subgenomic RNA3 72 hpi of the cells used in (A). rRNA: as in FIG. 11A; sgRNA3: subgenomic RNA-3.

FIG. 14A-B provides a model for the induction and suppression of antiviral RNAi in *Drosophila*. The available data indicate that antiviral RNAi is triggered by the dicing of the dsRNA produced during the initiation of the progeny RNA synthesis from (−)-RNA templates, leading to the high density of the 5'-terminal viral siRNAs as found in FHVΔB2-infected cells (A). In FHV-infected cells (B), the detected interaction of B2 with viral RdRP is predicted to promote B2's access to the nascent viral dsRNA in its suppression of host dicing. The current model also envisions that B2 suppression of dicing at the terminal region allows robust transcriptional initiation of the subgenomic RNA internally from the antigenomic RNA templates, triggering the production of a distinct set of siRNA hot spots to target the downstream RNA3-coding region of RNA1. B2-viral siRNAs complexes are also detectable in FHV-infected cells, suggesting a second VSR activity.

DETAILED DESCRIPTION

Figure 1A:
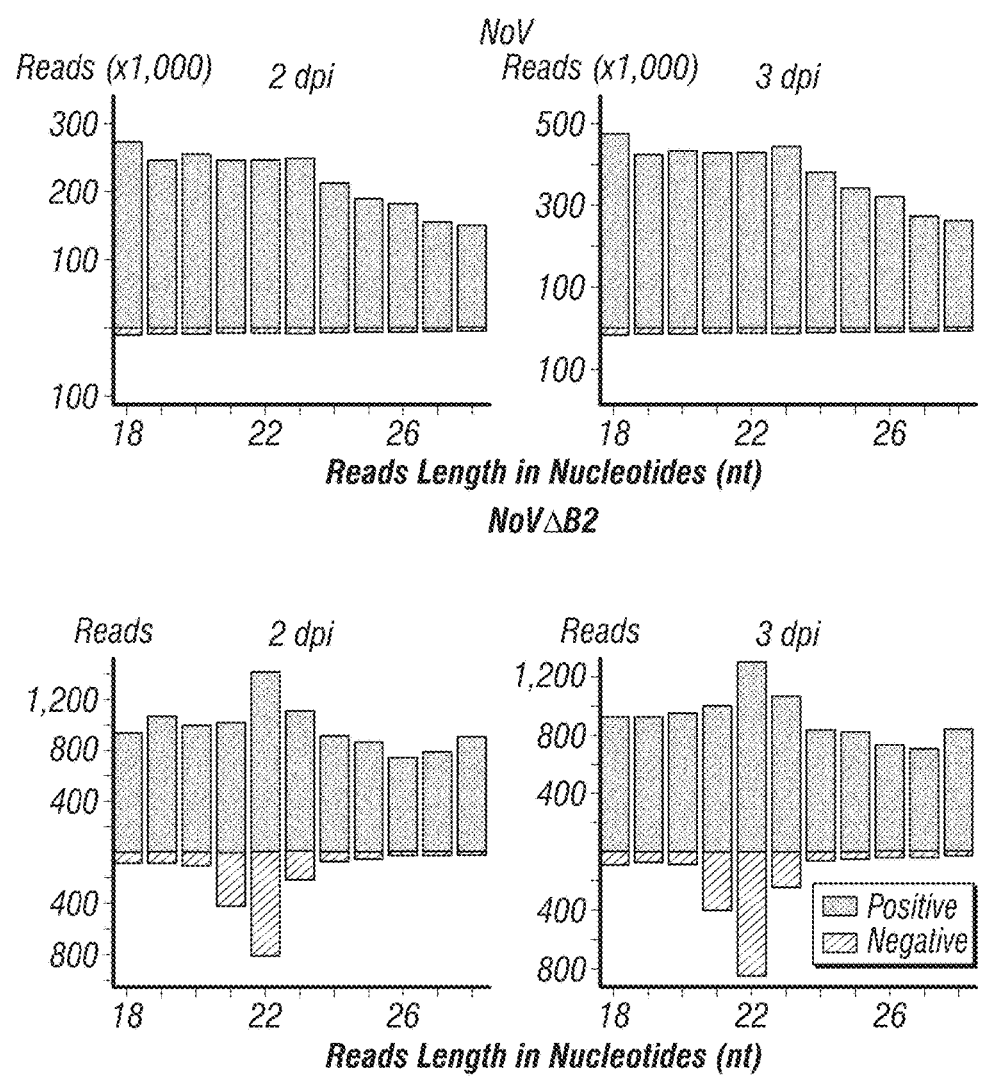
FIG. 1A-B demonstrates the siRNA properties of virus-derived small RNAs (vsRNAs) in BHK-21 cells. (A) Length distribution and abundance of positive- or negative-strand vsRNAs from cells 2 or 3 days post inoculation (dpi) with NoV or NoVΔB2. (B) Total counts of pairs of complementary 22-nt vsRNAs of NoV or NoVΔB2 in each distance category (in nucleotides) between 5' and 3' ends of a complementary vsRNA pair, defined as 0 for perfect base-paired 22-nt vsRNAs with blunt ends, −2 for pairs with 2-nt overhang at the 3'-end of each strand (α and β), or 20 for pairs with 20-nt overhang at the 5'-ends (α and γ).

As used herein and in the appended claims, the singular forms "a," "and," and "the" include plural referents unless the context clearly dictates otherwise. Thus, for example, reference to "a virus" includes a plurality of such viruses and reference to "the cell" includes reference to one or more cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As defined herein, the term "inactivation" refers to the act of reducing or eliminating the expression of a particular gene.

The term "polynucleotide sequence of a virus sufficient to activate RNA silencing" or "polynucleotide sequence of a virus that activates RNA silencing", as used herein, refers to any portion of the viral genome which is capable of inducing degradation of viral or any other target RNA of the virus.

As used herein, the term "recombinant vector" refers to a recombinant DNA construct which has polynucleotide sequences that enable either stable and heritable expression of the construct or transient expression in an host. Typically, such vectors are non-infectious and are introduced into cells via standard methods including, but not limited to calcium phosphate-mediated transfection, lipid-mediated transfection, electroporation, DNA guns, etc.

As used herein, the term "heterologous" refers to any sequence from another organism. For example, the term "polynucleotide sequences from heterologous viruses" as used herein refers to sequences from viruses other than the virus which provides the sequences that activate RNA silencing.

As used herein, the term "endogenous gene" refers to any gene which is a natural part of the genome and has not been introduced via artificial means.

The term "RNA silencing" as used herein refers to the degradation of RNA as a process induced by a natural "trigger", e.g., viral infection, rather than artificial manipulation, which is referred to as RNAi. In this application, the term specifically refers to the antiviral defense mechanism by which viral RNA is degraded in response to viral infection in a plant or animal cell.

The term "RNAi" or "RNA interference" as used herein refers to the degradation of RNA induced by introduction of dsRNA into a cell or manipulations designed to induce cells to produce artificial dsRNA.

The term "RNA silencing suppressor" as used herein refers to any polypeptide which is capable of blocking or reducing RNA silencing.

"Antibody fragments" comprise only a portion of an intact antibody, wherein the portion typically retains at least one, more commonly most or all, of the functions normally associated with that portion when present in an intact antibody. Examples of antibody fragments include Fab, Fab', F(ab')$_2$, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

An "antigen" is a predetermined antigen to which an antibody can selectively bind. The target antigen may be polypeptide, carbohydrate, nucleic acid, lipid, hapten or other naturally occurring or synthetic compound.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the invention.

In both plants and invertebrates, virus infection triggers Dicer processing of virus-specific dsRNA into siRNAs that are essential for specific antiviral defense by RNAi; accordingly, virulent infection requires expression of a virus-encoded suppressor of RNAi (VSR) that interfere with either the biogenesis or the antiviral activity of viral siRNAs. Induction of antiviral RNAi depends on the processing of virus-specific double-stranded RNA (dsRNA) by Dicer nuclease into 21- to 24-nucleotide (nt) small interfering RNAs (siRNAs), which are short dsRNAs with two unpaired nucleotides at the 3' end of either strand. For example, studies on Flock house virus (FHV) infection in *Drosophila* have provided a model (see FIG. 14) for the induction and suppression of antiviral RNAi. FHV is a member in genus *Alphanodavirus* of the Nodaviridae and contains a bipartite positive-strand RNA genome. *Drosophila* encodes two largely independent pathways for the biogenesis and activity of 22-nt miRNAs [Dicer-1(DCR1)/Argonaute-1 (AGO1)] and 21-nt siRNAs (DCR2/AGO2). FHV siRNAs, predominantly 21-nt, are produced by Dicer-2 and loaded into Argobnaute-2 by a heterodimer of DCR2 and the dsRNA-binding protein R2D2 (see FIG. 14). As counter-defense, FHV encodes the dsRNA-binding VSR protein B2, translated from a subgenomic RNA (RNA3) of FHV RNA1, which acts as a homodimer (see FIG. 14) with dual modes of RNAi suppression: it binds long dsRNA and inhibits its dicing into siRNAs, and it also binds duplex siRNA, which is predicted to inhibit loading of viral siRNAs into RISC. Consistently, substitution of the 54$^{th}$ residue of B2, an Arg conserved in the alphanodaviral B2 proteins, to Gln (R54Q) inactivates both dsRNA-binding and RNAi suppressing activities. Notably, although wildtype FHV causes virulent infection in adult flies, the B2-deficient mutant of FHV, FHVΔB2, is rapidly cleared in wildtype flies but induces virulent infection in fly mutants knocked out for Dicer-2, R2D2, or Argonaute-2. These findings illustrate that viral suppression of RNAi is essential for productive infection and that induction of antiviral RNAi is sufficient to terminate virus infection in the absence of viral suppression of RNAi.

Mammals encode a single Dicer for the biogenesis of siRNAs and miRNAs and four Argonautes with highly overlapping activities to load siRNAs and miRNAs. Little is known about the role of RNAi in mammalian virus infections. Mammalian viral mRNAs are as susceptible as cellular mRNAs to RNAi programmed by synthetic siRNAs. Some DNA viruses encode miRNAs to regulate gene expression whereas direct interaction of Hepatitis C virus (HCV) RNA with host miRNA-122 is necessary for replication. Diverse mammalian viral proteins can suppress RNAi in non-vertebrate systems or experimental RNAi in mammalian cells. Recent deep sequencing studies detected accumulation of virus-derived small RNAs (vsRNAs) in mammalian cells infected by RNA viruses. Sequenced HCV vsRNAs, in particular, contain complementary 20-21nt vsR-NAs with 1- or 2-nt 3' overhangs, some of which are found in AGO complexes with an unknown function. However, mammalian vsRNAs reported to date exhibit a near random length distribution pattern unlike the Dicer-dependent viral siRNAs characterized in plants and invertebrates. In absence of a mammalian infection model that produces canonical viral siRNAs, it remains unknown if the conserved RNAi mechanism has an antiviral function in mammals or if mammalian virus infections require VSR activities.

Mammalian viral proteins that can suppress insect and plant RNAi or artificially induced RNAi in mammalian cells have been identified, and the virulence function of one such protein can be complemented by distinct siRNA sequestering plant VSRs. Although mammalian viruses are susceptible to experimental RNA interference (RNAi) via synthetic small interfering RNAs (siRNAs), the existence of a natural antiviral RNAi response in mammals is debated. First, in many infected somatic cells, viral double-stranded RNA (dsRNA) triggers the potent and non-sequence-specific interferon (IFN) response that may have largely supplanted antiviral RNAi functions. Second, several mammalian viral proteins display viral suppressor of RNAi (VSR)-like activities still awaiting validation in authentic virus expression contexts. Third, diverse virus-infected mammalian cell types accumulate virus-derived small RNAs (vsRNAs), but these have unspecified functions and lack the biochemical features, size, and distribution patterns of plant and invertebrate viral siRNAs. It remains unknown whether a virus infection triggers production of canonical viral siRNAs in mammals or if mammalian virus infections require specific suppression of an antiviral RNAi response.

The disclosure is based on the discovery that RNA silencing acts as an antiviral defense mechanism in animal cells. Specifically, the disclosure establishes that a virus can induce strong viral RNA silencing and that the same viruses are equipped with an effective silencing suppressor essential for infection. Prior to this discovery, it was known that RNA degradation could be artificially induced by dsRNA in animals and that RNA silencing was an antiviral defense mechanism in plants, but it was not known that RNA degradation could occur in response to a natural trigger, i.e., a virus, in animals.

The discovery of a novel animal antiviral defense mechanism offers immense opportunities for treating human and animal viral diseases and for gene therapy. For example, viral infections can be treated by enhancing the RNA silencing antiviral defense response, or by blocking the action of suppressors of RNA silencing. In addition, since RNA viruses are potent initiators of RNA silencing, foreign sequences from endogenous human genes or heterologous viruses can be inserted into attenuated RNA viruses to produce a novel class of therapeutic vectors for either inactivating certain human genes (gene therapy) or targeting other viruses in trans (as a live attenuated vaccine).

Thus, in one embodiment, attenuated vaccines can be produced by reducing or eliminating the viral gene that produces the viral suppressor of RNAi (VSR). The gene can be genetically modified or knockout in a recombinant viral genome. For example, in one embodiment, the disclosure provides an attenuated virus lacking a functional viral suppressor of RNAi (VSR), wherein the virus is capable of infecting a host cell and wherein the host cell can mount a defense to the viral vector using siRNA. In one embodiment, for example, the virus is an Ebola virus and the virus lacks a functional VP35 (SEQ ID NO:1):

MTTRTKGRGHTAATTQNDRMPGPELSGWISEQLMTGRIPVSDIFCDIENN

PGLCYASQMQQTKPNPKTRNSQTQTDPICNHSFEEVVQTLASLATVVQQQ

TIASESLEQRITSLENGLKPVYDMAKTISSLNRVCAEMVAKYDLLVMTTG

RATATAAATEAYWAEHGQPPPGPSLYEESAIRGKIESRDETVPQSVREAF

NNLDSTTSLTEENFGKPDISAKDLRNIMYDHLPGFGTAFHQLVQVICKLG

KDSNSLDIIHAEFQASLAEGDSPQCALIQITKRVPIFQDAAPPVIHIRSR

GDIPRACQKSLRPVPPSPKIDRGWVCVFQLQDGKTLGLK.

In another embodiment, the virus comprises a Nodamura virus and the virus lacks a function B2 protein (SEQ ID NO:2):

MTNMSCAYELIKSLPAKLEQLAQETQATIQTLMIADPNVNKDLRAFCEFL

TVQHQRAYRATNSLLIKPRVAAALRGEELDLGEADVAARVRQLKQQLAEL

EMEIKPGHQQVAQVSGRRKAAAAAPVAQLGRVGVVNE.

In yet another embodiment, the attenuated virus comprises either of Ebola or Nodamura virus above lacking function VP35 or B2, respectively, and comprising a further heterologous polynucleotide that expresses an antigen or desired polypeptide.

In one embodiment, the disclosure provides recombinant attenuated virus comprising viral sequence sufficient to activate viral RNA silencing in a host. Such polynucleotides typically lack sequences encoding functional viral RNA silencing suppressors (VSRs). In another embodiment, the disclosure provides methods of identifying additional RNA silencing suppressors. Suppressors can be identified by functional methods using recombinant DNA constructs of this disclosure or by bioinformatic/sequence analysis methods to identify other genes with similar key features. In another embodiment, this disclosure provides recombinant DNA constructs for inactivating genes, wherein the construct comprises viral sequence sufficient to activate RNA silencing and a target gene for inactivation. In still yet another embodiment, this disclosure provides methods for identifying genes in the antiviral RNA silencing pathway using recombinant DNA constructs of this disclosure. The disclosure also provides methods for identifying modulators of the RNA silencing suppressors and the antiviral RNA silencing pathway, as well as methods for treating animals infected with virus and for preventing viral infections by up-regulating the antiviral pathway. The disclosure further provides any attenuated viral vector lacking a functional VSR. Additionally, the disclosure includes use of such attenuated viruses lacking a function VSR for vaccination and for inducing an immune response to an antigen carried by the attenuated virus (e.g., a heterologous antigen).

The disclosure provides vectors with viral polynucleotide sequences sufficient to activate RNA silencing, but which lack a functional VSR gene. These vectors-have multiple uses, including gene therapy, immunization and vaccination, and identification of genes in the antiviral RNA silencing defense pathway. These vectors typically lack sequences encoding functional viral RNA silencing suppressors. This is typically accomplished by deleting all or substantially all the sequences encoding suppressors, mutating suppressor sequences to disrupt function, or mutating suppressor sequences to reduce activity. In certain instances, the polynucleotides can also encode natural suppressors with weak activity.

One of skill will recognize that an attenuated virus includes any virus capable of inducing siRNA silencing/suppression in a host cells. In certain embodiments, the vectors are infectious viral vectors. Such vectors comprise a viral genome lacking a VSR and can optionally include a heterologous coding sequence of a polypeptide of interest. In further embodiment, the viral genome has been modified to remove sequences that confer virulence in addition to removal of the VSR gene.

Infectious viral vectors of the disclosure are typically capable of infecting a broad range of hosts including humans, dogs, cats, horses, cows, monkey, and other mammalian species; usually, these viral vectors are capable of efficiently infecting humans. Any viruses that have been developed for use as gene therapy vectors can be used. Exemplary viruses include retroviruses (including lentiviruses), adenoviruses, murine leukemia virus, adeno-associated viruses, herpes simplex virus type 1, etc. Additionally, viral vectors can be derived from the genome of human or bovine adenoviruses, vaccinia virus, herpes virus, minute virus of mice (MVM), HIV, sindbis virus, Rous sarcoma virus, and MoMLV. In certain embodiments, the infectious viral vectors of the disclosure further comprise polynucleotide sequences that alter the host range. Infectious viral vectors with a host range different from or broader than that of the native viral polynucleotide sequence can be constructed by incorporating these determinants of host range.

Viral DNA or RNA can be introduced into cells using standard methods known to those of skill in the art. Such methods include electroporation, the use of DNA guns, calcium-phosphate mediated transfection, lipid-mediated transfection, the use of kits designed for such purposes, and the like. The vectors can also be introduced via other systems including, but not limited, to an HVJ (Sendai virus)-liposome gene delivery system (see, e.g., Kaneda et al., Ann. N.Y. Acad. Sci. 811:299-308 (1997)); a "peptide vector" (see, e.g., Vidal et al., CR Acad. Sci III 32:279-287 (1997)); as a gene in an episomal or plasmid vector (see, e.g., Cooper et al., Proc. Natl. Acad. Sci. U.S.A. 94:6450-6455 (1997), Yew et al. Hum Gene Ther. 8:575-584 (1997)); as a gene in a peptide-DNA aggregate (see, e.g., Niidome et al., J. Biol. Chem. 272:15307-15312 (1997)); as "naked DNA" (see, e.g., U.S. Pat. No. 5,580,859 and U.S. Pat. No. 5,589,466); in lipidic vector systems (see, e.g., Lee et al., Crit Rev Ther Drug Carrier Syst. 14:173-206 (1997)); polymer coated liposomes (Marin et al., U.S. Pat. No. 5,213,804, issued May 25, 1993; Woodle et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al., U.S. Pat. No. 5,279,833, issued Jan. 18, 1994.

Portions of a virus sufficient to activate RNA silencing can easily be identified by using standard mutagenesis and deletion methods known to those of skill in the art. For example, a vector comprising a viral genome with various deletions and lacking functional RNA silencing suppressors, can be transfected into cells and tested for RNA silencing activity. Assays for RNA silencing include measuring accumulation of viral RNA or detecting intermediates produced during RNA degradation, e.g., siRNA, etc.

Vectors of the disclosure can be constructed using standard methods in molecular biology, such as those described in many general molecular biology textbooks such as Sambrook et al., Molecular Cloning a Laboratory Manual 2nd Ed. Cold Spring Harbor Press, Cold Spring Harbor (1989) and Ausubel et al., Current Protocols in Molecular Biology, (current edition).

In one embodiment, the disclosure provides RNA silencing suppressors of animal viruses. These animal viruses can be DNA or RNA viruses. A particular virus may encode more than one RNA silencing suppressor.

In one embodiment, the disclosure provides for a RNA silencing suppressor referred to as B2 (e.g., SEQ ID NO:2). In other embodiments, the disclosure provides RNA silencing suppressors for other animal viruses, including those viruses where infection is widespread, has severe effects, or where there has been limited success in developing effective vaccines or therapeutics. Exemplary viruses include HIV, HCV, HBV, influenza viruses, measles virus etc. In certain embodiments, the disclosure also provides methods of identifying endogenous/cellular RNA silencing suppressors (see Anandalakshmi et al., Science 290:142-144 (2000)). The identified VSR sequences (e.g., SEQ ID NO:1 and 2) can be used to identify homologs from other viruses using wet-bench experimentation alone or in combination with readily available bioinformatics.

Silencing suppressors can be identified using the teachings provided here and standard methods known to those of skill in the art. For example, suppressors are identified by sequence analysis, functional tests using vectors described herein or combinations thereof.

Thus analysis of viral genomes can be used to identify RNA silencing suppressors. Viral genomes are thus conveniently examined for "overlapping" genes. Overlapping genes are often conserved only in a specific taxonomic grouping and their encoded proteins are likely to have unusual biochemical properties. In some embodiments, particular attention is paid to "overlapping" genes of RNA polymerase in the +1 reading frame. However, it will be readily appreciated by those of skill in the art that putative viral RNA silencing suppressors are not limited to this particular embodiment; the suppressors can overlap with any gene in any reading frame.

In some embodiments, viral genomes will be examined for genes that appear to be required for virulence and virus accumulation, but for which there is no known specific function. Viral genomes are also typically examined for genes that are essential for viral infection in certain cell types but not essential in other cell types. Genes with these characteristics are good candidates for suppressor genes (see TABLE 1).

TABLE 1

RNA silencing suppressors for various viruses.

| Virus name | Genome type | Suppressor | Overlapped gene | Reference |
|---|---|---|---|---|
| HIV-1 and HIV-2 | RNA | tat, rev | env | Keese & Gibbs PNAS 89: 9489-9493 (1992) |
| HIV-1 | RNA | vpu | env | Keese & Gibbs PNAS 89: 9489-9493 (1992) |
| HIV-2 | RNA | vpx | vif | Keese & Gibbs PNAS 89: 9489-9493 (1992) |
| Measles virus | RNA | C and V | P | Fields Virology, Fourth Edition. 2001 Chpt 44 |
| Influenza virus B | RNA | NB | NA | Fields Virology, Fourth Edition. 2001 Chpt 46 |

TABLE 1-continued RNA silencing suppressors for various viruses.

| Virus name | Genome type | Suppressor | Overlapped gene | Reference |
| --- | --- | --- | --- | --- |
| Influenza virus B | RNA | BM2 | M1 | Fields Virology, Fourth Edition. 2001 Chpt 46 |
| Influenza virus A/B/C | RNA | NS1/NS2 | NS1/NS2 | Fields Virology, Fourth Edition. 2001 Chpt 46 |
| Papillomaviruses | DNA | E4 | E2 | Fields Virology, Fourth Edition. 2001 Chpt 65 |
| Hepadnaviruses (includes Hepatitis B virus) | DNA | X | P | Fields Virology, Fourth Edition. 2001 Chpt 86 |
| Hepatitis C virus | RNA | F | C | Xu et al. EMBO J 20: 3840 (2001) |

Once putative RNA silencing suppressors are identified, they can be tested using any functional test known to those of skill in the art, such as those described in the following section.

RNA silencing suppressors can also be identified via functional tests using vectors described herein. Typically, a test will examine the ability of a polypeptide encoded by a candidate RNA silencing suppressor gene to hinder, block, or slow RNA silencing induced by the viral vector.

In a certain embodiment, a method of the disclosure comprises expressing a polynucleotide sequence of a virus sufficient to activate RNA silencing as defined herein ("silenced viral sequence") in a cell, introducing a polynucleotide encoding a candidate RNA silencing suppressor into the cell, and testing for increased rate or extent of accumulation of the "silenced viral sequence".

It will be appreciated that the polynucleotide sequence can be part of either an infectious vector or a non-infectious vector. It will further be appreciated that the "silenced viral sequence" and candidate suppressor sequence can either be on the same or different vector and introduced at varying times. In some embodiments, the "silenced viral sequence" is introduced before the candidate suppressor gene. Based on studies with plant suppressors, it is known that certain viral RNA silencing suppressors target early stages of RNA silencing, while others target later stages (see, Li and Ding, Curr. Opin. Biotech. 12:150-154 (2001)). Suppressors which target early stages of the RNA silencing pathway are unlikely to be active unless expressed before or during the initiation of RNA silencing. Therefore, in some embodiments, the suppressor gene is either introduced before or during RNA silencing—either on the same vector as the "silenced viral sequence", on a separate vector prior to introduction of the "silenced viral sequence", or on the same vector as the "silenced viral sequence" but engineered to be expressed first.

The "silenced viral sequence" can be expressed in any animal cell where the antiviral RNA silencing pathway is activated in response to the "silenced viral sequence". In certain embodiments, mammalian cells are used.

Candidate RNA silencing suppressors can be any gene identified by sequence analysis described in the above section or any other gene which has properties or a sequence which indicates that the gene may be a RNA silencing suppressor. For identification of viral RNA silencing suppressors, the candidate gene can be from a virus. For identification of endogenous suppressors, the candidate gene can be from the genome of the same organism as the host cell, or from the genome of a different organism.

RNA accumulation of the "silenced viral sequence" can be measured using any method known to those of skill in the art; these methods include Northern blot or assays to detect reporter molecules linked to the polynucleotide. The reporter molecules can either be detectable fluorescence molecules or selectable antibiotic markers. Suppression of RNA silencing allows expression of GFP, which can be visualized by UV illumination. Active RNA silencing generates a red fluorescent zone.

In certain embodiments, the above-described attenuated viral vectors lacking a function VSR further comprise a polynucleotide of interest. Those of skill in the art will recognize that vectors of the disclosure can be used for any application where gene delivery or protein expression levels of a specific gene are desired. The vectors of the disclosure are particularly useful for methods where inhibiting viral spread is important, but targeted delivery of a gene sequence is desirable.

The disclosure also provides methods for treating or preventing viral infection by up-regulating degradation of viral RNA and thus reducing virus levels. Typically, degradation of viral RNA is up-regulated by either activating the antiviral RNA silencing pathway or by inhibiting any RNA silencing suppressors using modulators identified with the methods disclosed herein.

In another embodiment, an attenuated virus is used as a vaccine, wherein the virus lacks a functional suppressor system (e.g., a VSR) such that the virus comprises antigens yet has limited replication and spread capacity due to the attenuated virus's inability to inhibit the host cells RNA silencing pathway.

In another embodiment, the antiviral silencing pathway in a host cell is activated by administering a pharmaceutical composition that either upregulates the expression level of a gene in the pathway or enhances of the activity of a gene in the pathway.

In another embodiment, the suppression of RNA silencing is blocked or reduced by administering a VSR inhibiting agent that either inhibits the activity of a RNA silencing suppressor or reduces the expression level of a RNA silencing suppressor. Examples of such agents including antibodies and siRNAs.

Accordingly, the disclosure provides an antibody or antibody fragment that recognizes and binds to a VSR suppressor, wherein the antibody or antibody fragment comprises a variable heavy chain ($V_E$) domain and/or a variable light chain ($V_L$) domain, and wherein (a) the $V_H$ domain comprises an amino acid sequence that includes one, two or three complementarity determining regions (CDRs). In another embodiment, the antibody or antibody fragment is selected from the group consisting of: (a) an antibody or scFv with heavy and light chain domains comprising the complementarity determining regions; and (b) an antibody or scFv with heavy and light chain domains comprising the complementarity determining regions. In another embodiment of any of the foregoing, the heavy and light chain domains are linked to an Fc region, typically through a linker/hinge domain. In one embodiment, the scFv is soluble under physiological conditions. In another embodiment, the scFv is murine. In yet another embodiment, the scFv is humanized.

The disclosure provides antibodies, antibody fragments and humanized antibodies that bind to a VSR suppressor. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tumors, plaques and diseased tissue. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. Coli, thus allowing the facile production of large amounts of these fragments. Antibody fragments can be isolated from the antibody phage libraries. Alternatively, Fab'-SH fragments can be directly recovered from E. Coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

The disclosure provides methods of inducing a viral response in a subject comprising administering a composition containing the attenuated virus to a subject. In the methods, the composition may be administered as a single dose, a double dose or multiple doses. The administration route in humans may be inhalation, intranasally, orally, and parenterally. Examples of parenteral routes of administration include intradermal, intramuscular, intravenous, intraperitoneal and subcutaneous administration. The range of the human immunization dose may be about $10^2$ to about $10^9$ PFU. The methods disclosed herein induce humoral and cellular immune responses in a subject. Moreover, in embodiments of the disclosure the methods induce a protective immune response in the subject. The protective immune response may be where the subject exhibits no symptoms of an infection, a reduction in symptoms, a reduction in virus titer in tissues or nasal secretions, and/or complete protection against infection by a certain virus.

The disclosure also provides kits for administering an attenuated virus of the disclosure packaged in a manner which facilitates its use in practicing methods of the disclosure. In one embodiment, such a kit includes an attenuated virus or composition described herein, packaged in a container such as a sealed bottle or vessel, with a label affixed to the container or included in the package that describes use of the compound or composition in practicing the method. Preferably, the attenuated virus or composition is packaged in a unit dosage form. The kit may further include a device suitable for administration according to a specific route of administration or for practicing a screening assay. Preferably, the kit contains a label that describes use of the attenuated virus. In some embodiments, the kit comprises instructions for administration to a human subject.

Also provided herein are methods of producing an attenuated virus expressing a mutated VSR polynucleotide of the disclosure. For example for producing a mutated VSR polynucleotide of the disclosure comprises the steps of: (a) infecting a suitable permanent cell line (e.g., cancerous mammalian cell line) with an attenuated virus, (b) transfecting the infected cells with a plasmid comprising a polynucleotide which encodes a mutated VSR polynucleotide sequence and flanking sequences which are homologous to a VSR coding region of the NoV genome, (c) growing the cells to allow the plasmid to recombine with the NoV genome during replication of the NoV in the cells thereby inserting the gene cassette into the NoV genome in the non-essential region, and (d) obtaining the recombinant VSR produced. Exemplary cells include chicken embryo cells are described in U.S. Pat. No. 5,391,491 (Slavik et al. 1983) or vertebrate cell lines, such as MRC-5, MRC-9, CV-1 (African Green monkey), HEK (human embryonic kidney), PerC6 (human retinoblast), BHK-21 cells (baby hamster kidney), BSC (monkey kidney cell), and LLC-MK2 (monkey kidney). BHK-21 cells are an accepted cell line for production of viral vaccines according to the World Health Organization. In some embodiments, the attenuated virus of the disclosure is produced in BHK-21 cells.

The following examples are intended to illustrate but not limit the disclosure. While they are typical of those that might be used, other procedures known to those skilled in the art may alternatively be used.

EXAMPLES

Cell Lines and Viruses.

BHK21 cells were obtained from American Type Culture Collection (ATCC) and were propagated in complete growth medium (Dulbecco's Modified Eagle's Medium (DMEM)+ 10% Fetal Bovine Serum) at 37.0° C., 5% $CO_2$. Nodamura virus (NoV) was rescued from the infectious cDNA clones and was propagated in BHK21 cells. B2-deficient mutant virus (NoVΔB2) was generated by transfection of BHK21 cells with in vitro transcripts of the full-length NoV cDNA clones for wildtype RNA-2 and mutant RNA-1 containing three point mutations (U2745C, U2754C and C2757G) to terminate translation of the B2 ORF without affecting the −1 overlapping ORF for the viral RNA-dependent RNA polymerase. The genotype of NoVΔB2 was confirmed by RT-PCR and DNA sequencing and by Western blotting using the rabbit antibodies against the B2 protein. NoVΔB2 concentrations were determined by comparing the genomic RNA content in virons with that in NoV virions.

Cell Culture and In Vitro Differentiation of mESCs:

Female PGK (129×PGK background), male HM1 (129/Ola background), Dcr$^{Flx/Flx}$ and Dcr$^{-/-}$ (hybrid background) were cultured in Dulbecco's Modified Eagle Media (DMEM) (Invitrogen), containing 15% of a special selected batch of fetal bovine serum FBS (Life Technologies) tested for optimal growth of mESCs, 1000 U/mL LIF (Millipore), 0.1 mM 2-β mercaptoethanol (Life Technologies), 0.05 mg/mL of streptomycin (Sigma), and 50 U/mL of penicillin (Sigma) on a gelatin coated support in the absence of feeder cells. Male E14 (129/Ola background) mESC line and E14-FHA-hAgo2 (created by the transfection of the plasmid pIRESneo-FLAG/HA Ago2 corrected (Addgene plasmid 10822) and selected on G418-containing medium) were cultured in Glasgow MEM medium (Invitrogen), containing 15% FBS (Life Technologies), 1000 U/mL LIF (Chemicon), 0.1 mM 2-β-mercaptoethanol (Invitrogen), 0.05 mg/mL of streptomycin (Invitrogen) and 50 U/mL of penicillin (Invitrogen), 2 mM L-Glutamine, 1 mM Sodium Pyruvate MEM and 1×MEM Amino Acid on a gelatin-coated support in the absence of feeder cells. The culture medium was changed daily. All cells were grown at 37° C. in 8% $CO_2$. New CreERT2-Dcr$^{Flx/Flx}$ mESCs were isolated from the cross of floxed Dcr$^{Flx/Flx}$ mice and ROSA-CreERT2 mice. Genotyping primers used for the characterization of these cell lines are presented in table S3. The inducible mESC line (E7 line) deficient for the four mouse Argonautes (Ago1,2,3,4_KO) and carrying a floxed human Ago2 transgene. Dcr and hAgo2 deletions were induced with 4-OHT (Tam) stock solution (1 mM, dissolved in 100% ethanol) diluted 1:1000 in cell culture medium to a final concentration of 1 µM. To generate Dcr$^{-/-}$, Dcr$^{Flx/Flx}$ mESCs were treated with 4-OHT for 12 days and isolated clones propagated for several passages to obtain constitutive Dcr$^{-/-}$ mESC lines used in the study. Deletion of Dcr was verified at the genomic level by genotyping and at the functional level by the loss of production of various miRNAs (miR-295, miR-16) as well as the increased abundance of known targets of miRNAs (Hmga2 and Btg2). Embryoid body cultures were established by aggregation of mESCs in a low-adherent tissue culture dish into LIF-free DMEM, 10% FBS medium until day 10 of differentiation. The culture medium was changed daily. All cells were grown at 37° C. in 8% $CO_2$. BHK-21 cells were cultivated in Dulbecco's modified Eagle with Glutamax™ medium (Gibco, Life Technologies) supplemented with 10% fetal bovine serum "Gold" (PAA), 100 U/mL penicillin (Sigma) and 0.1 mg/mL streptomycin (Sigma).

Production of Recombinant Virus:

EMCV was produced using the recombinant vector containing the full-length cDNA clone (pBL/T7EMCgB2887) of an EMCV strain (2887A/91). Briefly, pBL/T7EMCgB2887 (10 µg) was linearized with Not I for 4 hours and DNA purified using GeneJET Gel Extraction and DNA Cleanup Micro Kit (Fermentas). In vitro transcription was performed with T7 RNA polymerase on the linearized plasmid (1 μg) at 37° C. for 2 hours using the MEGAscript kit (Ambion). DNA was then digested by Turbo™ DNAse (Ambion) for 30 min at 37° C. and RNA extracted with Tri-Reagent (Sigma) according the manufacturer's instructions. The size of the synthesized RNA was determined on formaldehyde agarose electrophoresis. In vitro transcribed RNA (4 μg) was transfected in 50% confluent BHK-21 cells in a six-well culture dish, using 3:1 ratios of FuGENE 6 (Roche Applied Science) transfection reagent (μL) to DNA (μg), respectively. Two days later, when cytopathic effect (CPE) was apparent, supernatant was harvested and clarified by centrifugation (1500 rpm/300 g, 5 min). The rescued virus was passaged on BHK-21 cells by infecting 50% confluent cells in T75 Flask with 1 mL EMCV-containing supernatant and cells incubated for 1 hour at 37° C. in 5% CO2. Then culture medium was added and cells incubated for one day until appearance of CPE. Cells were then lysed by 3 freeze-thaw cycles and supernatants were collected, clarified by centrifugation (1500 rpm/300 g, 5 min), aliquoted and stored at −80° C. Titers were determined by 50% Tissue Culture Infective Dose ($TCID_{50}$) assays on BHK-21 cells. Briefly, BHK-21 cells were infected with 10-fold dilutions of the virus and incubated at 37° C. in 5% $CO_2$ for one to two days. CPE was determined by inspection under the microscope and the numbers of wells with CPE used to calculate $TCID_{50}$ using Reed and Muench statistical method. NoV and NoVΔB2 DNA clones and virion production are as described herein.

Infections of mESCs:

At the day of infection, the medium was changed and EMCV added at a dose (determined in BHK-21 cells) of 50-100 $TCID_{50}$/cell on 50-80% confluent mESCs cultured in T75 flasks. Cells were incubated for 3 or 6 hours postinfection at 37° C. in 8% $CO_2$ and then washed twice with phosphate buffered-saline 1× (PBS1×), trypsinized and then collected. Cells were pelleted, washed one more time with PBS1× and processed for downstream applications. For experiments aimed at testing the DCR-dependency of EMCV-derived small RNAs were used $Dcr^{Flx/Flx}$ and constitutive $Dcr^{-/-}$ mESCs maintained in culture over multiple passages and seeded in T-75 flasks one day before the infection. The density was such that a similar number of $Dcr^{Flx/Flx}$ and $Dcr^{-/-}$ mESCs was attained on the day of infection. Cells were then challenged with EMCV following the aforementioned procedure for infection. Infections with NoV and NoV ΔB2: At the day of infection, a mix was prepared in which virus preparations (1 mL of NoV or 1 mL of NoVΔB2) were mixed with FBS-free Glasgow MEM complete medium (9 mL). E14 mESC line grown in T75 flasks at confluency of 30-40% were washed twice with Dulbecco's Phosphate-Buffered Saline (DPBS) containing calcium and magnesium (Gibco, Life Technologies) and then infected by addition of the infection mix. Cells were incubated for 1 hour at 37° C. in 8% $CO_2$ and then medium was changed and cells incubated for 3 days at 37° C. in 8% $CO_2$. Cells were then washed with PBS1× without calcium and magnesium (Gibco, Life Technologies), trypsinized and pelleted for downstream applications. For the genetic rescue experiment, infections were conducted on the inducible mESC line (E7 line) deficient for the four mouse Argonautes (Ago1,2,3,4_KO) and carrying a floxed human Ago2 transgene. Before infection, the E7 mESC line was treated with 4-OHT (used at 1 μM) for 2 days to induce the deletion of the Ago2 transgene, while untreated E7 mESCs were used a control. Two days later, untreated and treated E7 mESCs were challenged with NoV or NoVΔB2 following the aforementioned procedure of infection. Cells were then incubated in the presence of 4-OHT for a further 3 days at 37° C. in 8% CO2, washed with PBS1× without calcium and magnesium, and pelleted for downstream applications.

Library Construction and Sequencing of Virus-Derived Small RNAs.

Libraries of small RNAs from cell culture and suckling mice were constructed using the method that depends on the 5' monophosphate of small RNAs as described in Han et al. (*J. Virol.* 85:13153-13163 (2011)). Total small RNAs from BHK-21 cells 2 or 3 days after inoculation with NoV or NoVΔB2 were used to construct libraries with a barcode added to the 5' ligation adaptors. Libraries of total small RNAs from the hind limb tissues of suckling mice 1 day or 2 days after inoculation with NoVΔB2 or 4 days after inoculation with NoV were constructed using TruSeq Small RNA Sample Preparation Kit of Illumina (San Diego, Calif.). The libraries were sequenced by Illumina HiSeq 2000. Virus-derived small RNAs (vsRNAs) reads with 100% identity were mapped to Nodamura virus genome (NC_002690.1 and NC_002691.1) using Bowtie 0.12.9. Reads were identified as cellular microRNAs only for those that were 100% identical to the full-length mature miRNAs in miRBase 19. For BHK-21 cell libraries, the miRNA list was obtained from a previous study characterizing miRNAs in Chinese hamster ovary cell lines. Subsequent bioinformatic analysis of mature cellular miRNAs and viral small RNAs was carried out using Perl scripts. Pairs of complementary 22-nt vsRNAs in each library in different distance categories were computed by modifying previously described basic principles in Parameswaran et al. (*PLoS Pathog.* 6:e1000764 (2010)) and Brennecke et al. (*Drosophila. Cell* 128:1089-1103 (2007)) with modifications. The program calculates the counts of pairs in each nucleotide distance category between the 5' and 3' ends of complementary 22-nt vsRNAs using Equation 1:

$$\oint(x)_{x=-a,-a+1,\ldots,b-1,b} = \sum_{i=1}^{i=t} \sum_{j=1}^{j=l_{xi}} \left( \frac{n_i}{p_i} \times \frac{m_j}{q_j} \right) \quad (1)$$

x indicates each distance category.
a and b are determined by the sizes of the small RNAs examined.
f(x) indicates the total number of small RNA pairs for each distance category.
i indicates a small RNA from positive strand.
t indicates the total number of positive-strand small RNAs.
j indicates a small RNA from negative-strand which overlaps with small RNA i in the distance category x.
$1_{xi}$ indicates the total number of negative-strand small RNAs that meet the requirement determined by x and i.
$n_i$ indicates the repeat number of the small RNA i.
$p_i$ indicates the multiple viral genome hit number of the small RNA i.
$m_j$ indicates the repeat number of the small RNA j.
$q_j$ indicates the multiple viral genome hit number of the small RNA j.

Stable Cells Lines.

Figure 3:
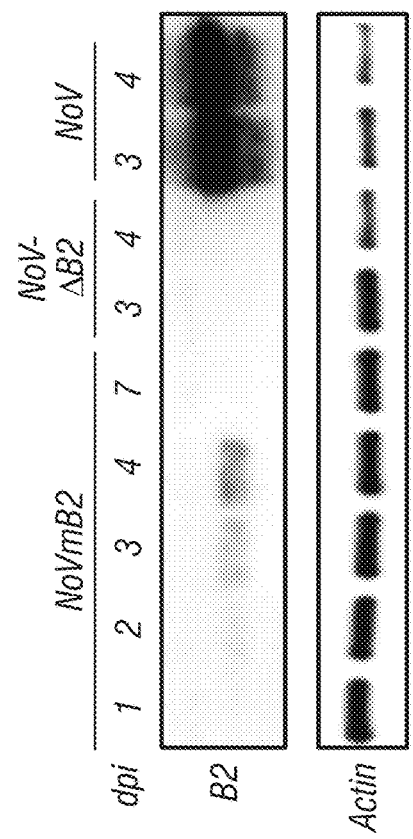
FIG. 3 provides for Western blot detection of B2 and mB2 proteins during sucking mouse infection. BALB/c mice of 6 to 8 days old after birth were inoculated by intraperitoneal injection (IP) with 10 μl, 30 μl or 50 μl respectively from the titrated set of NoV, NoVΔB2, NoVmB2 stock preparations. The mutant B2 protein carrying R59Q mutation appeared to migrate faster than the wild type B2 protein.

B2 and VP35 genes were cloned into a pQCXIP Retroviral Vector (pQCXIP-B2 and pQCXIP-VP35). BHK cells were plated in a 6 well plate the day before transfection. The cells were transfected with LASV GP protein, gag-pol and pQCXIP-B2 (or pQCXIP-VP35) expression plasmids using TransIT®-LT1 transfection reagent (Mirus, Madison, Wis.) following the supplier's recommended protocol. 6 hrs following transfection, transfection medium was removed and cells maintained in new growth medium. The supernatant was harvested 48 hours after transfection and filtered using 0.45 μm syringe filter. Stable BHK-21 cell lines expressing B2 of Nodamura virus (NoV) or virion protein 35 (VP35) of Ebola virus were constructed and selected using pseudotyped murine leukemia viruses for transduction as described in Huang et al. (*PLoS Pathog.* 7:e1001258 (2011)). These hamster cell lines were referred as BHK-B2 and BHK-VP35 cells. NoV and its B2-deficient mutant (NoVΔB2) were initially rescued from the infectious in vitro transcripts of full-length cDNA clones in BHK-21 cells as described in Johnson et al. (*Virology* 305:436-451 (2003)). RNA-1 of NoVΔB2 contained three point mutations (U2745C, U2754C and C2757G) to terminate translation of the B2 ORF without affecting the −1 overlapping ORF for the viral RNA-dependent RNA polymerase as described in Johnson et al. RNA-1 of NoVmB2 contained a single G to A substitution at nucleotide 2919 of RNA1, which changed the 59th codon CGA (Arg) of B2 ORF to CAA (Gln) without altering the coding for Ser (TCG to TCA) at −1 overlapping ORF. The genotypes of NoVΔB2 and NoVmB2 were confirmed by sequencing and Western blotting using the rabbit antibodies against NoVΔB2. mB2 migrated slightly faster than the wildtype B2 in Western blot analysis (see FIG. 3)

Infection in Cell Culture.

NoV was propagated in BHK-21 cells whereas NoVΔB2 and NoVmB2, were amplified in the stable BHK-B2 cells since both were defective in the infection of BHK-21 cells. Since NoV was noncytolytic and NoVΔB2 infection was defective, the copy number of the viral genome RNA1 in the stock preparations of NoV and NoVΔB2 as well as a NoVmB2 preparation were determined by a real-time RT-PCR protocol previously reported. Briefly, a 10-fold dilution series of NoV RNA-1 with known concentrations were synthesized in vitro by T7 polymerase and used to establish a standard curve by real-time RT-PCR to amplify nucleotides 595-732 of RNA-1 by NoV Replicase_Fwd and NoV Replicase_Rev (see TABLE 2). Virion RNAs extracted from a defined volume of each of the virus stock preparations were quantified by the same real-time RT-PCR using the standard curve as the reference. This quantification method showed that the stocks of NoV, NoVΔB2 and NoVmB2 contained $7 \times 10^8$, $3.6 \times 10^8$, and $1.3 \times 10^8$ genome RNA copies per ml, respectively.

For infection in cell culture, BHK-21, BHK-B2 or BHK-VP35 cells were seeded in 6-well plates and mock-inoculated or infected in each well by NoV and NoVΔB2 with the same amount of viral genome copies ($5 \times 10^6$). Cells were harvested every 12 hours up to 72 hours post infection (hpi) and total RNAs extracted from cells were used to measure virus accumulation at each time points by real-time RT-PCR to amplify nucleotides 595-732 of RNA-1 using β-actin mRNA as the internal control (see below). The accumulation of NoV or NoVΔB2 RNAs at 48 and 72 hpi was also detected by Northern blot analysis (see below) and the phosphorimager readings of the RNA-1 signal for each infection were recorded. The time course experiments were repeated two additional times.

Infection in Suckling Mice.

Each of five BALB/c mice of 6 to 8 days old after birth (Jackson Lab, Bar Harbor, Me.) was inoculated by intraperitoneal injection (IP) as described (29) with 10 μl, 30 μl or 50 μl respectively from the titrated set of NoV, NoVΔB2, NoVmB2 stock 2 preparations. Thus, the ratio of the viral genome copy numbers inoculated to each mouse was 1 (NoV):1.54 (NoVΔB2):0.93 (NoVmB2). At 1, 2, 3, 4 and 7 days post inoculation (dpi), total RNA was extracted separately from individual fore (2 samples) and hind (2 samples) limb tissues of one anesthetized suckling mouse using TRIzol (Invitrogen, Carlsbad, Calif.) according to manufacturer's instructions. The experiment was repeated twice. Thus, each time point for each virus was represented by four RNA samples from each of the three mice used in three biological replicates. Since the titer of NoV used in this work caused 100% mortality in suckling mice by 5 days post inoculation, however, the time course infection with NoV was terminated in the subsequent experiments and the infected mice euthanized 4 days post inoculation when hind limp paralysis became apparent.

Detection of the Viral High and Low Molecular Weight RNAs in suckling mice.

Figure 6A:
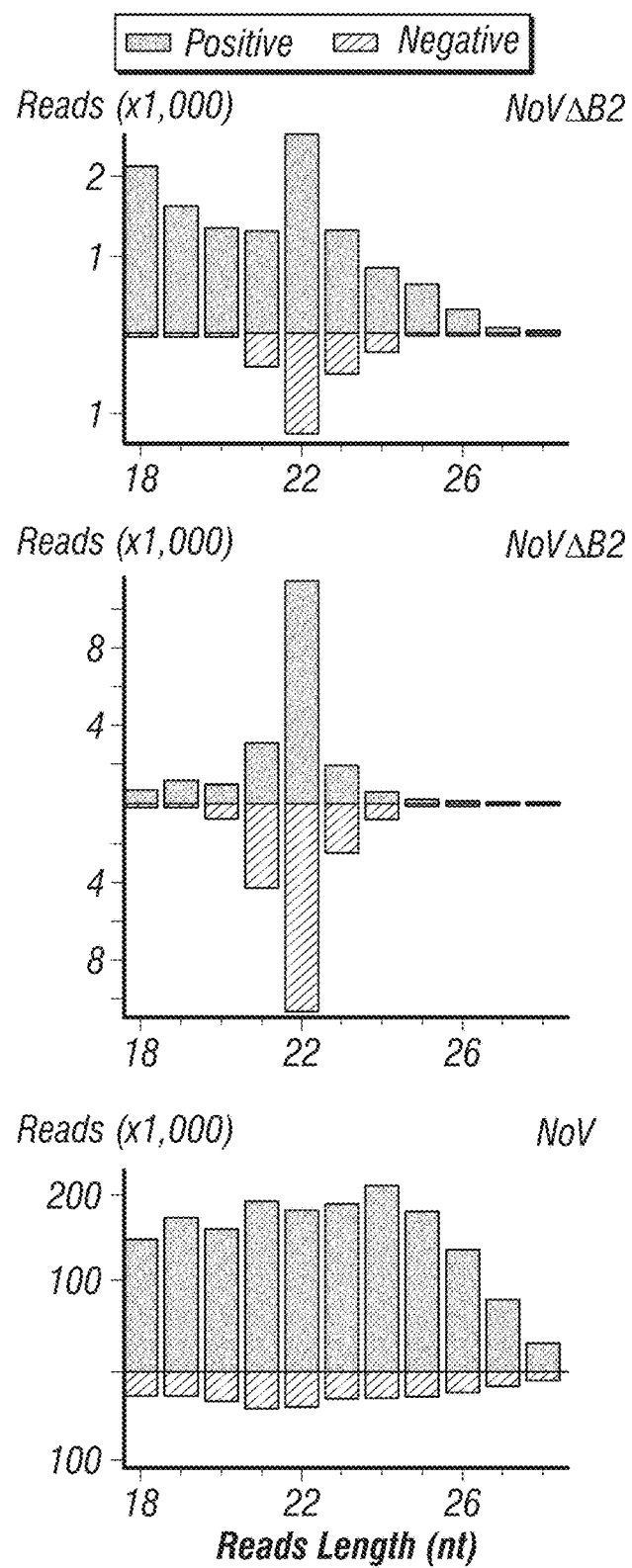
FIG. 6A-D presents the properties of mouse viral siRNAs produced in vivo. (A) Length distribution and abundance of positive- or negative-strand vsRNAs from mice 1 or 2 days post inoculation (dpi) with NoVΔB2 or with NoV at 4 dpi. (B) Virus genome distribution of 21- to 23-nt viral siRNAs sequenced from either sucking mice (top two panels) or BHK-21 cells (bottom two panels) after infection by NoVΔB2. The functional proteins encoded by the viral bipartite RNA genome and transcription of B2 mRNA (RNA3) from RNA-1 are shown. Arrows indicate the positions of the four locked nucleic acid probes used to detect negative-strand viral siRNAs in mice. (C) Total counts of pairs of complementary 22-nt vsRNAs of NoVΔB2 and NoV in each distance category as defined in FIG. 1B. (D) Nucleotide frequencies at each position of the total (top) and unique (bottom) 22-nt negative-strand viral siRNAs. The viral open reading frames coding for three viral proteins are translated from RNAs 1, 2 and 3, respectively.
Figure 6B:
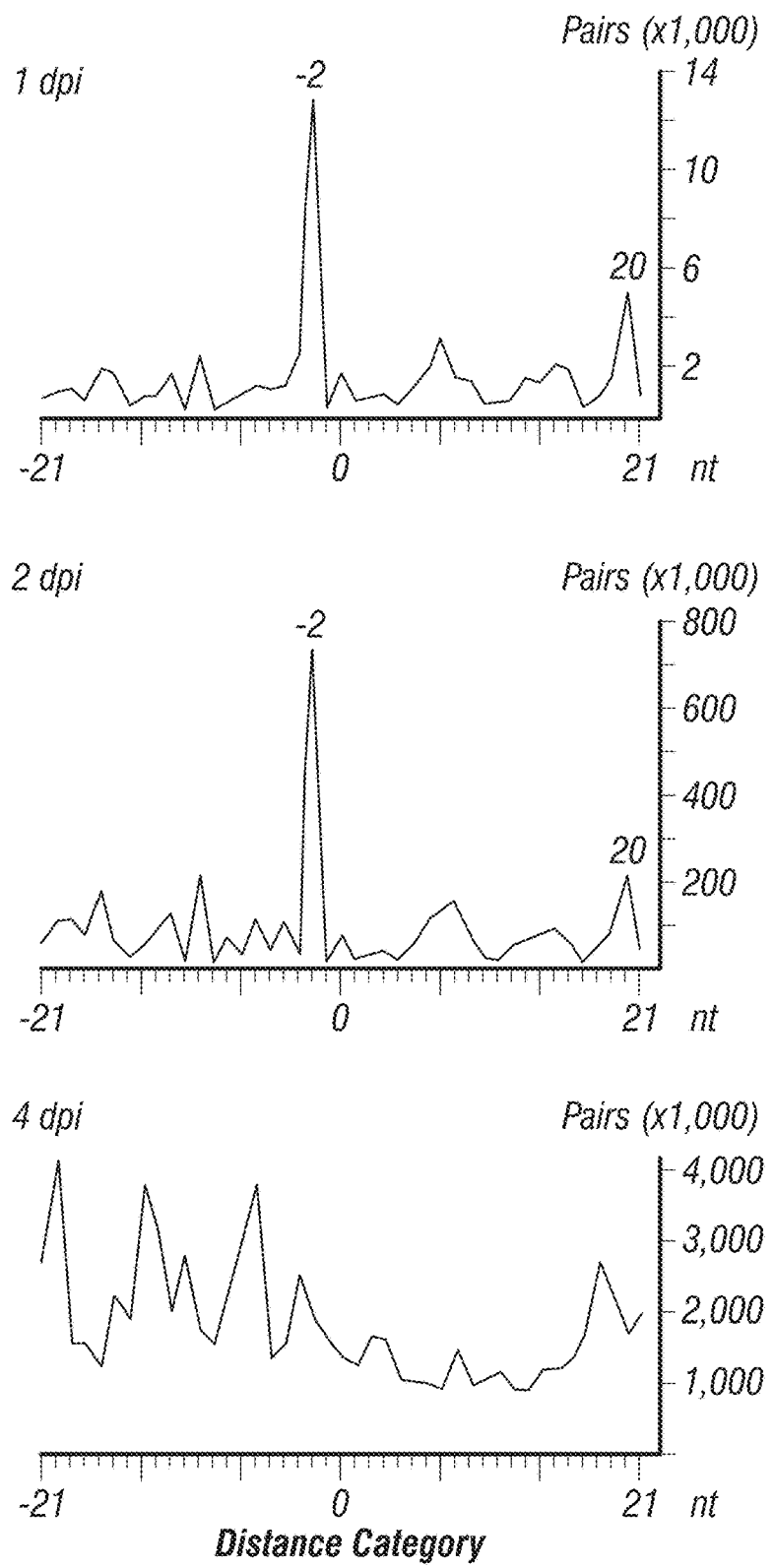

The virus accumulation in mice was determined by quantitative PCR using iScript™ Select cDNA Synthesis Kit and iQ SYBR green Supermix (Bio-Rad, Richmond, Calif.) using the extracted RNA samples described above. One μg of total RNA from individual fore or hind limb tissue of each inoculated mouse was used for cDNAs synthesis and ⅟₁₀₀ of the cDNA products obtained were used for real-time PCR using NoV Replicase_Fwd and NoV Replicase_Rev primers to amplify nucleotides 595-732 of NoV RNA-1. The relative abundance of the viral RNA-1 was normalized to β-actin mRNA as the internal control and was estimated by the ΔCT method as described in Han et al. Five µg of total RNAs from cell culture or mouse tissues were used for the detection of the positive-strand viral genomic and subgenomic RNAs by Northern blot hybridization as described in Han et al. Northern blot detection of the viral siRNAs using 20 µg of total RNAs from each mouse tissue sample and chemical cross-linking was also as described in Han et al. with one modification. The probe used was a mixture of four $^{32}$P-labeled synthetic locked nucleic acid (LNA) oligonucleotides purchased from Exiqon (Woburn, Mass.) as described in Kurreck et al. (*Nucleic Acids Res.* 30:1911-1918 (2002)). These LNA probes corresponded to nucleotides 1-50, 2754-2797 and 3151-3198 of NoV RNA-1 and to nucleotides 1-42 of NoV RNA2 and therefore were specific for the detection of the negative strand targeting these regions. See FIG. 6B for the location of these LNA probes and the hot spots of viral siRNAs.

mESCS and *Arabidopsis thaliana* RNA Analyses:

Total RNA from mESCs and from 3 weeks-old seedlings of *Arabidopsis thaliana* SUC:SUL line (ecotype Col-0) were extracted and purified using Isol-RNA Lysis Reagent (5PRIME) according to manufacturer's instructions. For Northern blot analysis of low molecular weight (LMW) RNA, total RNA was fractionated and LMW RNA isolated as described in Jay et al. (*Methods* 63:85-92 (2013)). The yield was determined using a spectrophotometer and equal amounts of LMW RNA (2-10 µg) were resolved on denaturing 17.5% polyacrylamide/urea gels, transferred on a Hybond™-NX membrane (GE Healthcare) and chemically cross-linked using 1-ethyl-3-(3-dimethylaminopropyl) carbodiimide (EDC) as described in Pall et al. (*Nat. Protoc.* 3:1077-1084 (2008)). For Northern blot analysis of high molecular weight (HMW) RNA, 5 µg of total RNA was resolved on denaturing 1.2% agarose gels with 2.2 M formaldehyde, capillary transferred to Hybond™-NX membrane (GE Healthcare) and cross-linked by UV irradiation. Equal loading was verified before transfer by ethidium bromide staining of total RNA within the RNA gel. Perfect-Hyb buffer (Sigma) was used for the hybridization step in both LMW and HMW Northern blot. DNA oligonucleotides complementary to miR-16 or U6 and locked nucleic acid (LNA™, Exiqon) complementary to EMCV (+) viRNAs were 5' end-labeled with [γ$^{32}$P]ATP using T4 Polynucleotide Kinase (Thermo Scientific). The probe used to detect SUL siRNAs was made by random priming in the presence of α-$^{32}$P-dCTP (Hartmann Analytic) using the Prime-a-gene kit (Promega). The template used for this random priming reaction was a 400-bp long PCR product amplified from *Arabidopsis* genomic DNA (ecotype Col-0) using SUL_Fwd and SUL_Rev primers (see TABLE 2). All probes used for Northern blot in this study are listed in TABLE 2.

TABLE 2

Primer Sequence

| Description | sequence 5' to 3' |
|---|---|
| Probes for Northern analysis | |
| miR-16 | GCCAATATTTACGTGCTGCTA (SEQ ID NO: 3) |
| U6 | GCAGGGGCCATGCTAATCTTCTCTGTATCG (SEQ ID NO: 4) |
| EMCV (+) viRNA | TATCGAGCAGACTGGCAATCCG (LNA ™ probe from Exiqon) (SEQ ID NO: 5) |
| NoV RNA1 and RAN3 | ATCGTTGCTTGCGTCTCCTGAGCCAGCTGCTCCAGCTTGG (SEQ ID NO: 6) |
| NoV Replicase_Fwd | CCGTTCATGGCTTACACCTT (SEQ ID NO: 7) |
| NoV Replicase_Rev | GCACCAGTCCCAAACTTCAT (SEQ ID NO: 8) |
| SUL_Fwd | ATATCGAAAAGGCTTTGACAGAAG (SEQ ID NO: 9) |
| SUL_Rev | AATCTGGTCTTGAAGCTTGTCC (SEQ ID NO: 10) |
| Primers for qRT-PCR on viral RNA and cellular mRNA | |
| Nov_AAF9_1 RNA1_Fwd | CCGTTCATGGCTTACACCTT (SEQ ID NO: 11) |
| Nov_AAF9_1 RNA1_Rev | GCACCAGTCCCAAACTTCAT (SEQ ID NO: 12) |
| Nov_AAF9_2 RNA1_Fwd | CCCAAGATGTCAAGGACGTT (SEQ ID NO: 13) |
| Nov_AAF9_2 RNA1_Rev | TCATTATCCCGGTTGATGGT (SEQ ID NO: 14) |
| Nov_AF17_1 RNA2_Fwd | CAGAGAATGGCAGCAACAAA (SEQ ID NO: 15) |
| Nov_AF17_1 RNA2_Rev | CGGTAAAACGAGACCCTGAA (SEQ ID NO: 16) |
| Nov_AF17_2 RNA2_Fwd | TTGAATTTCCAGGGTTCGAC (SEQ ID NO: 17) |
| Nov_AF17_2 RNA2_Rev | TGACCCAGCAAATTGCATTA (SEQ ID NO: 18) |
| Actin_Fwd | ATTGGCAACGAGCGGTTCC (SEQ ID NO: 19) |
| Actin_Rev | AGCACTGTGTTGGCATAGAGG (SEQ ID NO: 20) |
| EMCV 2A_Fwd | AGGCGGTTCTAAGAGCAGAACCAT (SEQ ID NO: 21) |
| EMCV 2A_Rev | AGTGGGCATTGAAGATCCGGTACA (SEQ ID NO: 22) |
| EMCV VP3_Fwd | CCATGCAGGCGACTTATGCGATTT (SEQ ID NO: 23) |
| EMCV VP3_Rev | TAACCCAGCCATCCGCATTAGTGA (SEQ ID NO: 24) |
| EMCV 5'UTR_Fwd | TTGAAAGCCGGGGGTGGGAGATCC (SEQ ID NO: 25) |
| EMCV 5'UTR_Rev | GTTTGTTGTTGTTTGGGGTGGC (SEQ ID NO: 26) |
| NoV Replicase_Fwd | CCGTTCATGGCTTACACCTT (SEQ ID NO: 27) |
| NoV Replicase_Fwd | GCACCAGTCCCAAACTTCAT (SEQ ID NO: 28) |
| NoV Capsid_Fwd | CAGAGAATGGCAGCAACAAA (SEQ ID NO: 29) |
| NoV Capsid_Rev | CGGTAAAACGAGACCCTGAA (SEQ ID NO: 30) |
| Rrm2_Fwd | CCGAGTCGGAAAGTAAAGCG (SEQ ID NO: 31) |
| Rrm2_Rev | ATGGGAAAGACAACGAAGCG (SEQ ID NO: 32) |
| Btg2_Fwd | GCGAGCAGAGACTCAAGGTT (SEQ ID NO: 33) |
| Btg2_Rev | TAGCCAGAACCTTTGGATGG (SEQ ID NO: 34) |
| Pou5f1_Fwd (Oct4) | CAACTCCCGAGGAGTCCCA (SEQ ID NO: 35) |
| Pou5f1_Rev (Oct4) | CTGGGTGTACCCCAAGGTGA (SEQ ID NO: 36) |

TABLE 2-continued

Primer Sequence

| Description | sequence 5' to 3' |
|---|---|
| Nanog_Fwd | CAGAAAAACCAGTGGTTGAAGACTAG (SEQ ID NO: 37) |
| Nanog_Rev | GCAATGGATGCTGGGATACTC (SEQ ID NO: 38) |
| Fgf5_Fwd | TGTACTGCAGAGTGGGCATC (SEQ ID NO: 39) |
| Fgf5_Rev | ACAATCCCCTGAGACACAGC (SEQ ID NO: 40) |

Primers for qRT-PCR on miRNAs and U6 snRNA

| U6 | Hs_RNU6-2_1 (Qiagen) (SEQ ID NO: 41) |
|---|---|
| miR-295 | AAAGUGCUACUACUUUUGAGUCU (SEQ ID NO: 42) |
| miR-21 | UAGCUUAUCAGACUGAUGUUGA (SEQ ID NO: 43) |

Primers for genotyping

| DICER 460 R | GTACGTCTACAATTGTCTATG (SEQ ID NO: 44) |
|---|---|
| DICER 23 F | ATTGTTACCAGCGCTTAGAATTCC (SEQ ID NO: 45) |
| DICER 458 F | TCGGAATAGGAACTTCGTTAAAC (SEQ ID NO: 46) |

Quantitative Real-Time PCR.

For mice studies with Nov, NoVΔB2 and NoVmB2: 1 μg total RNA from infected mice was used as a template for cDNAs synthesis using iScript™ Select cDNA Synthesis Kit (Bio-Rad, Richmond, Calif.). 1/100 of the cDNA product was used as template for PCR analysis using gene-specific primers as listed below. Real-time quantitative PCRs was carried out in the presence of iQ SYBR green Supermix (Bio-Rad, Richmond, Calif.). The relative abundance of selected RNAs was normalized to an internal control (β-actin). Relative abundance was estimated by the ΔCT method.

For mESCs: Real-time PCR was performed as described in Ciuado et al. (*Methods* 63:85-92 (2013)). Briefly, Real-time PCR reagents for miRNAs and control U6 snRNA were from Qiagen. For RT reactions, 1 μg total RNA was reverse transcribed using the miScript Reverse Transcription Kit (Qiagen) following the manufacturer's instructions. Following the RT reactions, cDNA products were diluted five times in distilled water, and 2 μL of the diluted cDNAs was used for PCR using QuantiTect SYBR Green PCR Master Mix and miScript Universal Primer (Qiagen). PCR reactions were conducted at 95° C. for 10 min, followed by 40 cycles at 95° C. for 15 s and 60° C. for 30 s on a LightCycler 480 real-time PCR machine (Roche). Real-time PCR for mRNAs was performed as described in Bourdet et al. (*PLoS Genet.* 2:e94 (2006)) using the Rrm2 as a reporter gene. Differences between samples and controls were calculated based on the 2-ΔCT method. Each Real-time PCR reaction was carried out in triplicates using samples from two independent cultures of all mESCs. All the primers used in this study are listed on TABLE 2.

qPCR Arrays.

The pathway-focused Mouse Antiviral Response RT$^2$ Profiler™ PCR Array from QIAGEN (Valencia, Calif.) was used to compare the innate immune responses in suckling mice after infection with NoV or NoVΔB2 according to the manufacturer's protocol. The array contained qPCR primers for 84 key genes involved in the innate immunity initiated by Toll-like, Nod-like and RIG-like immune receptors plus 5 housekeeping genes as internal controls. Briefly, 1 μg of total RNA isolated from littermate mice 4 days post inoculation with buffer, NoV or NoVΔB2 was used for cDNA synthesis using iScript™ Select cDNA Synthesis Kit (Bio-Rad, Richmond, Calif.). Equal amount of cDNA was mixed with iQ SYBR green Supermix (Bio-Rad, Richmond, Calif.) before transferring to the 96-well PCR array plate containing the pre-dispensed gene specific primer sets. Thermal cycling on the CFX96 instrument (Bio-Rad, Richmond, Calif.) and analysis of the PCR array gene expression data 3 (http://www]///[sabiosciences.com/perarraydataanalysis.php) were carried out according to manufacturer's instruction.

Cell Lysates and Immunoprecipitations.

mESCs were scraped in cell lysis buffer (25 mM Tris, pH 7.9, 250 mM KCl, 0.2 mM EDTA, 20% glycerol supplemented with Protease Inhibitor Cocktail (Complete, Roche). Cells were lysed 10 min on ice, sonicated, and centrifuged (10,000 rpm, 10 min at 4° C.) before Western blot or immunoprecipitation (IP). For E14-FHA-hAgo2, lysates were incubated at 4° C. with 20 μL of anti-FLAG-magnetic-beads (Invitrogen) for 12 h. For IP of the endogenous mAGO2, E14 lysates were incubated at 4° C. with 20 μL of G-agarose beads (Invitrogen) for 2 h and then overnight with 1/10 rat anti-mouse Ago2 antibody (clone 6F4). The next day, lysates were incubated again at 4° C. with 20 μL of G-agarose-beads (Invitrogen) for 2 h. Beads were collected by centrifugation (2000 rpm, 1 min). For IP of E14-FHA-hAGO2, at least three washes in 1 mL lysis buffer were performed and beads incubated with 100 μL 0.1 M glycine pH 2.5 for 10 min RT on a shaker. Ten μL 1 M Tris-HCl pH 8 was added to neutralize the elution buffer. Immunoprecipitated RNAs have been extracted from eluted proteins with Isol-RNA Lysis Reagent (5PRIME). For the IP of endogenous mAGO2, beads were washed three times, resuspended in 1 mL Isol-RNA Lysis Reagent (5PRIME). RNA was isolated following manufacturer's instructions and proteins were precipitated from the phenol phase by addition of 5 volume of ice-cold acetone and incubated at −20° C. overnight. After 15 min centrifugation at 13 500 rpm at 4° C., the precipitate was washed with ice-cold 80% acetone and resuspended in a buffer containing 3% [v/v] SDS, 62.3 mM Tris-HCl pH 8, 10% [v/v] glycerol.

Western Blot Analysis:

Western blot analysis was performed as described in Li et al. (*J. Biol. Chem.* 283:23397-23409 (2008)) with minor modifications. The muscle tissue of suckling mice were used for both protein and RNA extraction with Trizol following the supplier's recommended protocol and proteins part from each sample was used for Western blot analysis. Following SDS PAGE and transfer to nitrocellulose membranes (Bio-Rad, Richmond, Calif.) and blocking with Tris-buffered saline containing 0.1% Tween-20 and 5% skim milk for 1 hour at room temperature.

Alternatively, total proteins were extracted in a radioimmune precipitation assay (RIPA) buffer (Phosphate Buffered-Saline (PBS) with 1% NP-40, 0.5% sodium deoxycholate and 0.1% SDS) supplemented with Protease Inhibitor Cocktail (Complete, Roche). Proteins were quantified using the Bio-Rad DC Protein assay kit and equal amounts of protein were resolved on a Tris-glycine SDS-Polyacrylamide gel, transferred by electroblotting onto Inmobilon-P PVDF membrane (Millipore) and incubated with antibodies in PBS with 0.2% Tween-20 and 5% non-fat dried milk following standard Western blot procedures. After incubation with HRP-conjugated secondary antibody, signal was revealed by using the ECL Western Blotting Detection Kit (GE Healthcare) or by using an HRP-conjugated anti-rabbit IgG secondary antibody (Thermo Fisher Scientific, Rockford, Ill.) with an enhanced chemiluminescence reagent (Amersham Biosciences, Piscataway, N.J.).

NoV B2 protein was detected by probing the membranes overnight at 4° C. with rabbit polyclonal antibodies to NoV B2 protein. The capsid protein VP1 from EMCV was detected using the mouse monoclonal anti-VP1 antibody. The endogenous mouse AGO2 and OCT4 proteins were detected using the rat anti-mouse Ago2 (clone 6F4) and the rabbit anti-Oct4 (ab19857, Abcam, Cambridge, UK) antibodies, respectively. HA-tagged proteins were detected using peroxydase-conjugated rat monoclonal antibody (clone 3F10, Roche). Actin protein was used as a protein loading control and was detected by using an anti-actin mouse monoclonal antibody (Chemicon or Cell Signaling Technology, Beverly, Mass.). Alternatively, equal loading was verified by Coomassie staining of the membrane after Western blotting.

Deep-Sequencing and siRNA Analyses:

Total RNA was extracted using Isol-RNA Lysis Reagent (5PRIME) and 5 μg processed into sequencing libraries using adapted Illumina protocols for Illumina technology and sequenced by Fasteris SME (http://www]]][[[fasteris.com, Switzerland). All next-generation sequencing data have been submitted to the NCBI Gene Expression Omnibus (GEO) and are accessible with the accession number GSE43153. The ncPRO pipeline was used to filter out the reads mapping against the mouse genome and to analyze globally the quality of deep-sequencing. The reads not matching the mouse genome were mapped against the viral genomes using Bowtie with the default options: but –m 5000 and –e 50. The EMCV and two NoV genome sequences with the respective reference names, AF356822.1, NC_002690.1 and NC_002691.1, have been downloaded from the NCBI ftp repository (http://www]]][[[ncbi.nlm.nih.gov/Ftp/). For all phasing/periodicity studies, the read counts were calculated based on either: The 5'-end coordinates for the reads produced from the (+) strand and the 3'-end coordinates for the reads produced from the (–) strand; or conversely, the 3'-end coordinates for the reads produced from the (+) strand and the 5'-end coordinates for the reads produced from the (–) strand.

The radar plots represent the phasing by displaying the abundance of reads falling into each of 22 possible registers. The register abundance calculations were computed as the frequency of the modulo-22 of the coordinate of each read mapping the viral genomes. The registers and the histograms displaying the reads were generated using R-cran scripts. Auto-correlation is a well-established mathematical tool to detect repeated patterns. This method displays the correlation of a variable (here abundance of reads along the entire viral genome) against itself. Applied with an increasing lag from 1-nt to 100-nt it allowed detection of periodicity (phasing) in the reads mapping the viral genomes even when the 5' end peaks of 21-to-23-nt reads were omitted form the data set. P-values were calculated using a Pearson correlation test. The harmonic model signal reconstruction is based on a singular spectrum analysis used classically for signal periodicity analysis or forecasting in climatology. This methodology was applied by considering the abundance of reads along the viral genome as a signal. After a first step of signal decomposition on the first 300-nt in eigenvectors using a window parameter set at 110-nt for EMCV and NoV, a model signal was reconstructed for each strand using the 10 best eigenvectors i.e. the best contributors to the total variance. This allowed noise removal and reconstruction of the signal fitting the main trends of the raw data. For enhanced clarity, the model signal levels were multiplied by five. The auto-correlation was calculated considering only the 21-to-23 nt reads whereas the singular spectrum analysis included all reads. The auto-correlation and the singular spectrum analyses were conducted with the Rssa package in R.

In Vitro Identification of Mammalian Viral siRNAs:

Using the methods above, the disclosure detected predominantly 22-nt viral siRNAs during mammalian RNA virus infection in cell culture and mice. Nodamura virus (NoV) is mosquito-transmissible, highly virulent to suckling mice and suckling hamsters, and belongs to the same bipartite positive strand RNA virus genus as Flock house virus (FHV), an insect pathogen. FHV dsRNA replication intermediates produced in the infected fly cells are processed by Dicer-2 into predominantly 21-nt siRNAs; these viral siRNAs subsequently direct potent antiviral defense by an RNAi pathway involving R2D2 and Argonaute-2 so that RNAi suppression by B2 is essential for FHV infection in both cell culture and adult flies. Notably, the arrest of infection with a B2-deficient mutant of FHV in insect cell culture is associated with abundant accumulation of viral siRNAs because of lack of the inhibition of viral siRNA biogenesis by B2. The B2 protein of NoV exhibits similar VSR activities both in vitro and in insect cells and suppresses artificially induced RNAi in mammalian cells. Accordingly, the use of a similar B2-deletion mutant of NoV to challenge cultured mammalian cells might facilitate detection of mammalian viral siRNAs.

Using this strategy 18- to 32-nucleotide small RNAs from baby hamster kidney 21 cells (BHK-21) were detected 2 and 3 days after inoculation with virions of NoV or a NoV mutant, NoVΔB2. NoV B2 contained 3 point mutations introduced into RNA1 of NoV to prevent B2 expression without altering the amino acid sequence of the viral RNA-dependent RNA polymerase encoded in the −1 reading frame of B2. Deep sequencing yielded 9.7 to 19.1 million reads 18 to 32 nucleotides in length in the individual four small RNA libraries. 20% to 38% of the reads in each library corresponded to cellular miRNAs conserved in humans and other mammalian species, including hamsters. As is known for Dicer-dependent mammalian miRNAs, the hamster miRNAs were predominantly 22 nucleotides in length in all of the four libraries. 24.48% and 26.76% of the reads recovered were of NoV origin in BHK-21 cells 2 and 3 days after infection with NoV, respectively.

In two independent experiments, deep sequencing profiles were compared of 18- to 28-nt small RNAs from BHK-21 cells 2 or 3 days postinoculation (dpi) with either NoV or NoVΔB2. In cells infected by NoV, vsRNAs were highly abundant, but they displayed an overwhelming bias for positive strands (~97%), showed no size preference expected for Dicer products. Their abundance inversely correlated with size (see FIG. 1A and TABLE 3), and are likely breakdown products from the abundant positive-strand viral RNAs.

TABLE 3

Profiles of mammalian virus-derived small RNAs

Small RNAs from materials infected with NoV

|  | BHK-21 Cells (2 dpi) | BHK-21 Cells (3 dpi) | Suckling mice (4 dpi) |
| --- | --- | --- | --- |
| Total reads | 10,892,126 | 17,461,069 | 13,715,643 |
| NoV reads[1] | 2,479,591 (22.8%) | 4,338,911 (24.9%) | 1,998,876 (14.6%) |
| Positive-strand | 2,409,046 (97.1%) | 4,213,052 (97.1%) | 1,683,734 (84.2%) |
| Negative-strand | 70,545 (2.9%) | 125,859 (2.9%) | 315,142 (15.8%) |
| Cellular miRNAs | 4,015,778 (36.9%) | 6,681,547 (38.3%) | 2,128,066 (15.5%) |
| Other reads | 4,396,757 (40.4%) | 6,440,611 (36.9%) | 9,588,701 (69.9%) |

Small RNAs from materials infected with NoVΔB2

|  | BHK-21 Cells (2 dpi) | BHK-21 Cells (3 dpi) | Suckling mice (1 dpi) | Suckling mice (2 dpi) |
| --- | --- | --- | --- | --- |
| Total reads | 16,424,313 | 9,205,304 | 13,728,046 | 14,882,576 |
| NoVΔB2 reads[1] | 12,622 (0.1%) | 12,049 (0.1%) | 14,664 (0.1%) | 39,906 (0.3%) |
| Positive-strand | 10,772 (85.3%) | 10,122 (84.0%) | 12,138 (82.8%) | 20,678 (51.8%) |
| Negative-strand | 1,850 (14.7%) | 1,927 (16.0%) | 2,526 (17.2%) | 19,228 (48.2%) |
| 22-nt reads[2] | 2,242 | 2,156 | 3,807 | 22,191 |
| −2 population | 636 (28.4%) | 682 (31.6%) | 1,452 (38.1%) | 14,522 (65.4%) |
| +20 population | 751 (33.5%) | 769 (35.7%) | 1,090 (28.6%) | 11,232 (50.6%) |
| Cellular miRNAs | 3,368,644 (20.5%) | 3,368,644 (20.5%) | 3,368,644 (20.5%) | 5,086,428 (34.2%) |
| Other reads | 13,043,047 (79.4%) | 5,485,106 (59.6%) | 8,771,553 (63.9%) | 9,756,242 (65.6%) |

[1] The % of virus reads (with 100% identity/complementarity to viral genomic RNAs 1 and 2) in the total qualified reads of a library, and the % of positive- and negative-strand virus reads in the total virus reads of a library were given in brackets.
[2] Two mutually non-exclusive populations were detected in the total 22-nt virus reads in each library: "−2" refers to 22-nt virus reads that are perfect base-paired duplexes with 2-nt overhang at the 3' end of each strand; "+20" refers to immediately successive 22-nt virus reads according to their mapping positions in the viral genome. The % of each population in the total virus reads were given in brackets.

By contrast, vsRNAs from NoVΔB2-infected cells were much less abundant and exhibited reduced positive-strand bias (~85%) (see TABLE 3). Notably, ~77% of the total negative-strand vsRNA reads in both libraries were in the 21- to 23-nt size range with a major 22-nt peak, similar to Dicer dependent cellular microRNAs (see FIG. 1A and FIG. 2A). The unique negative-strand vsRNAs also had a dominant 22-nt peak (see FIG. 2B). Therefore, NoVΔB2 vsRNAs display patterns of length distribution and strand bias expected for Dicer products as found for plant and invertebrate viral siRNAs.

Figure 2A:
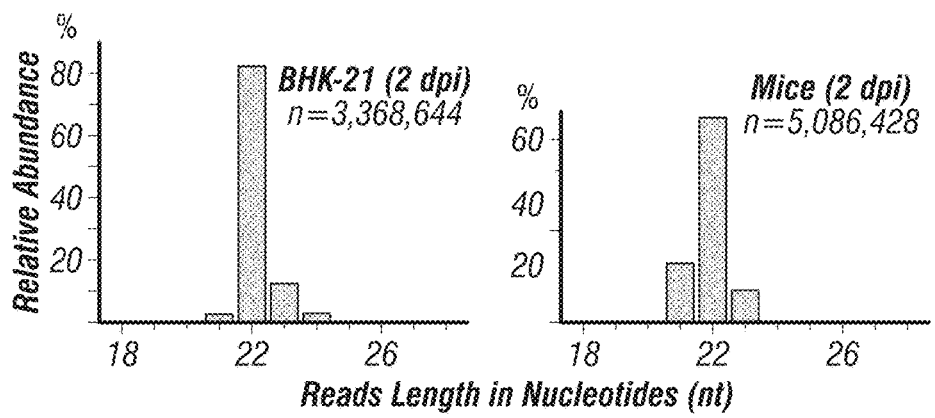
FIG. 2A-C presents profiles of cellular miRNAs and virus-derived small RNAs (vsRNAs) in BHK-21 cells infected with NoV or NoVΔB2 or mice infected with NoVΔB2. (A) Percentage of different-length mature miR-NAs from BHK-21 cells (left) and suckling mice (right) infected with NoVΔB2. Cellular miRNAs were highly abundant in each of the seven small RNA libraries (see TABLE 3) and predominantly 22 nucleotides in length. Total number of miRNA reads in each library was given. (B) Length distribution and abundance of unique species of the positive (red) or negative (blue) strand vsRNAs from BHK-21 cells and suckling mice infected with NoVΔB2. A peak at 22-nt was also detected. (C) Total counts of pairs of unique species complementary 22-nt vsRNAs in each distance category from suckling mice 1- or 2-day post infection with NoVΔB2, showing enrichment for 22-nt duplexes with 2-nt 3' overhang (−2 population) and for successive 22-nt vsRNAs (+20 population). The distance (in nucleotides) between the 5' and 3' ends of complementary vsRNAs is 0 for perfect base-paired 22-nt vsRNAs with blunt ends, −2 for pairs with 2-nt overhang at the 3'-ends, or 20 for pairs with 20-nt overhang at the 5'-ends.
Figure 2B:
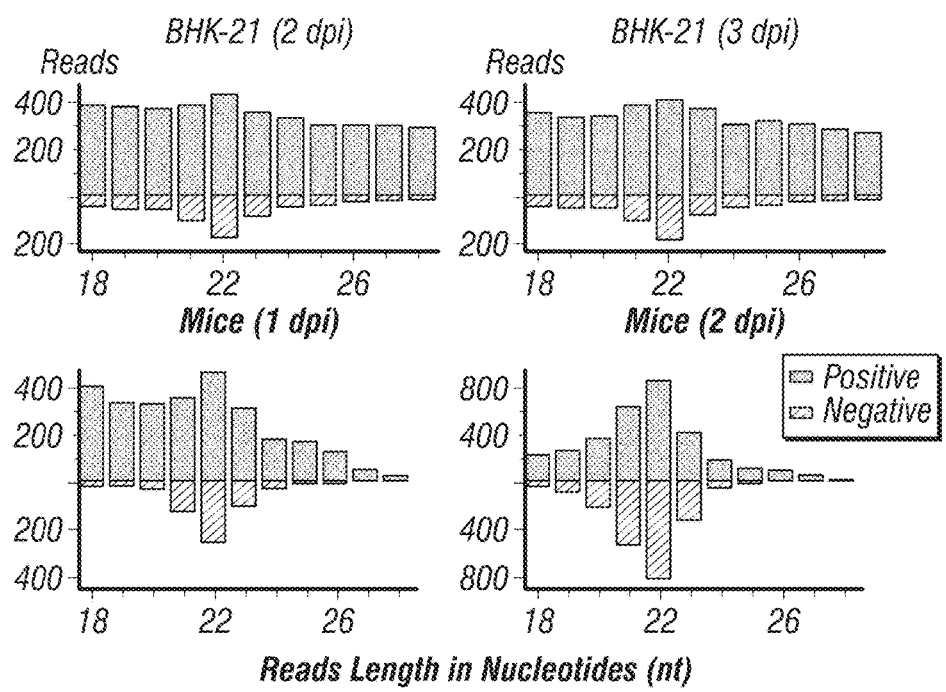
Figure 2C:
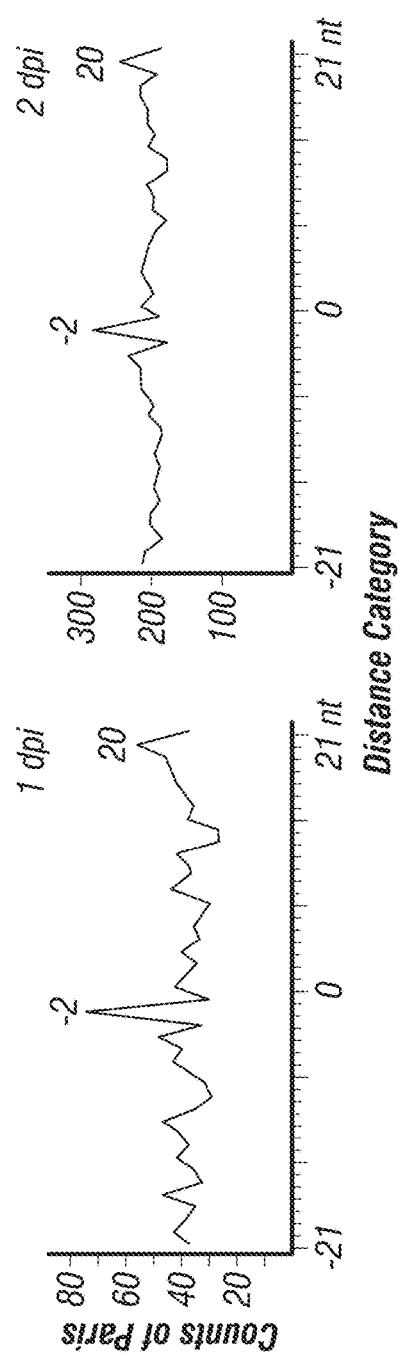

However, 97.28% and 97.24% of the vsRNAs in the two libraries corresponded to the positive-strands of NoV RNAs, the sequenced vsRNAs showed no size preference (see FIG. 1A, top). Positive-strand RNA viruses produce much higher levels of positive-strand RNAs as replication templates and mRNAs in infected cells compared to negative-strand RNAs, which act only as replication intermediates. Therefore, most of the sequenced vsRNAs may correspond to breakdown products of viral RNAs, as proposed in previous studies profiling vsRNAs from mammalian cells infected by diverse wildtype RNA viruses.

Positive- and negative-strand vsRNAs from both of the libraries constructed from NoVΔB2-inoculated BHK-21 cells had a peak at the size of 22 nucleotides (see FIG. 1A, bottom). In particular, approximately 42.5% of the total negative-strand vsRNAs in both libraries were 22 nucleotides in length with smaller peaks at 21 and 23 nucleotides (see FIG. 1A, bottom). The unique species of the negative-strand vsRNAs also had a dominant peak at 22-nt. Moreover, the relative content of the negative-strand vsRNAs (12.21% and 13.32%) in NoVΔB2-inoculated BHK21 cells was more than four folds higher than in NoV-infected BHK21 cells. The population of the negative-strand vsRNAs from NoVΔB2-infected BHK21 cells contained many reads carrying the introduced point mutations and Western blotting failed to detect expression of B2, confirming the genotype of NoVΔB2. Thus, both the sense and antisense NoVΔB2-specific vsRNAs detected in BHK-21 cells exhibited the same size preference as cellular miRNAs known to be produced by Dicer, suggesting that NoVΔB2 challenges trigger production of bona fide viral siRNAs in the mammalian host cells.

Figure 1B:
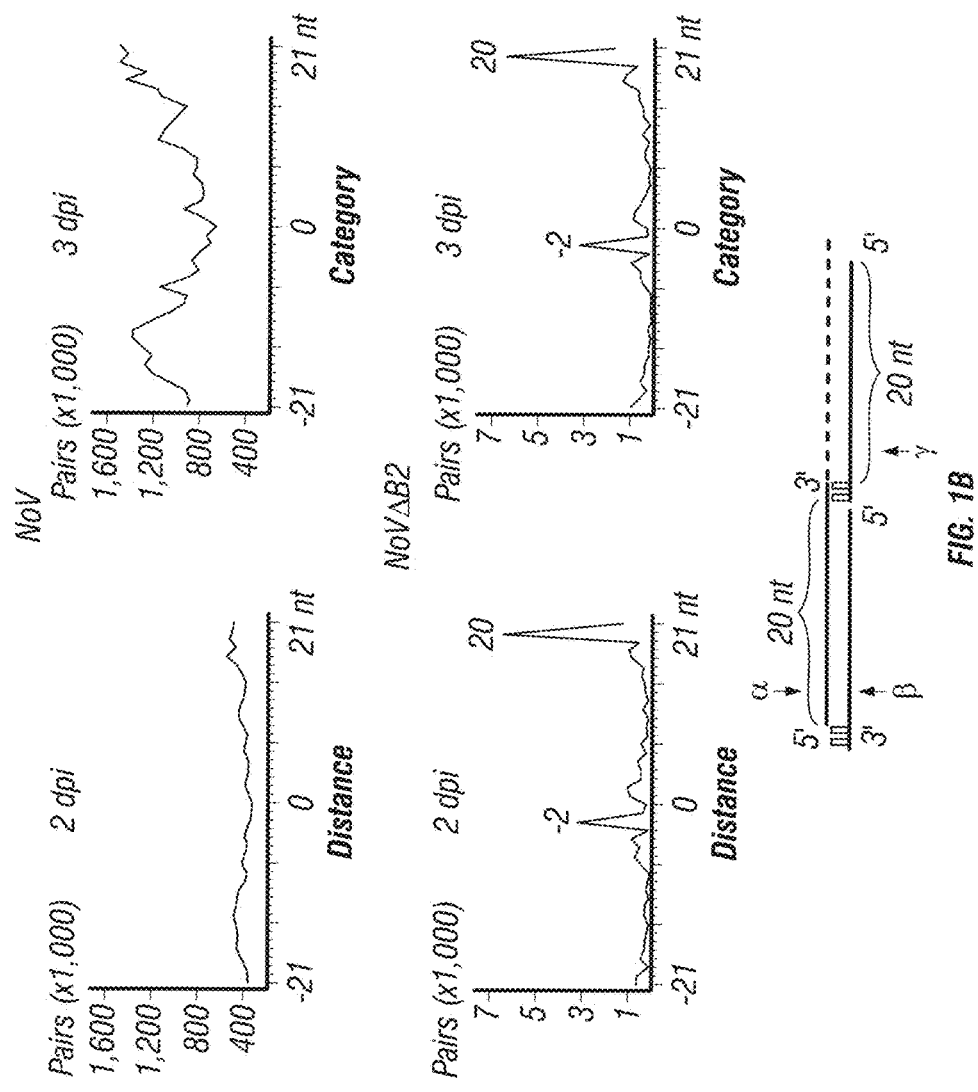

Successful cloning of NoVΔB2 vsRNAs by a protocol designed for cloning miRNAs indicated that NoVΔB2 vsRNAs contained 5' monophosphate and 3' hydroxyl terminal groups expected for the products of Dicer RNase. Unlike miRNAs that accumulate predominantly as single-stranded RNAs, however, siRNAs are short dsRNA fragments with two unpaired nucleotides at the 3' end of either strand. Therefore, the potential of the 22-nt vsRNAs of NoVΔB2 to form pairs of short duplex dsRNA with or without unpaired nucleotides at the 3' or 5'-termini of either strand were examined using a bioinformatics approach. The analysis revealed two notable features associated with the population of 22-nt vsRNAs of NoVΔB2 (see FIG. 1B). First, strong enrichment in both NoVΔB2 libraries for a population of pairs of complementary 22-nt vsRNAs with a 2-nt overhang at the 3' end (see FIG. 1B, siRNAs α and β) was observed. This finding indicates that the 22-nt vsRNAs of NoVΔB2 detected in BHK-21 cells were predominantly canonical siRNAs produced by Dicer. Second, a more dominant, unexpected population of 22-nt positive- and negative-strand viral siRNAs with 2-nt complementarity between their 3'-terminal regions (see FIG. 1B) were detected. This finding illustrates that accumulation of a given viral siRNA in NoVΔB2-challenged BHK-21 cells was frequently accompanied at the 3'-end by an immediately adjacent viral siRNA in the antisense. In contrast, vsRNAs of NoV exhibited no enrichment for either pairs of complementary vsRNAs with 2-nt 3' overhang or successive vsRNAs. These results indicate that the cloned NoVΔB2 vsRNAs exhibited properties of canonical siRNAs (see FIG. 1B and TABLE 3). First, both NoVΔB2 libraries were enriched for a population of 22-nt vsRNAs that contained a 20-nt perfectly base-paired duplex region with 2-nt 3' overhangs (see FIG. 1B, peak "−2" and siRNAs a/b). Enrichment for 22-nt canonical siRNA pairs was not found for the comparably much more abundant vsRNAs of NoV (see FIG. 1B). Second, a more dominant population of complementary 22-nt vsRNA pairs with 20-nt 5'-end overhangs only for NoVΔB2 vsRNAs was detected (see FIG. 1B, peak "20" and siRNAs a/g). These findings together suggest Dicer-dependent processing of the same viral dsRNA precursor into successive 22-nt viral siRNA duplexes in cells infected by NoVΔB2, but not by NoV.

In Vitro Studies of Comparing Wild-Type NoV and NoV Mutants on RNAi Suppression and Inducing an RNAi Response:

In contrast to the efficient infection of BHK-21 cells by B2-expressing NoV, NoVΔB2 maintained infection only at low levels (see FIG. 4A-B). Higher accumulation levels of NoVΔB2 were restored (see FIG. 4A-B), however, in BHK-21 cells engineered with a stably expressed transgene encoding either NoV B2 or Ebola virus virion protein 35 (VP35), the latter of which suppresses experimental RNAi in mammalian cells by a distinct mechanism. These results show that RNAi suppression by a cognate or heterologous VSR expressed from either the viral genome or an ectopic transgene is essential for robust virus infection in mammalian cells. It was concluded therefore that NoVΔB2 is defective only in RNAi suppression, and the RNAi response induced by NoVΔB2, characterized by the production of viral siRNAs, has potent antiviral activity in BHK-21 cells.

In Vivo Studies with Wild-Type NoV and NoV Mutants on the RNAi Response in Suckling BALB/c Mice.

Suckling BALB/c mice (6-8 days old) were intraperitoneally (i.p.) injected with NoV ΔB2 and NoV viruses. At different times post infection mice were sacrificed and the musculature of mice hind limbs and forelimbs were harvested for RNA extraction using TRIzol (Invitrogen, Carlsbad, Calif.) according to the manufacturer's protocol. The total RNAs were collected for virus detection and quantification.

Nodaviral RNA-1 replicates autonomously in absence of RNA2, which encodes the viral coat protein for virion assembly. Wild type NoV RNA-1 self-replicates to higher levels than NoV RNA-1 ΔB2 in some insect and mammalian cultures. However, a role for NoV B2 in an authentic infection of any cell types by the intact NoV has not been documented. In contrast to efficient infection of BHK-21 cells by NoV, NoVΔB2 maintained infection only at low levels (see FIG. 4, lane 4). By comparison, NoV infection of HeLa cells was much less efficient and NoVΔB2 infection was undetectable in HeLa cells. Stable ectopic expression of NoV B2 in BHK-21 cells significantly enhanced NoVΔB2 infection, but did not obviously alter NoV infection (see FIG. 4, lanes 5 and 8). Infection with the wildtype and mutant NoV strains was further examined in BHK-21 cells stably expressing Ebola virus virion protein 35 (VP35), which suppresses RNAi induced artificially in mammalian cells most likely by a mechanism distinct from that of B2. NoVΔB2 infection was also efficiently rescued in the VP35-expressing BHK-21 cells (see FIG. 4, lane 6) as found in B2-expressing cells. Therefore, suppression of RNAi by either VSR is required to establish robust virus infection in BHK-21 cells, indicating an antiviral function for RNAi in the cultured mammalian cells that produce Dicer-dependent viral siRNAs in response to virus infection.

NoV infection in vivo also requires suppression of RNAi by B2. NoV is lethal for 7-day old mice infected by intraperitoneal (IP) injection. The infection of suckling mice were compared by doses of NoV and NoVΔB2 titrated to replicate to similar levels in stable B2-expressing BHK-21 cells (see FIG. 4). Unlike lethal infection by NoV, suckling mice remained healthy (see FIG. 5C) after IP injection of NoVΔB2 for as long as observations were made (4 weeks). Quantitative RT-PCR analysis detected spread of both NoV and NoVΔB2 from the abdominal cavity to the fore and hind legs one day post inoculation (p.i.) (see FIG. 5A-B). At 1 day p.i. NoV and NoV B2 accumulated to similar levels in mice. However, although viral genomic RNAs were approximately as abundant as ribosomal RNAs in the NoV-infected mice, NoVΔB2 accumulated to at least 100-fold lower levels in the infected mice (see FIG. 5A-B). Thus, the in vivo virulence and abundant accumulation of NoV depends on the suppression of RNAi by its B2 protein, indicating an in vivo antiviral function for RNAi in mammals.

Figure 5A:
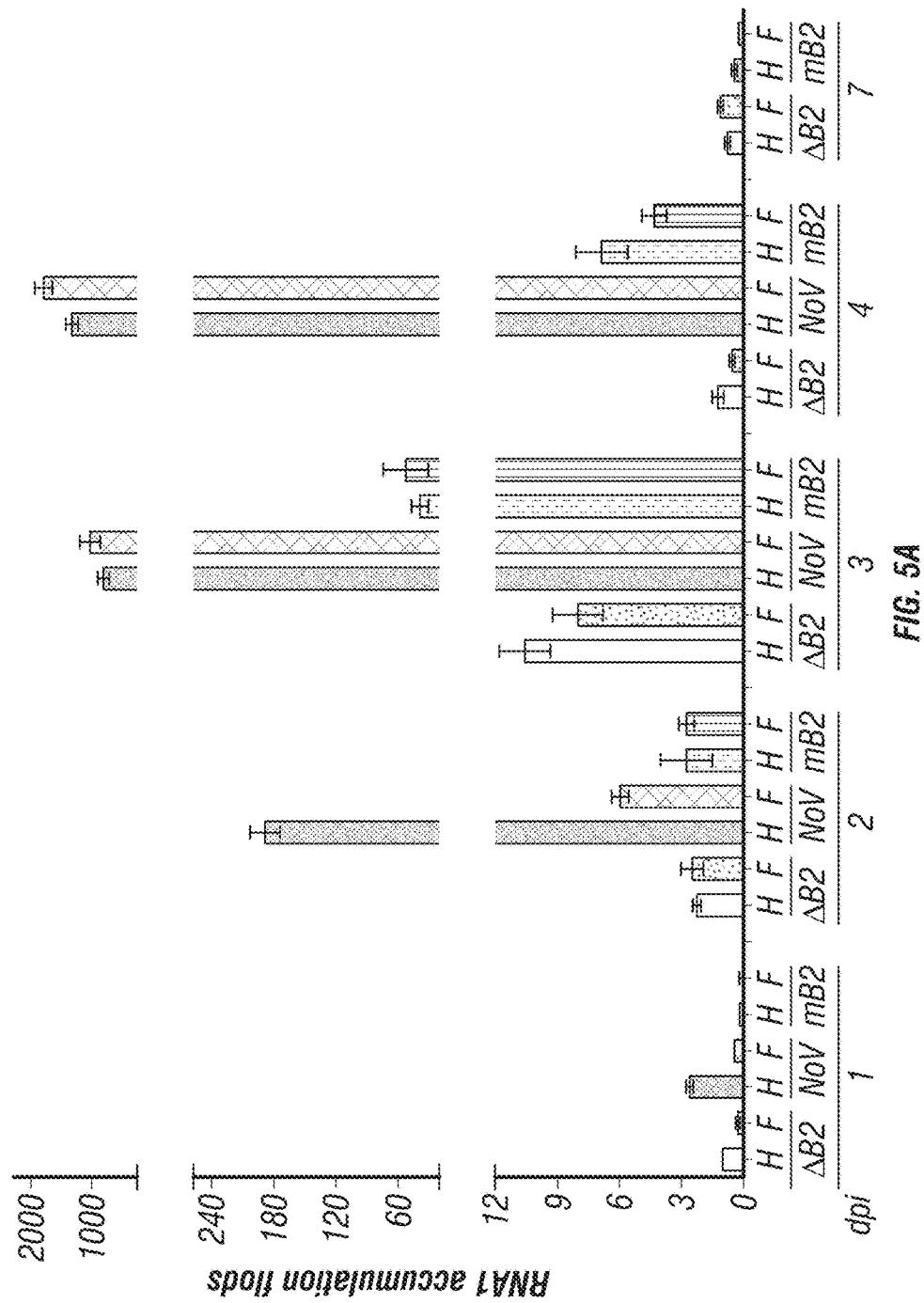
FIG. 5A-D demonstrates that in vivo virus clearance is associated with production of viral siRNAs. (A,B) Accumulation of NoV, NoVΔB2 and NoVmB2 in mouse fore (F) and hind (H) limb tissues detected by quantitative RT-PCR of the viral RNA-1 and Northern blotting, respectively. NoVΔB2 level in hind limb at 1 dpi was set as 1 and error bars indicated standard deviation of three replicates (A). NoV RNAs-1 and -2 (arrows) were visible after rRNA staining to show equal loading (B). (C) Suckling mice remained as healthy 4 weeks post-infection with either NoVΔB2 (right) or NoVmB2 (not shown) as mock-inoculated mice (left) whereas all of the five NoV-inoculated mice died by 5 dpi (not shown). (D) Northern blot detection of negative-strand viral siRNAs in mice infected with NoVΔB2 (middle panel) or NoVmB2 (left panel) and of vsRNAs from NoV-infected mice (right panel). The hybridizing positions of four siRNA probes are presented in FIG. 6B and size markers were synthetic 21- and 25-nt RNAs. The same filters were probed for mouse microRNA 127 (miR-127) and U6 RNA as loading controls. At least three independent repeats with reproducible results were performed with each experiment.
Figure 5B:
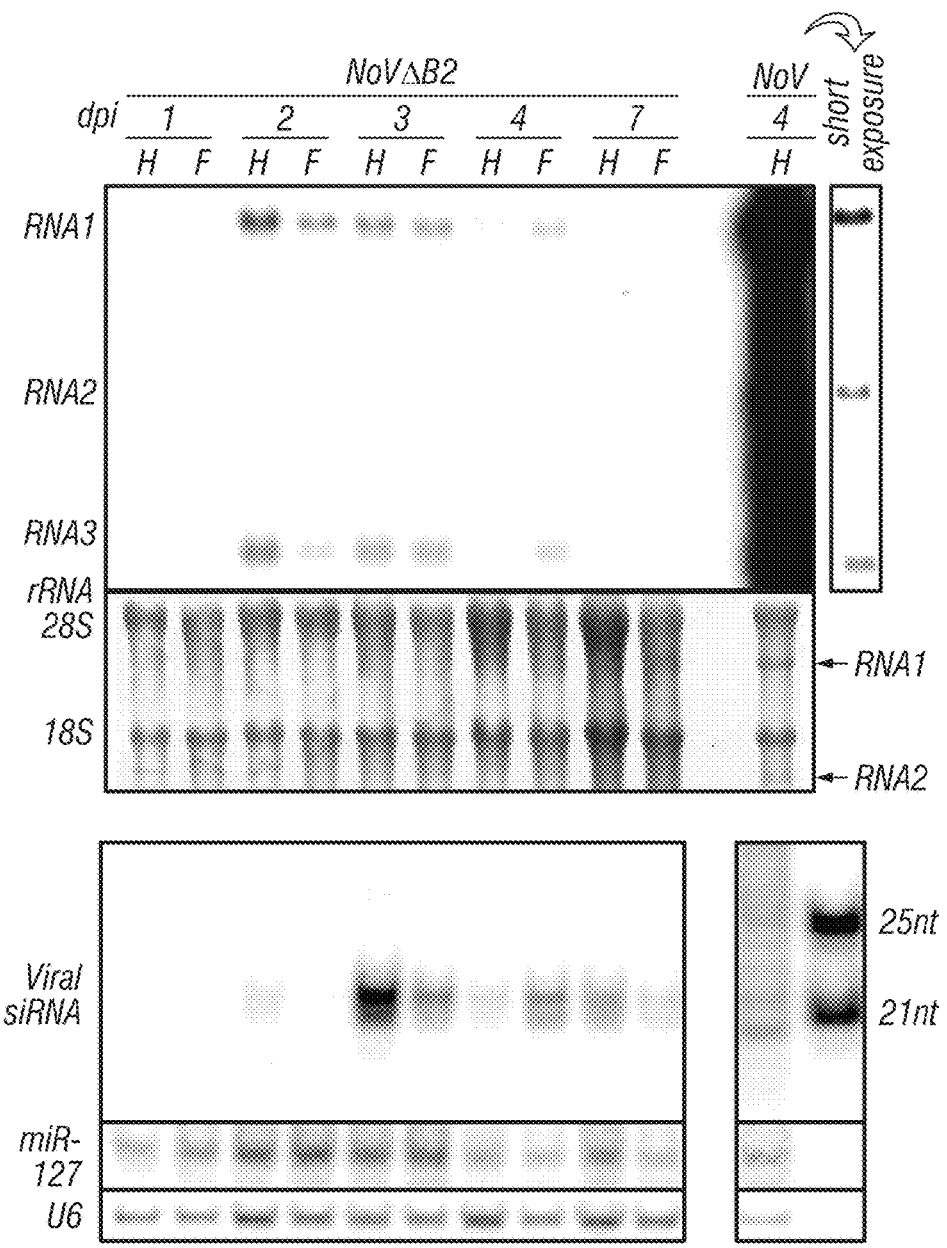
Figure 5D:
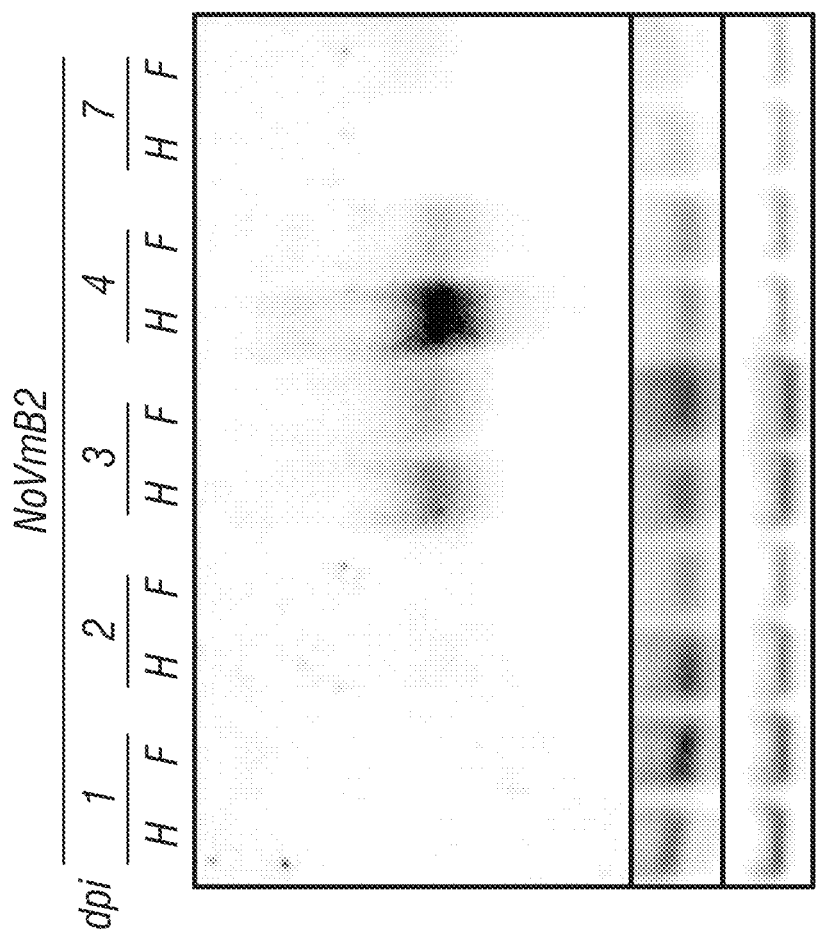
Figure 5C:
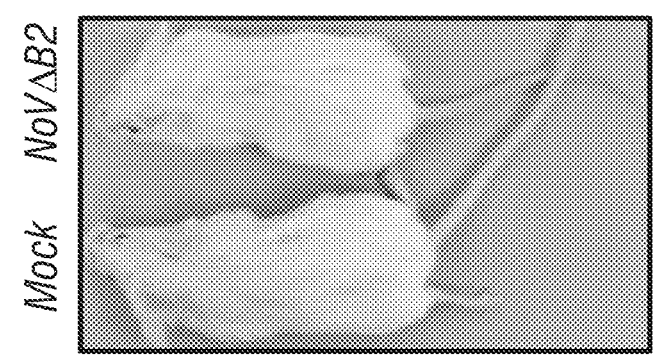

Quantitative reverse transcription polymerase chain reaction (RT-PCR) analysis validated the spread of both NoV and NoVΔB2 from the injected abdominal cavity to the fore- and hind limb tissues 24 hours after inoculation (see FIG. 5A). The difference between NoV and NoVΔB2 accumulation levels was small at 1 dpi, although higher doses of NoVΔB2 were inoculated into each mouse (supplementary materials), but became progressively more pronounced at later infection times. By 4 dpi, NoV RNA levels were comparable to those of ribosomal RNAs (rRNAs), whereas the accumulation of NoV was more than 1000 times that of NoVΔB2 (see FIG. 5A-B). Accordingly, unlike the 100% mortality observed 5 days post-NoV infection, suckling mice challenged by NoVΔB2 remained healthy for the duration of the experiment, up to 4 weeks postinoculation (see FIG. 5C). The quantitative RTPCR analysis on the expression of 84 key genes from the known innate antiviral pathways in suckling mice at 4 dpi detected no major differences between infection by NoVΔB2 and NoV (see TABLE 4).

TABLE 4

Changes in the expression levels of mouse antiviral innate immunity genes in suckling mice after infection with NoV or NoVΔB2.

| Gene symbol | RefSeq | *Fold change after NoV infection | *Fold change after NoVΔB2 infection | Gene Description |
| --- | --- | --- | --- | --- |
| Cxcl10 | NM_021274 | 29.7 | 7.3 | Chemokine (C-X-C motif) ligand 10 |
| Isg15 | NM_015783 | 22.7 | 8.8 | ISG15 ubiquitin-like modifier |
| Irf7 | NM_016850 | 13.6 | 9.4 | Interferon regulatory factor 7 |
| Cxcl9 | NM_008599 | 13.0 | 4.3 | Chemokine (C-X-C motif) ligand 9 |
| Ifih1 | NM_027835 | 10.3 | 3.5 | Interferon induced with helicase C domain 1 |
| Ccl5 | NM_013653 | 8.3 | 16.7 | Chemokine (C-C motif) ligand 5 |
| Ifnb1 | NM_010510 | 7.5 | 2.5 | Interferon beta 1, fibroblast |
| Dhx58 | NM_030150 | 6.6 | 3.6 | DEKH (Asp-Glu-K-His) box polypeptide 58 |
| Il6 | NM_031168 | 6.5 | 2.6 | Interleukin 6 |
| Stat1 | NM_009283 | 4.4 | 3.2 | Signal transducer and activator of transcription 1 |
| Mx1 | NM_010846 | 3.3 | 2.5 | Myxovirus (influenza virus) resistance 1 |
| Ddx58 | NM_172689 | 3.3 | 2.4 | DEAD (Asp-Glu-Ala-Asp) box polypeptide 58 |
| Cd40 | NM_011611 | 3.1 | 2.4 | CD40 antigen |
| Ccl4 | NM_013652 | 2.8 | 3.2 | Chemokine (C-C motif) ligand 4 |
| Trim25 | NM_009546 | 2.2 | 2.4 | Tripartite motif-containing 25 |

TABLE 4-continued

Changes in the expression levels of mouse antiviral innate immunity genes in suckling mice after infection with NoV or NoVΔB2.

| Gene symbol | RefSeq | *Fold change after NoV infection | *Fold change after NoVΔB2 infection | Gene Description |
|---|---|---|---|---|
| Tlr3 | NM_126166 | 2.2 | 1.6 | Toll-like receptor 3 |
| Ccl3 | NM_011337 | 2.1 | 2.8 | Chemokine (C-C motif) ligand 3 |
| Oas2 | NM_145227 | 1.8 | 2.4 | 2'-5' oligoadenylate synthetase 2 |
| Il15 | NM_008357 | 1.8 | 1.7 | Interleukin 15 |
| Ctss | NM_021281 | 1.7 | 1.3 | Cathepsin S |
| Nod2 | NM_145857 | 1.7 | 1.8 | Nucleotide-binding oligomerization domain containing 2 |
| Casp1 | NM_009807 | 1.6 | −1.1 | Caspase 1 |
| Nfkbia | NM_010907 | 1.5 | −1.3 | Nuclear factor of kappa light polypeptide gene enhancer in B-cells inhibitor, alpha |
| Tbkbp1 | NM_198100 | 1.4 | 2.2 | TBK1 binding protein 1 |
| Tlr9 | NM_031178 | 1.4 | 2.1 | Toll-like receptor 9 |
| Pstpip1 | NM_011193 | 1.4 | 1.4 | Proline-serine-threonine phosphatase-interacting protein 1 |
| Rela | NM_009045 | 1.3 | 1.8 | V-rel reticuloendotheliosis viral oncogene homolog A (avian) |
| Card9 | NM_001037747 | 1.3 | 1.7 | Caspase recruitment domain family, member 9 |
| Jun | NM_010591 | 1.3 | 1.0 | Jun oncogene |
| Cd86 | NM_019388 | 1.3 | −1.3 | CD86 antigen |
| Pycard | NM_023258 | 1.2 | −1.6 | PYD and CARD domain containing |
| Ctsb | NM_007798 | 1.2 | 1.3 | Cathepsin B |
| Tnf | NM_013693 | 1.2 | 2.4 | Tumor necrosis factor |
| Il1b | NM_008361 | 1.1 | 1.8 | Interleukin 1 beta |
| Myd88 | NM_010851 | 1.1 | 1.3 | Myeloid differentiation primary response gene 88 |
| Irf5 | NM_012057 | 1.1 | 1.4 | Interferon regulatory factor 5 |
| Cxcl11 | NM_019494 | 1.0 | 1.5 | Chemokine (C-X-C motif) ligand 11 |
| Cnpy3 | NM_028065 | −1.0 | 1.2 | Canopy 3 homolog (zebrafish) |
| Ctsl | NM_009984 | −1.0 | −1.2 | Cathepsin L |
| Map3k1 | NM_011945 | −1.1 | 1.0 | Mitogen-activated protein kinase kinase kinase 1 |
| Ikbkb | NM_010546 | −1.1 | 1.5 | Inhibitor of kappaB kinase beta |
| Ripk1 | NM_009068 | −1.1 | 1.3 | Receptor (TNFRSF)-interacting serine-threonine kinase 1 |
| Fadd | NM_010175 | −1.1 | 1.5 | Fas (TNFRSF6)-associated via death domain |
| Ifnar1 | NM_010508 | −1.1 | 1.3 | Interferon (alpha and beta) receptor 1 |
| Casp8 | NM_009812 | −1.1 | −1.4 | Caspase 8 |
| Pin1 | NM_023371 | −1.1 | 1.0 | Protein (peptidyl-prolyl cis/trans isomerase) NIMA interacting 1 |
| Traf3 | NM_011632 | −1.1 | 1.1 | Tnf receptor-associated factor 3 |
| Fos | NM_010234 | −1.2 | 1.3 | FBJ osteosarcoma oncogene |
| Map2k3 | NM_008928 | −1.2 | 1.2 | Mitogen-activated protein kinase kinase 3 |
| Nfkb1 | NM_008689 | −1.2 | −1.1 | Nuclear factor of kappa light polypeptide gene enhancer in B-cells 1, p105 |
| Mapk3 | NM_011952 | −1.2 | −1.0 | Mitogen-activated protein kinase 3 |
| Aim2 | NM_001013779 | −1.2 | −1.0 | Absent in melanoma 2 |
| Il18 | NM_008360 | −1.2 | −2.5 | Interleukin 18 |
| Map2k1 | NM_008927 | −1.2 | 1.5 | Mitogen-activated protein kinase kinase 1 |
| Azi2 | NM_013727 | −1.2 | −1.2 | S-azacytidine induced gene 2 |
| Mapk14 | NM_011951 | −1.2 | −1.0 | Mitogen-activated protein kinase 14 |
| Mapk1 | NM_011949 | −1.3 | −1.1 | Mitogen-activated protein kinase 1 |
| Ddx3x | NM_010028 | −1.3 | −1.2 | DEAD/H (Asp-Glu-Ala-Asp/His) box polypeptide 3, X-linked |
| Irak1 | NM_008363 | −1.3 | −1.6 | Interleukin-1 receptor-associated kinase 1 |
| Tlr8 | NM_133212 | −1.4 | 1.3 | Toll-like receptor 8 |
| Tlr7 | NM_133211 | −1.4 | 1.1 | Toll-like receptor 7 |
| Cd80 | NM_009855 | −1.4 | 1.4 | CD80 antigen |
| Hsp90aa1 | NM_010480 | −1.4 | −1.6 | Heat shock protein 90, alpha (cytosalic), class A member 1 |
| Atg5 | NM_053069 | −1.4 | −1.4 | Autophagy-related 5 (yeast) |
| Il12a | NM_008351 | −1.4 | 1.4 | Interleukin 12A |
| Sugt1 | NM_026474 | −1.5 | −1.7 | SGT1, suppressor of G2 allele of SKP1 (S. cerevisiae) |
| Irf3 | NM_016849 | −1.5 | −1.9 | Interferon regulatory factor 3 |
| Map3k7 | NM_172688 | −1.5 | −1.2 | Mitogen-activated protein kinase kinase kinase 7 |
| Cyld | NM_173369 | −1.5 | 1.0 | Cylindromatosis (turban tumor syndrome) |
| Dak | NM_145496 | −1.5 | 1.3 | Dihydroxyacetone kinase 2 homolog (yeast) |
| Tradd | NM_001033161 | −1.5 | −1.7 | TNFRSF1A-associated via death domain |
| Nlrp3 | NM_145827 | −1.5 | 1.2 | NLR family, pyrin domain containing 3 |
| Il12b | NM_008352 | −1.5 | 1.7 | Interleukin 12B |
| Chuk | NM_007700 | −1.5 | −1.8 | Conserved helix-loop-helix ubiquitous kinase |
| Tank | NM_011529 | −1.6 | −1.7 | TRAF family member-associated Nf-kappa B activator |
| Ifna2 | NM_010503 | −1.7 | 1.3 | Interferon alpha 2 |
| Traf6 | NM_009424 | −1.7 | 1.7 | Tnf receptor-associated factor 6 |
| Ticam1 | NM_174989 | −1.8 | −1.1 | Toll-like receptor adaptor molecule 1 |
| Tbk1 | NM_019786 | −1.9 | −1.6 | TANK-binding kinase 1 |
| Mavs | NM_144888 | −2.0 | 1.3 | Mitochondrial antiviral signaling protein |
| Mapk8 | NM_016700 | −2.1 | −1.3 | Mitogen-activated protein kinase 8 |
| Spp1 | NM_009263 | −2.1 | −1.6 | Secreted phosphoprotein 1 |
| Mefv | NM_019453 | −2.2 | 1.8 | Mediterranean fever |
| Atg12 | NM_026217 | −4.0 | −1.6 | Autophagy-related 12 (yeast) |

*The value shown were the average fold changes of three independent experiments after suckling mouse infection by NoV or NoVΔB2 compared to mock inoculation.

This suggested that rapid in vivo clearance of NoVΔB2 was not mediated by one of the known innate antiviral pathways. Moreover, it was found that a NoV mutant (NoVmB2) carrying a single Arg to Gln mutation at position 59 of B2, known to abolish B2's VSR activity in vitro (3, 24), was as nonvirulent as NoVΔB2 in suckling mice and was also progressively cleared from 4 dpi (see FIG. 5A). Thus, in vivo infection and virulence of NoV require the RNAi suppressor activity of B2.

Northern blot hybridization detected accumulation of discrete species of viral siRNAs in NoVDB2-inoculated suckling mice (see FIG. 5D, right panel), as found in plant and invertebrate hosts after virus infection. The mouse viral siRNAs migrated as a dominant 22-nt band alongside a weaker, 21-nt signal and became detectable at 2 dpi and remained so up to 7 dpi even through the accumulation of NoVΔB2 was low at both 2 and 7 dpi (see FIG. 5A-B). By contrast, vsRNAs from NoV-infected mice appeared as bands of heterogeneous sizes (see FIG. 5D, right panel). These results were in agreement with the deep sequencing results from NoVΔB2-inoculated BHK-21 cells (see FIG. 1A, bottom). Notably, the 22-nt viral siRNAs became readily detectable in suckling mice inoculated with NoVmB2 (see FIG. 5D, left panel). These findings indicate that the in vivo RNA-mediated defense against NoVΔB2 is associated with highly abundant accumulation of viral siRNAs.

Figure 6C:
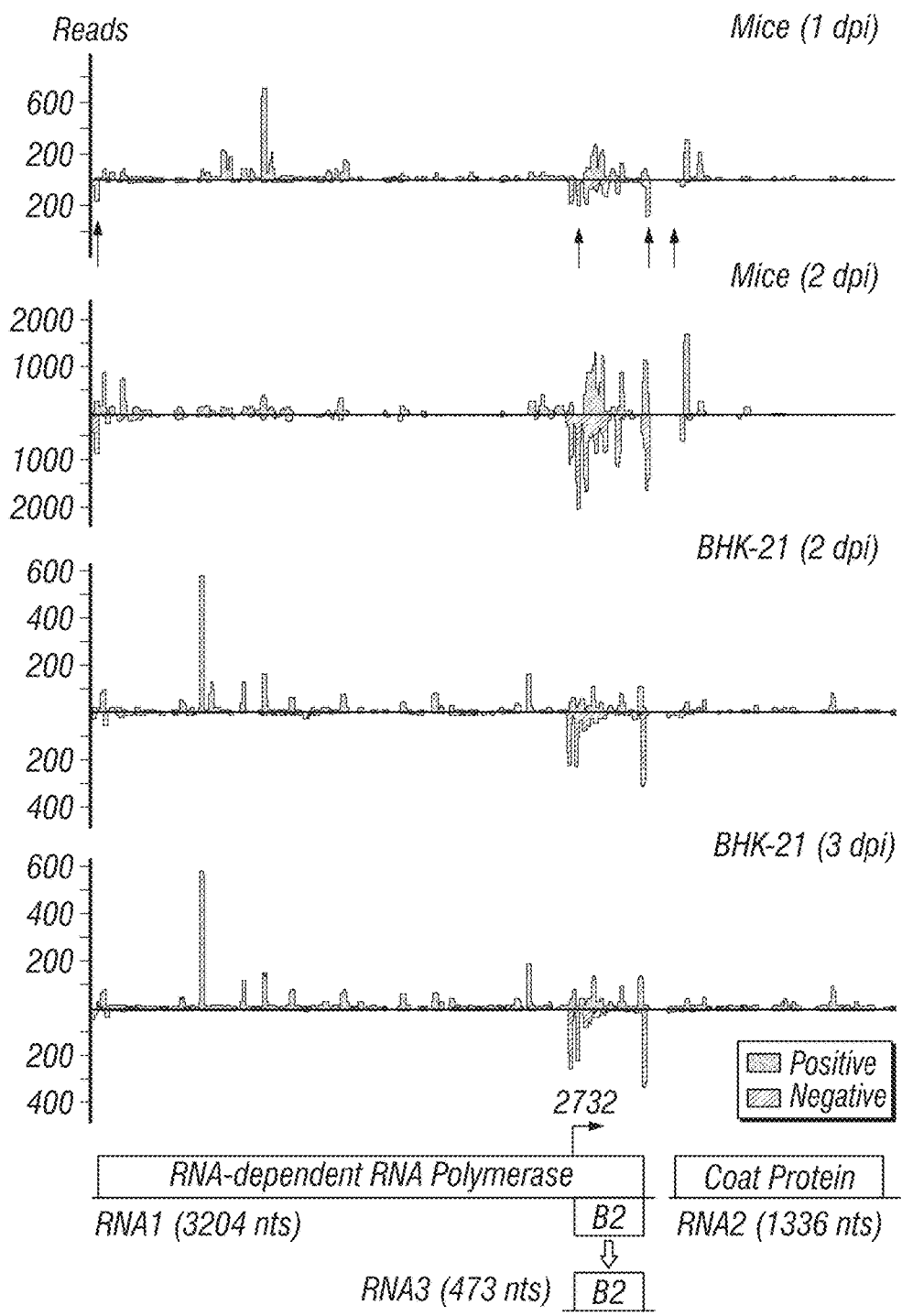

Therefore, rapid virus clearance resulting from loss of viral suppression of RNAi in NoVΔB2- and NoVmB2-infected mice was consistently accompanied with abundant production of the 22-nt viral siRNAs. The small RNAs from suckling mice 4 days after NoV inoculation and from those 1 or 2 days after NoVΔB2 inoculation were deep sequenced. NoV vsRNAs showed no size preference, and the 22-nt vsRNAs of NoV were not enriched for canonical siRNAs (see FIG. 6A-B), which suggested B2 suppression of viral siRNA biogenesis in NoV-infected mice. It was noted that NoV vsRNAs cloned from mice contained more abundant negative strands (16%) than those from cell culture (3%) (see TABLE 3), which might indicate weak in vivo dicing of NoV dsRNA in the presence of B2. By contrast, ~85% of NoVΔB2 small RNAs from mice were 21- to 23-nt long, with 22 nt as the predominant size for both strands (see FIG. 6A and FIG. 2B). A higher density of viral siRNAs was found to target the RNA-3 transcribing region of RNA-1 and the 5'-terminal region of RNAs 1 and 2 in NoVΔB2-infected mice and BHK-21 cells (see FIG. 6C). The relative abundance of viral siRNAs in NoVΔB2-infected mice (0.3%) (see TABLE 3) was similar to that found in fruit flies (0.5 to 0.9%) undergoing FHVΔB2 clearance. NoVΔB2 siRNAs from mice at 2 dpi were divided approximately equally into positive and negative strands (see FIG. 6A), and 65% of the 22-nt viral siRNAs in both NoVΔB2 libraries could form canonical siRNA duplexes with 2-nt 3' overhang (see FIG. 6B and TABLE 3). The 22-nt viral siRNAs of NoVΔB2 detected by Northern blotting therefore have the properties of canonical viral siRNAs processed from dsRNA viral replication intermediates, which demonstrates induction of a typical antiviral RNAi response in mice by NoVΔB2 infection. Together, the findings reveal that, without viral suppression of RNAi, mice are able to launch a potent antiviral RNAi response sufficiently effective to provide full protection from lethal viral infection.

Characterization of the RNAi-Mediated Antiviral Immunity in Suckling Mice:

Viral siRNAs are a central component of RNAi-mediated antiviral immunity. Viral siRNAs are both the product of the host immune detection of viral infection and the specificity determinants of the induced immunity. Thus, mapping of the sequenced viral siRNAs to the viral genome will help identify the viral dsRNA that triggers the recognition and processing by the host Dicer complex and predict the viral sequences targeted by the RISC antiviral effector complex. Experiments are performed to analyze the silencing activity of the viral siRNAs produced in vivo by the mammalian immune system and to characterize viral suppression of RNAi using NoV infection of suckling mice as a model. It should be pointed out that although RNAi is widely used in labs and clinical trials as a specific gene knockdown technology, little is known about the natural role and the biogenesis of siRNAs in mammals except for a few studies in mouse oocytes and mouse ES cells. Thus, characterization of the dominant length, preference for specific nucleotides at the termini and other properties of siRNAs produced by Dicer under physiological conditions will be beneficial for designing optimal experimental RNAi.

Figure 6D:
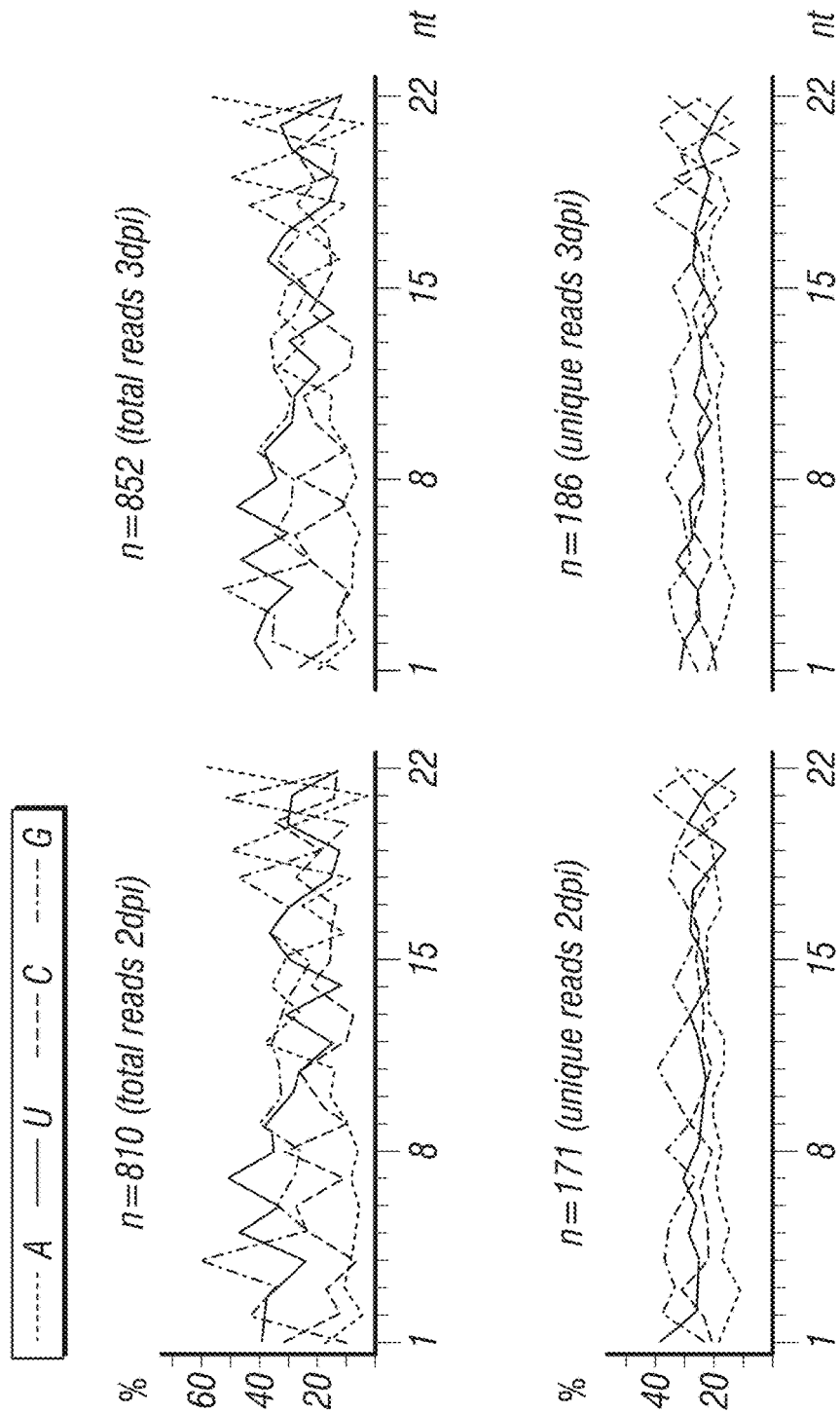

Studies with Negative-Strand Viral siRNAs and RNA-1 transcription:

Properties of the mammalian viral siRNAs were further examined by focusing on the population of the negative-strand viral siRNAs in NoVΔB2 libraries, which was less likely to contain non-specific degradation products. Similar to viral siRNA biogenesis triggered by FHVΔB2 in Drosophila. Hot spots of viral siRNAs targeting were detected in the 5'-terminal regions of the two genomic RNAs of NoVΔB2 in BHK-21 cells (see FIG. 6C). By comparison, BHK-21 cells produced lower density of viral siRNAs targeting the 5'-terminal region of RNA-1, but higher siRNA density targeting the 3'-terminal region of RNA-1 and the RNA-3 transcriptional start region of RNA-1 (see FIG. 6C), both of which were not detected in the Drosophila in response to FHVΔB2. These observations suggest differences of the insect and mammalian hosts in the recognition of distinct dsRNA intermediates produced during the synthesis of the nodaviral genomic and subgenomic RNAs. As expected, hamster miRNAs have strong uridine preference for the 5'-terminal nucleotide (see FIG. 6C). However, no nucleotide preference was detected for the 5'-terminus of the viral antisense siRNAs in any of the 21-, 22- or 23-nt classes (see FIG. 6D). Instead, strong adenine enrichment for the 3'-terminal nucleotide of the total NoVΔB2 antisense siRNAs in the 22-nt class (~58% for both libraries) was identified, but not in the 21- and 23-nt classes (FIG. 1D, top). However, the 3'-terminal adenine preference was undetectable when only the unique species of the 22-nt NoVΔB2 antisense siRNAs was considered (see FIG. 6D, bottom), suggesting a possible effect of 3' adenylation on the abundance of the mammalian viral siRNAs as observed previously for mammalian and plant miRNAs.

In was found in the experiments presented herein that an RNA virus infection in cultured hamster cells and suckling mice induces a typical antiviral RNAi response, characterized by the production of viral siRNAs with clearly defined properties of canonical siRNAs. The findings illustrate that Dicer-dependent processing of dsRNA viral replication intermediates into successive siRNAs is a conserved mammalian immune response to infection by two distinct positive strand RNA viruses (see TABLE 5). A set of identical phased viral siRNA pairs targeting the 5'-terminal region of NoVΔB2 RNA1 were detected from suckling mice and BHK-21 cells (see TABLE 5) and cloned with similar relative abundances from mouse embryonic stem cells infected by NoVΔB2. Read numbers of phased positive (+) and negative (−) strand 22-nt vsRNAs targeting the 5'-terminal region (1-180 nt) of NoVΔB2 RNA-1 cloned from suckling mice or BHK-21 cells after infection with NoVΔB2. The assemblies were identified from total vsRNAs by a Perl script, which searched for the longest set of successive 22-nt vsRNA duplexes with 2-nt 3'-overhangs with penalty assigned to each 21- or 23-nt vsRNA included in the array.

TABLE 5

Phased vsRNAs targeting the 5'-terminal region of NoVΔB2 RNA1

| Duplex no. | Mice 1 dpi (Library 5) | Mice 2 dpi (Library 6) | BHK-21 2 dpi (Library 3) | BHK-21 3 dpi (Library 4) |
|---|---|---|---|---|
| 1 (−)[1] | 38 (nt 2–23) | 375 (nt 2–23) | 26 (nt 2–23) | 47 (nt 2–23) |
| 1 (+)[2] | 2 (nt 4–25) | 14 (nt 4–25) | 9 (nt 4–25) | 11 (nt 4–25) |
| 2 (−) | 163 (nt 24–45)* | 716 (nt 24–45)* | 9 (nt 24–45)* | 13 (nt 24–45)* |
| 2 (+) | 15 (nt 26–47)* | 229 (nt 26–47)* | 3 (nt 26–47)* | 7 (nt 26–47)* |
| 3 (−) | —** | —** | —** | —** |
| 3 (+) | 7 (nt 48–70)* | 86 (nt 48–70)* | 6 (nt 48–69) | 1 (nt 49–70) |
| 4 (−) | —** | 3 (nt 69–90) | 2 (nt 69–90) | 3 (nt 69–90) |
| 4 (+) | 55 (nt 71–92)* | 735 (nt 71–92)* | 60 (nt 71–92)* | 52 (nt 71–92)* |
| 5 (−) | 6 (nt 91–112)* | 56 (nt 91–112)* | 29 (nt 91–111) | 21 (nt 91–111) |
| 5 (+) | — | 1 (nt 94–114) | — | — |
| 6 (−) | —** | —** | —** | —** |
| 6 (+) | 14 (nt 114–135)* | 67 (nt 114–135)* | 5 (nt 114–135)* | 5 (nt 114–135)* |
| 7 (−) | 2 (nt 134–155) | 4 (nt 134–155) | —** | 1 (nt 134–155) |
| 7 (+) | —** | —** | 2 (nt 136–157) | 6 (nt 136–157) |
| 8 (−) | 4 (nt 157–177)* | 42 (nt 156–177) | 5 (nt 156–177) | 3 (nt 156–177) |
| 8 (+) | 1 (nt 160–180) | 9 (nt 158–179)* | 13 (nt 158–179)* | 11 (nt 158–179)* |

[1]Positions of vsRNAs mapped to the viral negative-strand RNA1 were given from 3' to 5'.

[2]Positions of vsRNAs mapped to the viral positive-strand RNA1 were given from 5' to 3'.

— indicates that no phased vsRNAs at this position were found in the library.

*indicates phased vsRNAs that were identical to the phased vsRNAs detected in mouse embryonic stem cells infected by NoVΔB2.

—** indicates no phased vsRNAs at this position were found in the library or in mouse embryonic stem cells infected by NoVΔB2.

Consistent with the known in vitro activity of the B2 protein to inhibit the processing of long dsRNA into siRNAs, however, viral small RNAs detected by either deep sequencing or Northern blotting during wild-type NoV infection do not have the properties of canonical siRNAs. Northern blot detection of viral siRNAs in NoVΔB2-infected mice suggests that the use of in vivo infection models and/or viruses incapable of inhibiting siRNA biogenesis may facilitate detection of siRNAs targeting other mammalian viruses. Moreover, NoV infection both in vitro and in vivo requires the RNAi suppressor activity of its B2 protein. In particular, suckling mice produced abundant viral siRNAs and became completely resistant to the lethal infection by NoV after substitution of a single amino acid in B2 that eliminates its RNAi suppressor activity. Thus, the typical RNAi response induced by virus infection in mammals has potent antiviral activity. The striking similarities in the induction and suppression of antiviral RNAi by the closely related FHV and NoV in fruit flies, nematodes, and mammals highlight an evolutionary conserved role of RNAi in antiviral defense within the animal kingdom. Compared with the antiviral immunity mechanisms reported to date in mammals, virus clearance by antiviral RNAi has a distinct effector mechanism and does not require cell death. Nevertheless, this mammalian immunity mechanism exhibits properties known to be associated with innate and adaptive immunity because it involves rapid host recognition of a microbe associated molecular pattern dsRNA and a mechanism of specificity determined by pathogen-derive siRNAs.

Studies with mESCS Infected with Encephalomyocarditis Virus:

Ascertaining genetically the DICER-dependency of mammalian vsRNA is complicated by the essential contribution of the mammalian RNAi machinery (one Dicer, four Ago) to the endogenous microRNA (miRNA) pathway. Pluripotent mouse embryonic stem cells (mESCs) withstand the complete ablation of DICER (DCR) or ARGONAUTE (AGO) functions and support RNAi triggered by long dsRNA possibly because they lack an IFN response; accordingly, DCR-dependent endogenous siRNAs are detected in these cells. It was reasoned that mESCs constituted potentially valuable models to genetically validate both viral siRNA accumulation and VSR function in authentic mammalian infection contexts.

Figure 7A:
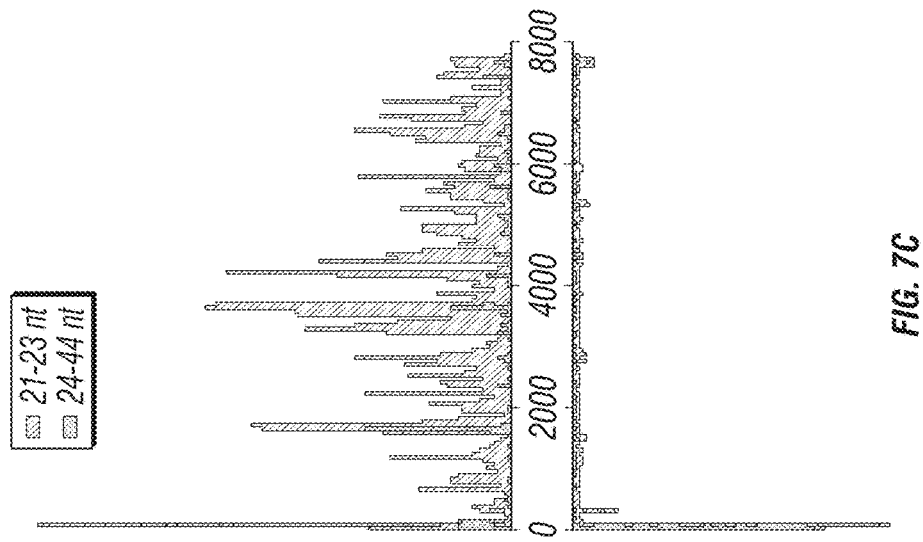
FIG. 7A-E provides for the characterization of EMCV-derived siRNAs in infected mESCs. (A) Western analysis of EMCV VP1 levels in E14 mESCs at 3 and 6 hpi. NI: non-infected. ACTIN: protein loading control (B) Size distribution of vsRNA deep-sequencing reads mapping the EMCV genome in the samples from (A). (C) 21-23-nt and 24-44-nt read distributions along the (+) and (−) strand of the EMCV genomic RNA at 6 hpi. (D) Same as (C), but along the first 5'-terminal 300-nt. Symmetrical reads are numbered. The asterisk indicates the read sequence against which a oligonucleotide probe was designed to detect the EMCV 5'-end siRNA in the Northern analysis in (E). Inset: perfect duplexes formed by the abundant reads 1-2 and 3-4; 2-nt 3' overhangs are indicated in red. The radar plots display 21-23-nt reads in each of 22 possible registers in the full EMCV (+) and (−) strands; the 5' first nucleotide of the genome defines register #1. The distance to the center indicates the percentage of reads in each register. (E) Northern analysis of EMCV 5'-end siRNAs at 6 hpi. Total RNA from SUC-SUL (SS) transgenic *Arabidopsis* run in parallel and hybridized secondarily provides an RNA size-marker for 21-nt and 24-nt siRNAs.
Figure 8A:
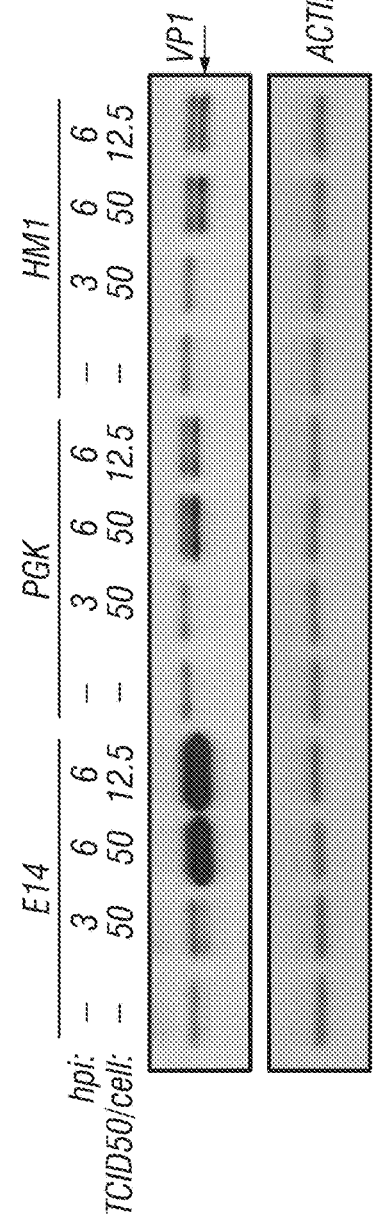
Figure 8B:
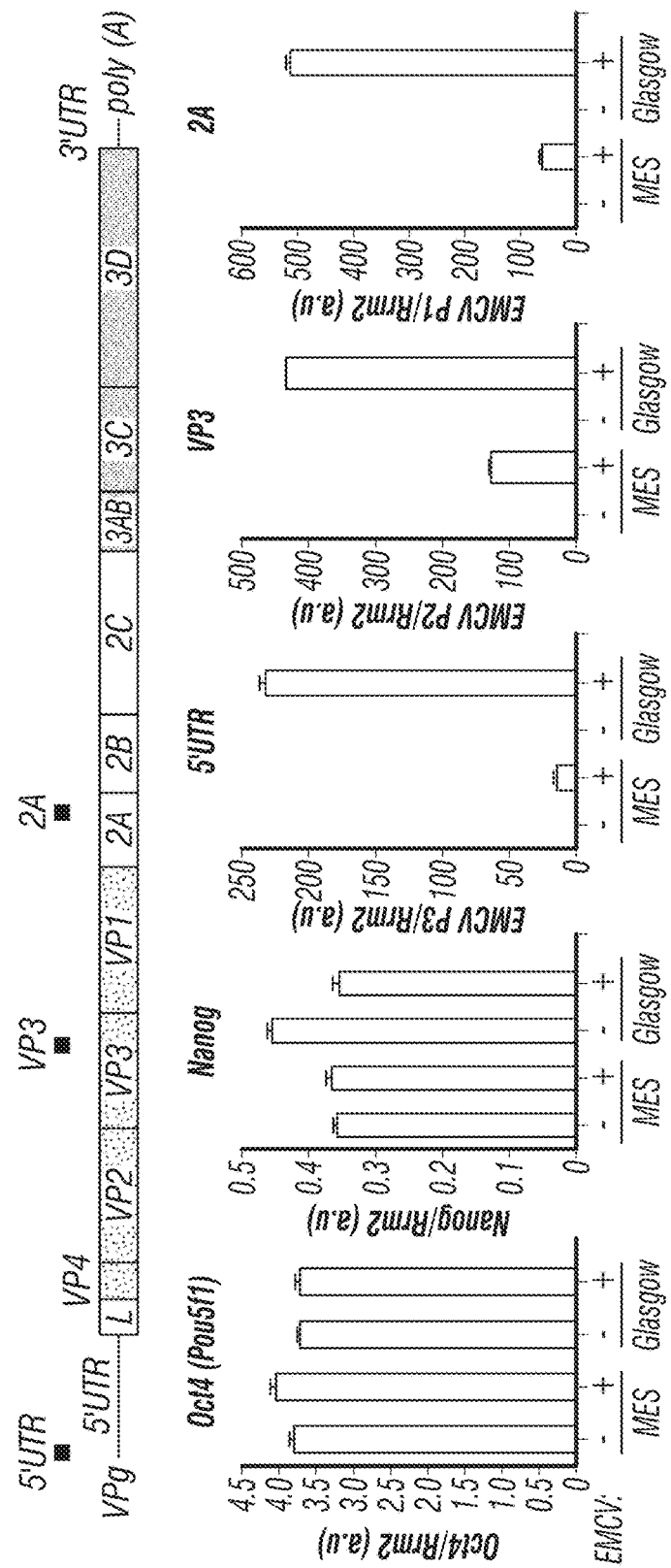
Figure 8C:
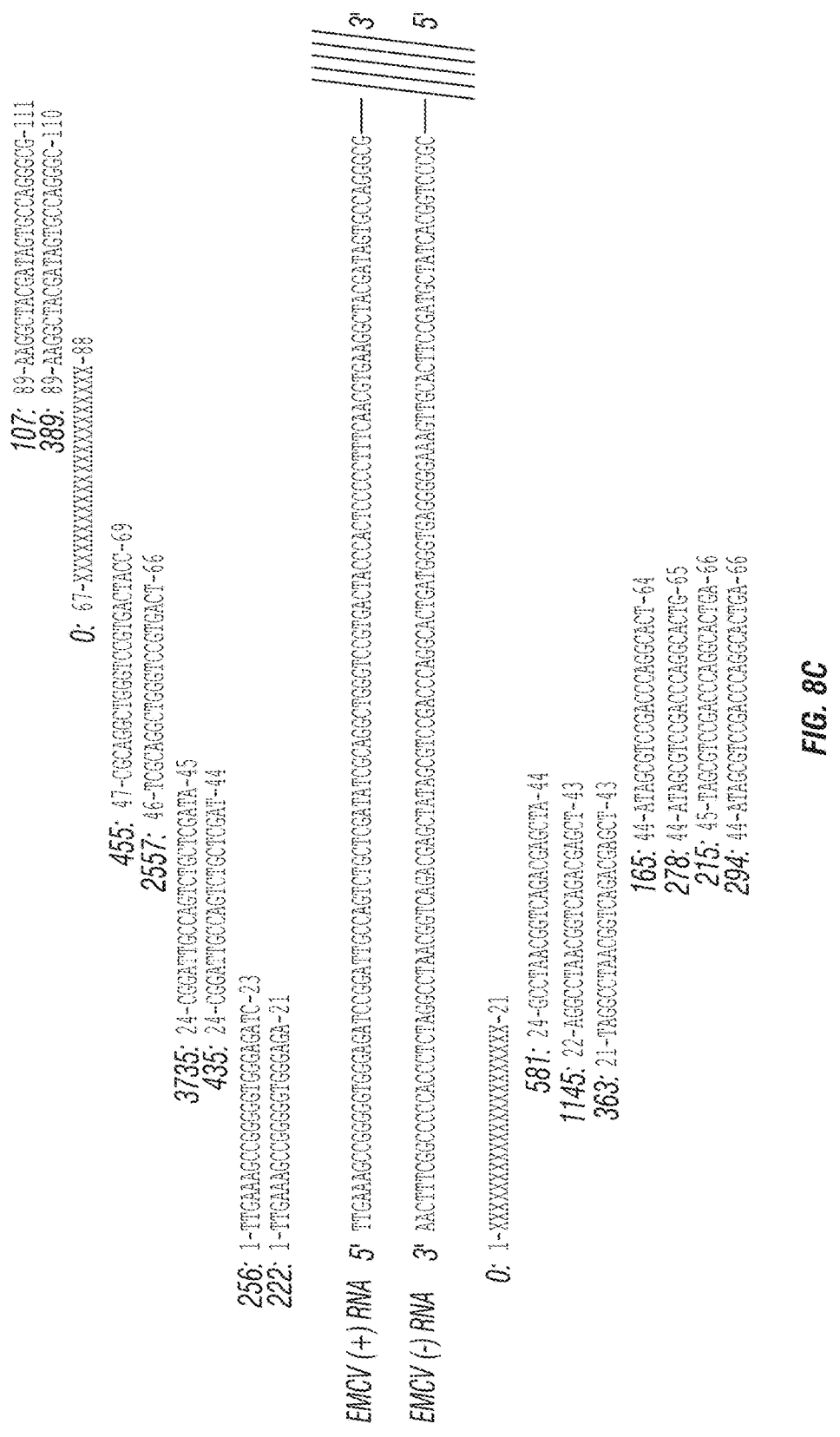

Several mESC lines were infected with purified virions of encephalomyocarditis virus (EMCV), a mammalian positive-sense single-stranded RNA (ssRNA) picornavirus producing high levels of dsRNA within its 8-hour infection cycle. All cells accumulated the EMCV-encoded VP1 capsid to varying degrees, with the highest levels displayed displayed by line E14 (see FIG. 7A and FIG. 8A-B). In two separate infections, 15- to 50-nt-long RNA was isolated from E14 mESCs and subjected to ILLUMINA deep-sequencing (see TABLE 6).

TABLE 6

Quantitive date from ILLUMINA deep-sequencing analyses

| Read characteristics | | infections with EMCV | | | | | infections with NoV | | infections with NoVΔB2 | |
|---|---|---|---|---|---|---|---|---|---|---|
| | | mESCs d0 | | | mESCs d10 | IP mAGO2 | RNA1 | RNA2 | RNA1 | RNA2 |
| | | 3 hpi | 6 hpi | 6 hpi | 6 hpi | 6 hpi | 72 hpi | 72 hpi | 72 hpi | 72 hpi |
| mouse genome/ 19/44-nt | Total mapped reads | 33,989,187 | 28,024,435 | 30,159,934 | 28,032,772 | 36,841,148 | 42,698,984 | 42,633,218 | 35,994,680 | 35,982,151 |
| | Mapped | 33,985,104 | 27,903,177 | 29,945,086 | 27,991,320 | 36,682,302 | 42,616,920 | 42,616,920 | 35,980,340 | 35,980,340 |
| | 21-nt | 3,507,409 | 3,210,403 | 3,523,909 | 2,732,889 | 3,476,292 | 4,412,863 | 3,886,312 | 4,412,863 | 3,886,312 |
| | 22-nt | 8,722,629 | 8,104,811 | 7,692,901 | 7,030,673 | 7,541,514 | 10,584,482 | 10,275,923 | 10,584,482 | 10,275,923 |
| | 23-nt | 5,318,723 | 3,991,681 | 4,615,584 | 4,771,356 | 4,993,130 | 5,839,149 | 5,299,375 | 5,839,149 | 5,299,375 |
| | Total 21-23-nt | 17,548,761 | 15,306,895 | 15,832,394 | 14,534,918 | 16,010,936 | 20,836,04 | 19,461,610 | 20,836,494 | 19,461,610 |
| | miRNAs | 22,338,674 | 13,719,791 | 18,833,978 | 16,337,825 | 26,047,613 | 21,653,457 | 21,653,457 | 17,533,962 | 17,533,962 |
| | % of mouse mapped miRNAs | 65.73 | 49.17 | 62.90 | 58.37 | 710I | 50.81 | 50.81 | 48.73 | 48.73 |
| viral genome/ 19-44-nt | Mapped | 4,083 | 121,258 | 214,848 | 41,452 | 158,846 | 82,064 | 16,298 | 14,340 | 1,811 |
| | mapped on the (+) strand | 3,905 | 110,311 | 197,877 | 40,325 | 155,477 | 69,411 | 12,689 | 10,217 | 1,476 |
| | mapped on the (−) strand | 178 | 10,947 | 16,971 | 1,127 | 3,369 | 12,653 | 3,612 | 4,123 | 335 |
| | (+):(−) strand ratio | 21.9 | 10.1 | 11.7 | 35.8 | 46.1 | 5.5 | 3.5 | 2.5 | 4.4 |
| | unique sequence | 1,230 | 13,088 | 28,480 | 11,489 | 12,896 | 15,479 | 4,497 | 4,731 | 923 |
| | % of total reads | 0.01 | 0.43 | 0.71 | 0.15 | 0.43 | 0.19 | 0.04 | 0.04 | 0.01 |
| viral 5' terminal 200-nt region/ 19-44-nt | Mapped | 179 | 17,011 | 18,383 | 2,455 | 3,632 | 4,851 | 2,805 | 2,635 | 487 |
| | mapped on the (+) strand | 169 | 10,971 | 11,403 | 2,310 | 2,290 | 4,311 | 2,435 | 1,987 | 401 |
| | mapped on the (−) strand | 10 | 6,040 | 6,980 | 145 | 1,342 | 540 | 370 | 648 | 86 |
| | (+):(−) strand ratio | 16.9 | 1.8 | 1.6 | 15.9 | 1.7 | 8.0 | 6.6 | 3.1 | 4.7 |
| | unique sequence | 29 | 229 | 336 | 120 | 121 | 714 | 745 | 286 | 217 |
| | % of total reads | 0.00 | 0.06 | 0.06 | 0.01 | 0.01 | 0.01 | 0.01 | 0,01 | 0.00 |
| viral genome/ 19-44-nt | Mapped | 789 | 39,917 | 58,665 | 6,780 | 18,574 | 12,648 | 2,323 | 6,596 | 454 |
| | mapped on the (+) strand | 712 | 31,003 | 44,381 | 6,392 | 16,231 | 10,398 | 1,761 | 4,061 | 314 |
| | mapped on the (−) strand | 77 | 8,914 | 14,284 | 388 | 2,343 | 2,250 | 563 | 2,535 | 140 |
| | (+):(−) strand ratio | 9.2 | 3.5 | 3.1 | 16.5 | 6.9 | 4.6 | 3.1 | 1.6 | 2.2 |
| | unique sequence | 229 | 2,802 | 5,449 | 1,665 | 1,5% | 2,403 | 660 | 1,408 | 215 |
| | % of total reads | 0.00 | 0.14 | 0.19 | 0.02 | 0.05 | 0.03 | 0.01 | 0.02 | 0.00 |
| | % of mouse mapped 21-23 nt reads | 0.00 | 0.26 | 0.37 | 0.05 | 0.12 | 0.06 | 0.01 | 0.03 | 0.00 |
| viral 5' terminal 200-nt region/ 21-23-nt | Mapped | 65 | 14,212 | 16,186 | 695 | 2,160 | 653 | 467 | 2,068 | 181 |
| | mapped on the (+) strand | 55 | 9,288 | 10,016 | 578 | 995 | 560 | 374 | 1,523 | 112 |
| | mapped on the (−) strand | 10 | 4,924 | 6,170 | 117 | 1,205 | 93 | 93 | 545 | 69 |
| | (+):(−) strand ratio | 5.5 | 1.9 | 1.6 | 4.9 | 0,8 | 6.0 | 4.0 | 2.8 | 1.6 |
| | unique sequence | 12 | 113 | 161 | 40 | 58 | 115 | 119 | 93 | 61 |
| | % of total reads | 0.00 | 0.05 | 0.05 | 0.00 | 0.01 | 0.00 | 0.00 | 0.01 | 0.00 |
| | % of mouse mapped 21-23 nt reads | 0.00 | 0.09 | 0.10 | 0.00 | 0.01 | 0.00 | 0.00 | 0.01 | 0.00 |

Figure 7B:
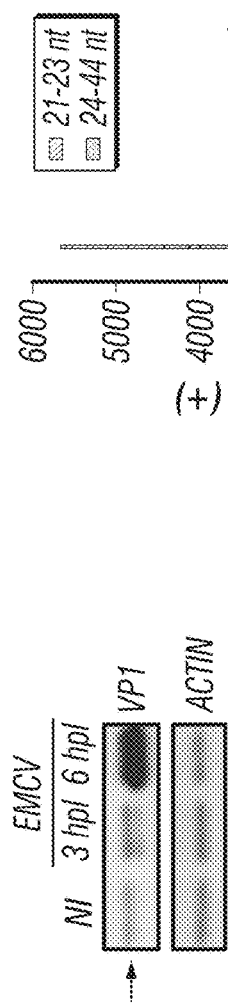

Six hours postinfection (hpi), 0.4 and 0.7% of total reads mapped the EMCV genome, of which 33 and 27% were in the 21- to 23-nt size range of DCR products (see FIG. 7B and TABLE 6). For comparison, miR-134, miR-296, and miR-470, which functionally target the mESC pluripotency factors Nanog, Oct4, and Sox2 represented respectively 0.11%, 0.02%, and 0.05% of total reads.

Figure 7C:
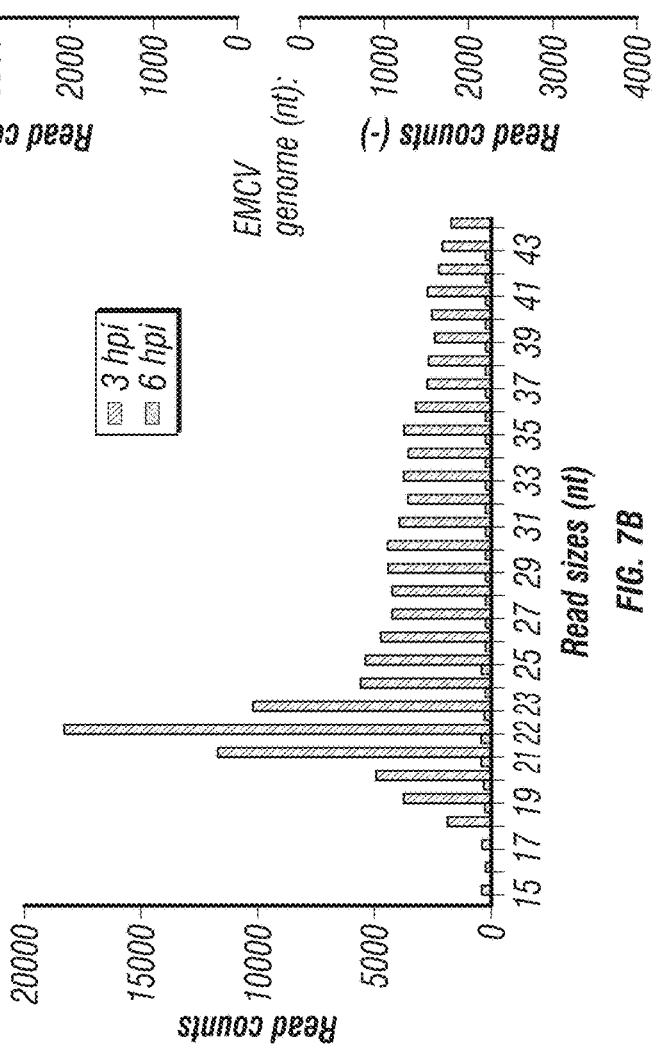

The remaining EMCV reads, in a heterogeneous 24- to 44-nt size range, mapped nearly exclusively along the viral positive strand (see FIG. 7C), which accumulates disproportionately more than the negative strand during positive sense RNA virus replication, and were thus mostly viral breakdown products. By contrast, 36 and 28% of 21- to 23-nt reads mapped to both viral strands within the first 200-nt of the EMCV 5' untranslated region and so exhibited a ~2:1 (+):(−) strand ratio contrasting with the ~10:1 ratio of all other reads (see FIG. 7C and TABLE 6). A less pronounced symmetrical reads distribution was also observed at the EMCV RNA 3'-end, whereas the remaining 21- to 23-nt reads originated from discrete positive-strand regions (see FIG. 7C).

Figure 7D:
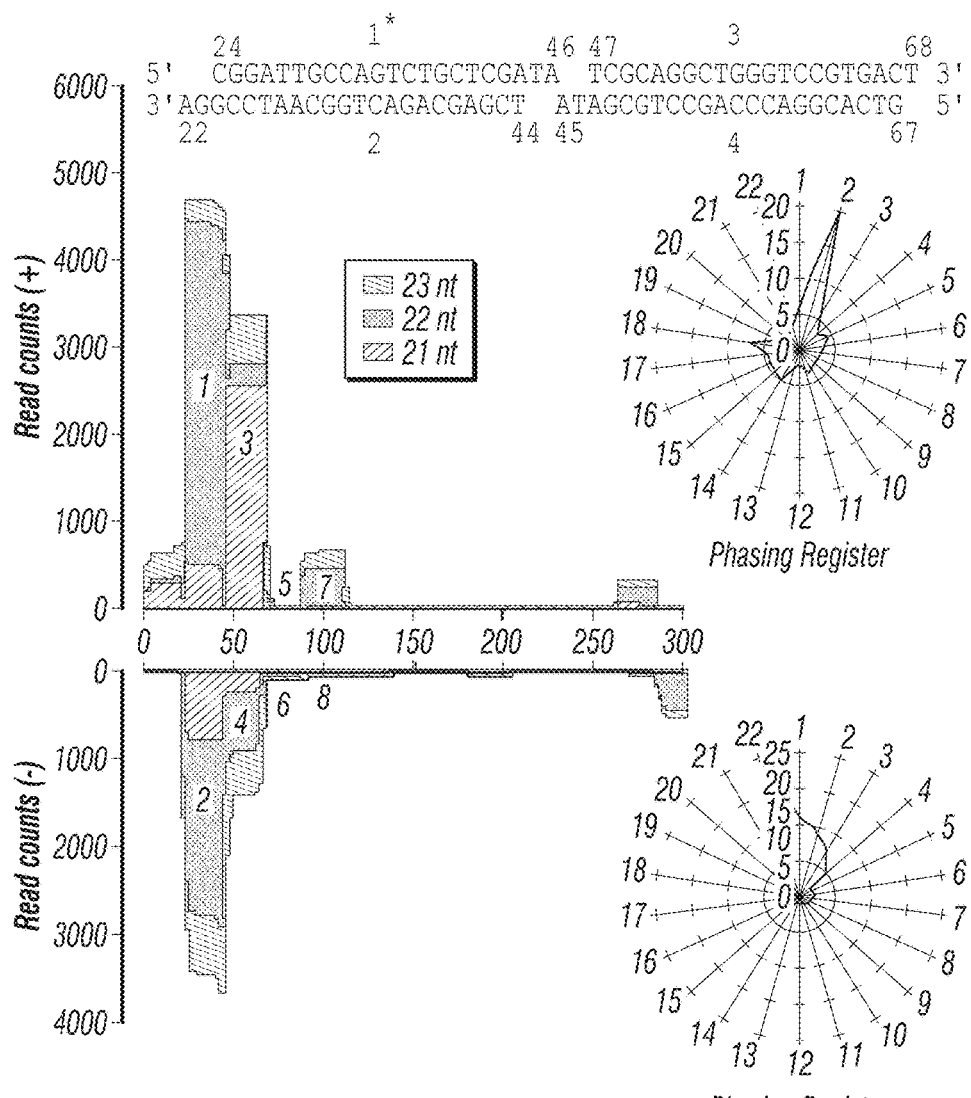
Figure 7E:
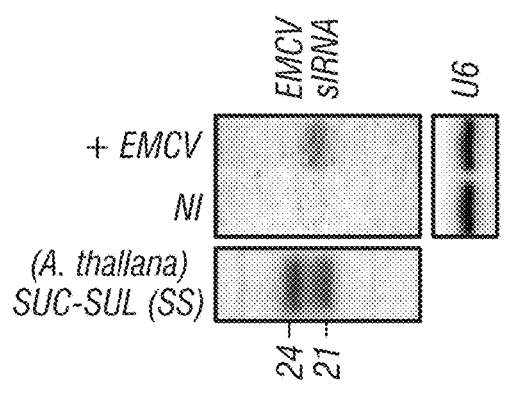
Figure 9D:
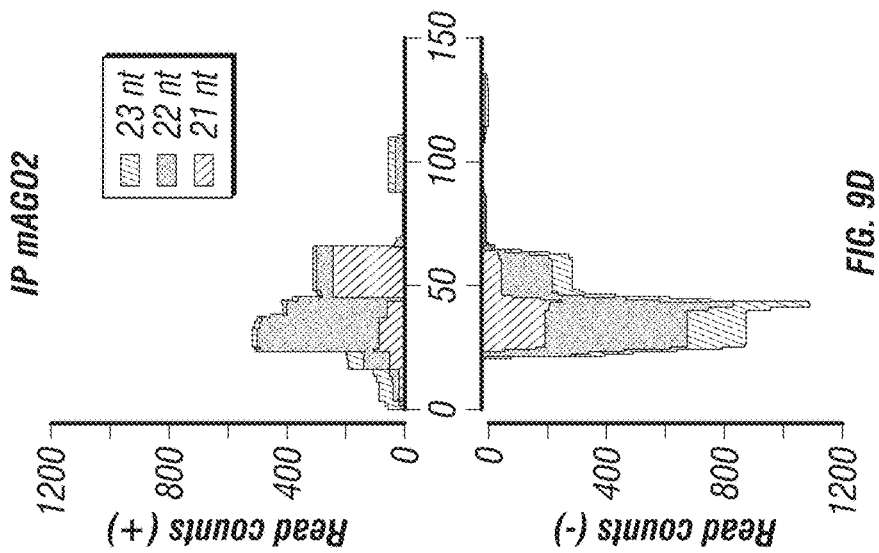
Figure 9C:
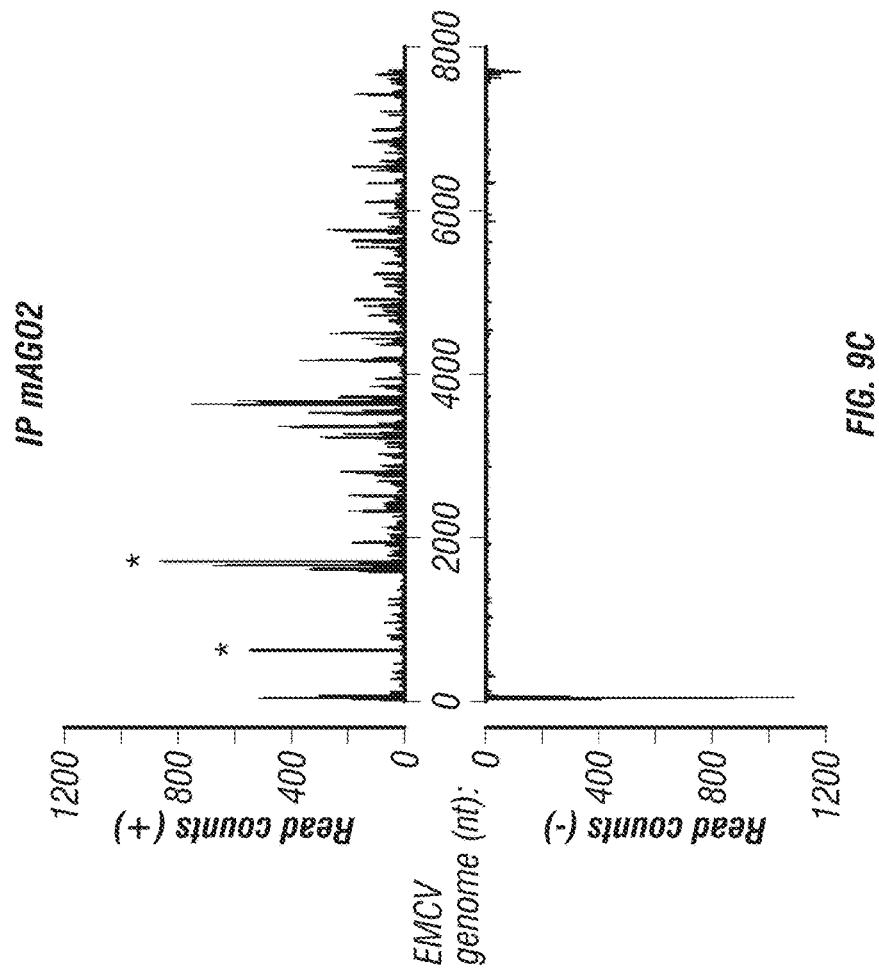
Figure 10A:
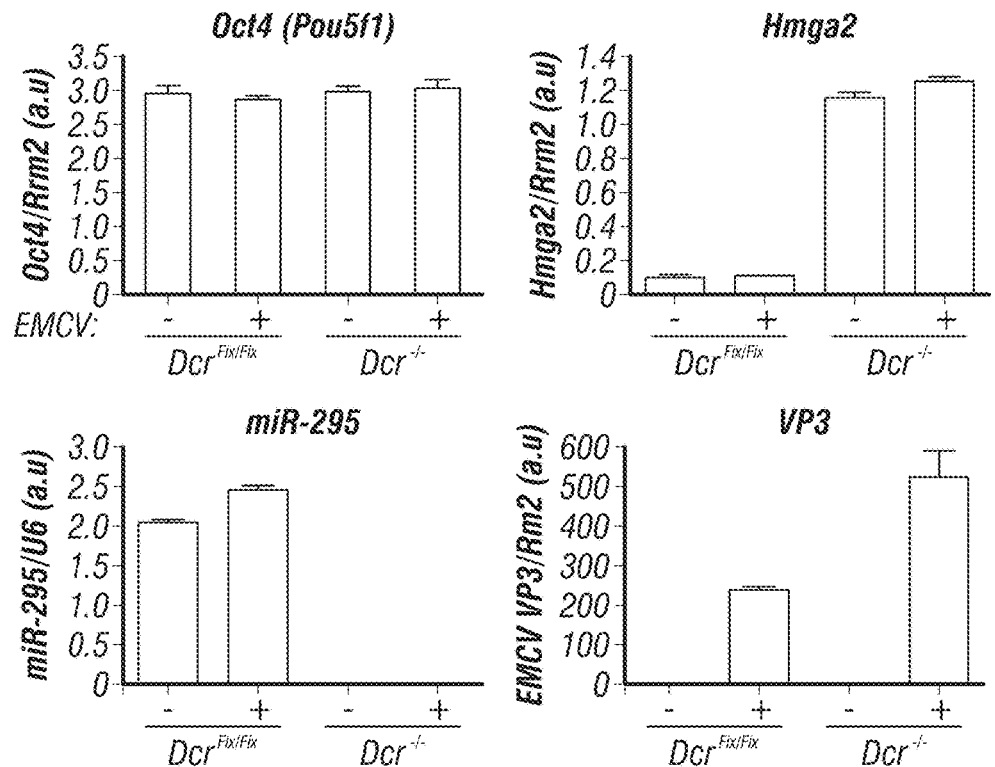
FIG. 10A-F provides for the characterization of RNA markers and structure of EMCV genome. (A) qRT-PCR analyses of the Oct4 mRNA, of one established mESC miRNA target (Hmga2 regulated by miR-196a), of miR-295 and of the EMCV RNA (VP3 region) in Dcr$^{Flx/Flx}$ and Dcr$^{-/-}$ mESCs infected (+) or not (−) with EMCV. Results are mean and standard deviations (SD) of two independent experiments. (B) Enrichment of miR-21 and miR-295 in FLAG-specific immunoprecipitation (IP FLAG) in WT mESCs or mESCs stably expressing epitope-tagged FLAG-HA human AGO2 (FHA-hAGO2) infected (+) or not (−) with EMCV, assessed by qRT-PCR analysis. SD calculated from qRT-PCR carried out in triplicates. (C) Immunoprecipitation of endogenous mouse AGO2 (mAGO2) using specific antibody or IgG control (IgG) in mESCs infected (+) or not (−) with EMCV. Protein blot analysis ensures comparable levels of infection (VP1, top) and confirms mAGO2 immunoprecipitation (bottom). (D) Percentage of reads mapping to pre-miRNA in IP of endogenous mAGO2 (mAGO2) of EMCV-infected mESCs shown in (C), as annotated by the ncPRO pipeline. Reads are classified as "unannotated" when they do not map any pre-miRNA. (E) 21-23-nt read distribution along the EMCV genome upon deep-sequencing of RNA isolated from endogenous AGO2 IP 6 hpi of mESCs. The two regions depicted correspond to the peaks marked with asterisks in FIG. 9C. The panel on the left depicts the J-motif of the EMCV IRES, the structure of which has been previously validated by nuclease probing; it is noteworthy that the major small RNA species corresponds to the binding site of EiF4A, known to change the IRES local confirmation. The RNA structure on the right panel was predicted by RNA fold but not validated experimentally. The two peaks (a and b) present in the EMCV genome at nt 1497-1670 are depicted on the corresponding RNA structure. The most abundant reads are indicated in red within the structures, and heat maps representing read variants or secondary reads. (F) qRT-PCR analysis of Oct4 and Nanog (pluripotency markers) and Fgf5 (ectoderm marker) in mESCs at day 0 (d0) and at day 10 (d10) of differentiation, infected (+) or not (−) with EMCV. Parallel quantification of EMCV RNA accumulation by qRT-PCR, as in FIG. 8B, is presented in the two right-most panels (5' UTR and 2A). Results are mean and SD of two independent experiments.
Figure 10B:
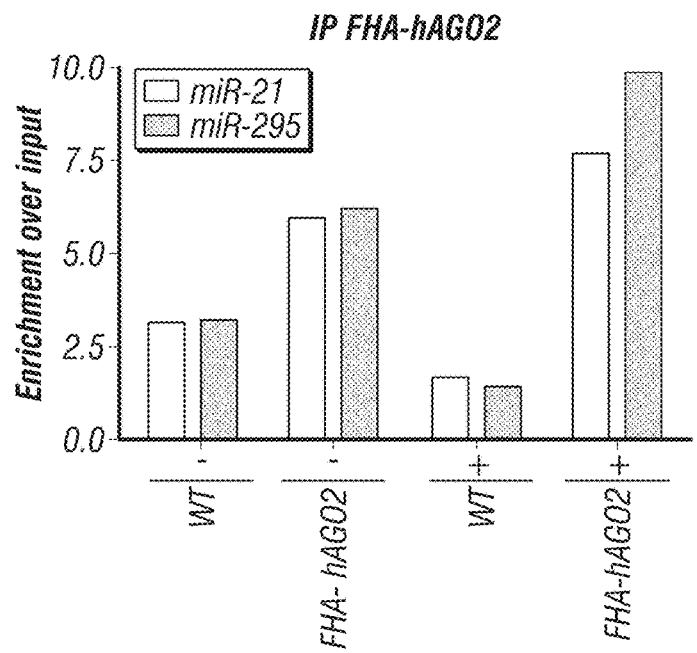
Figure 10C:
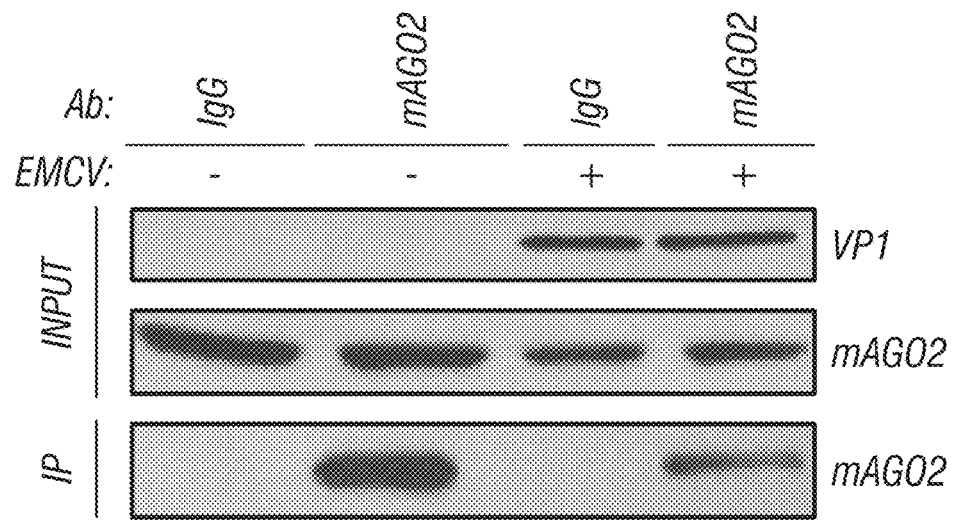
Figure 10D:
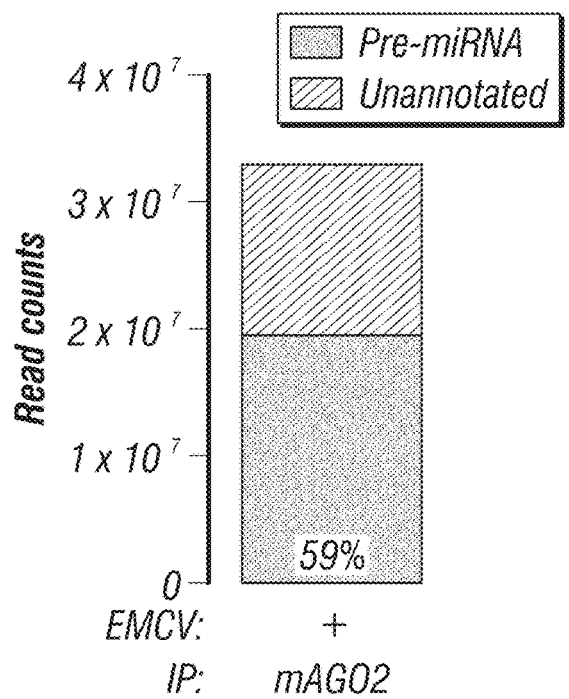
Figure 10E:
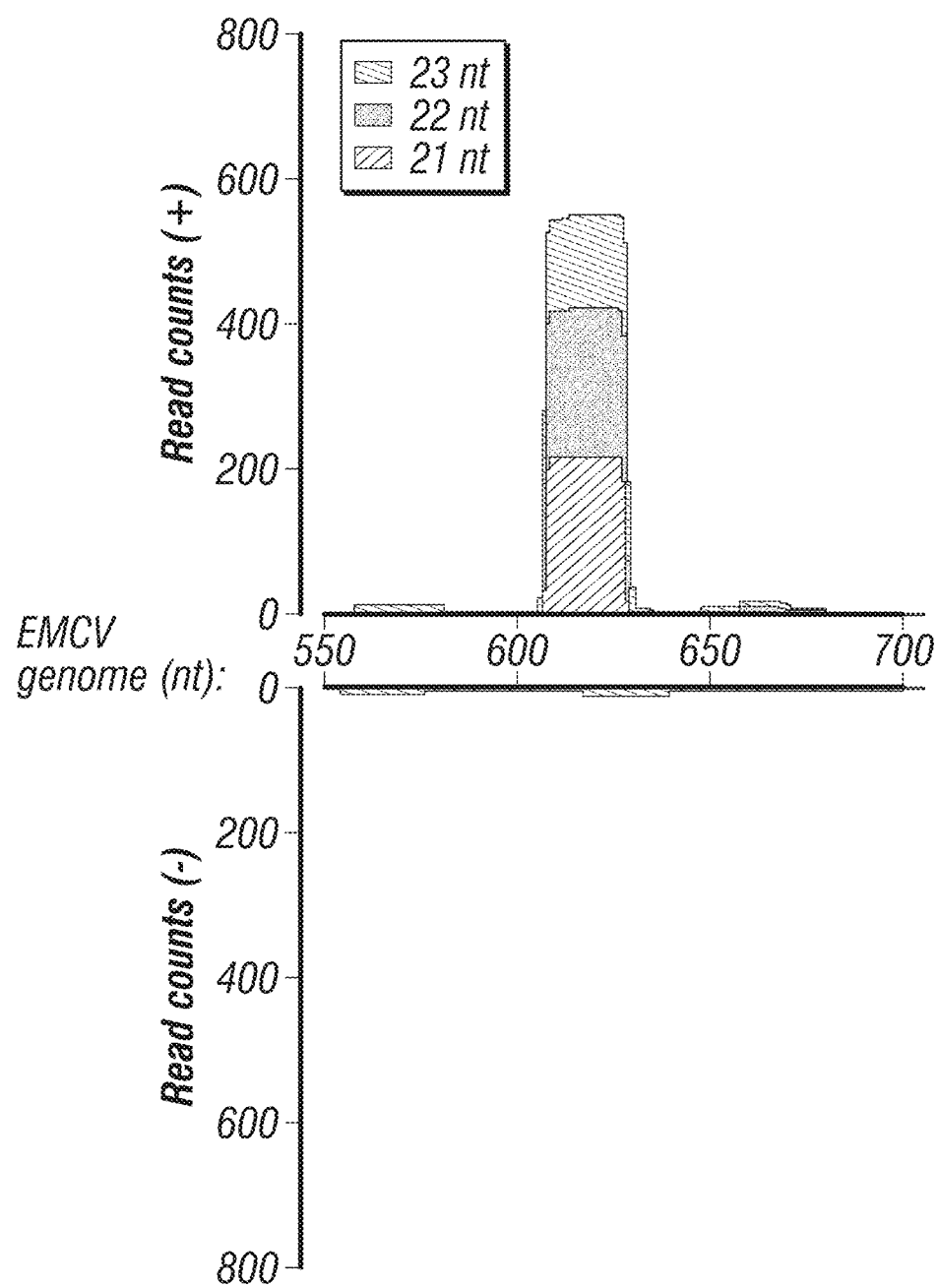
Figure 10E:
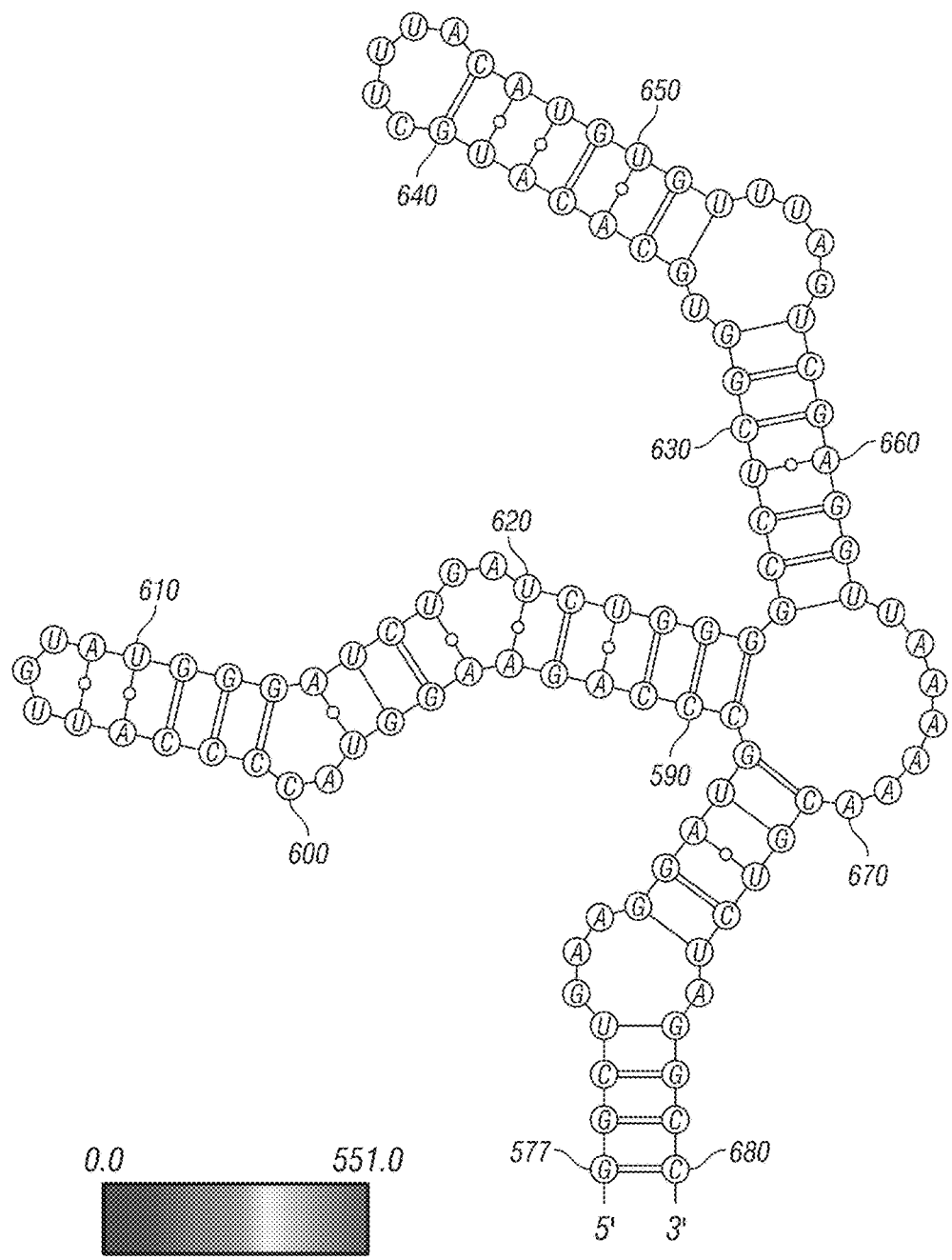
Figure 10E:
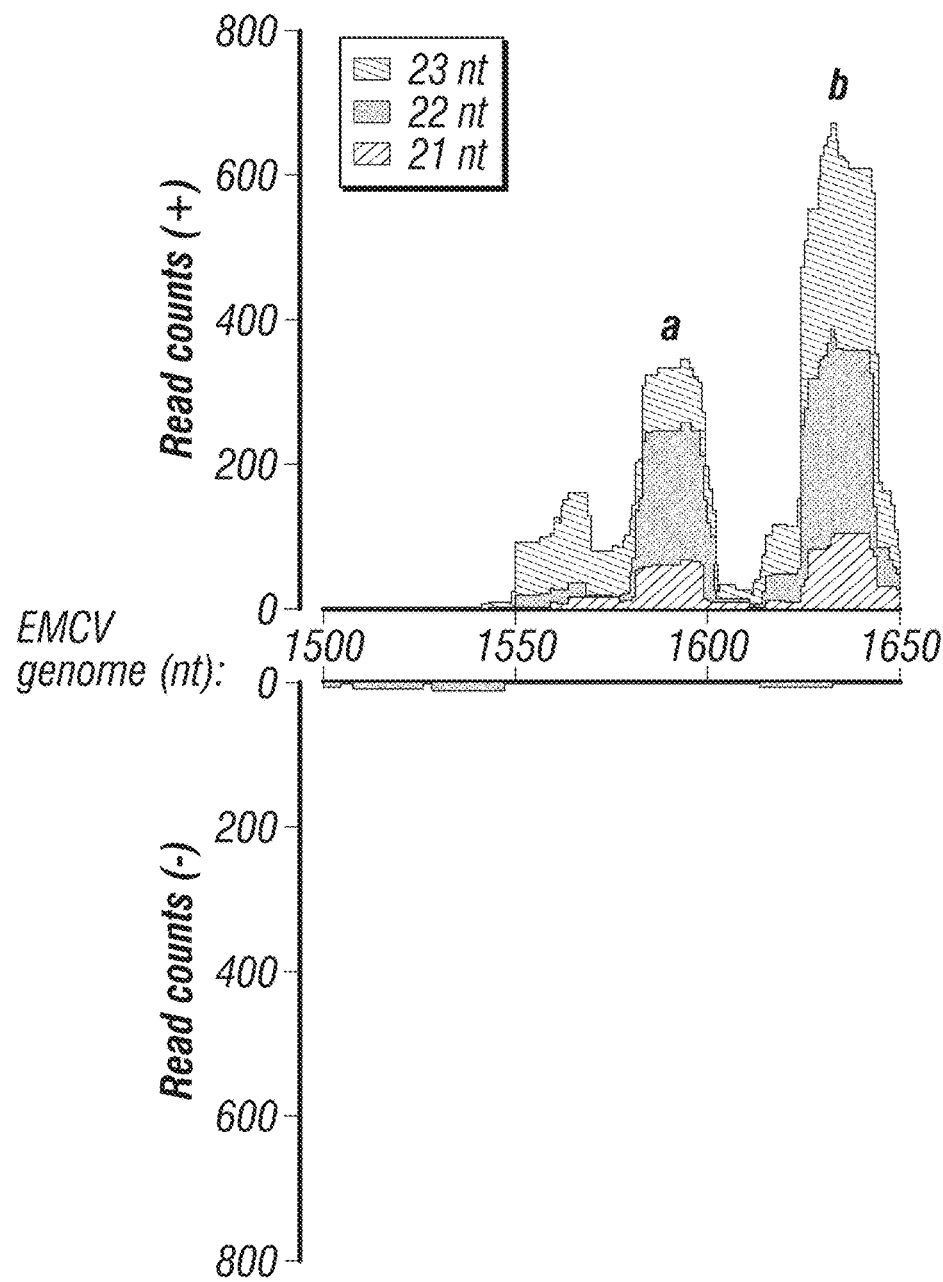
Figure 10E:
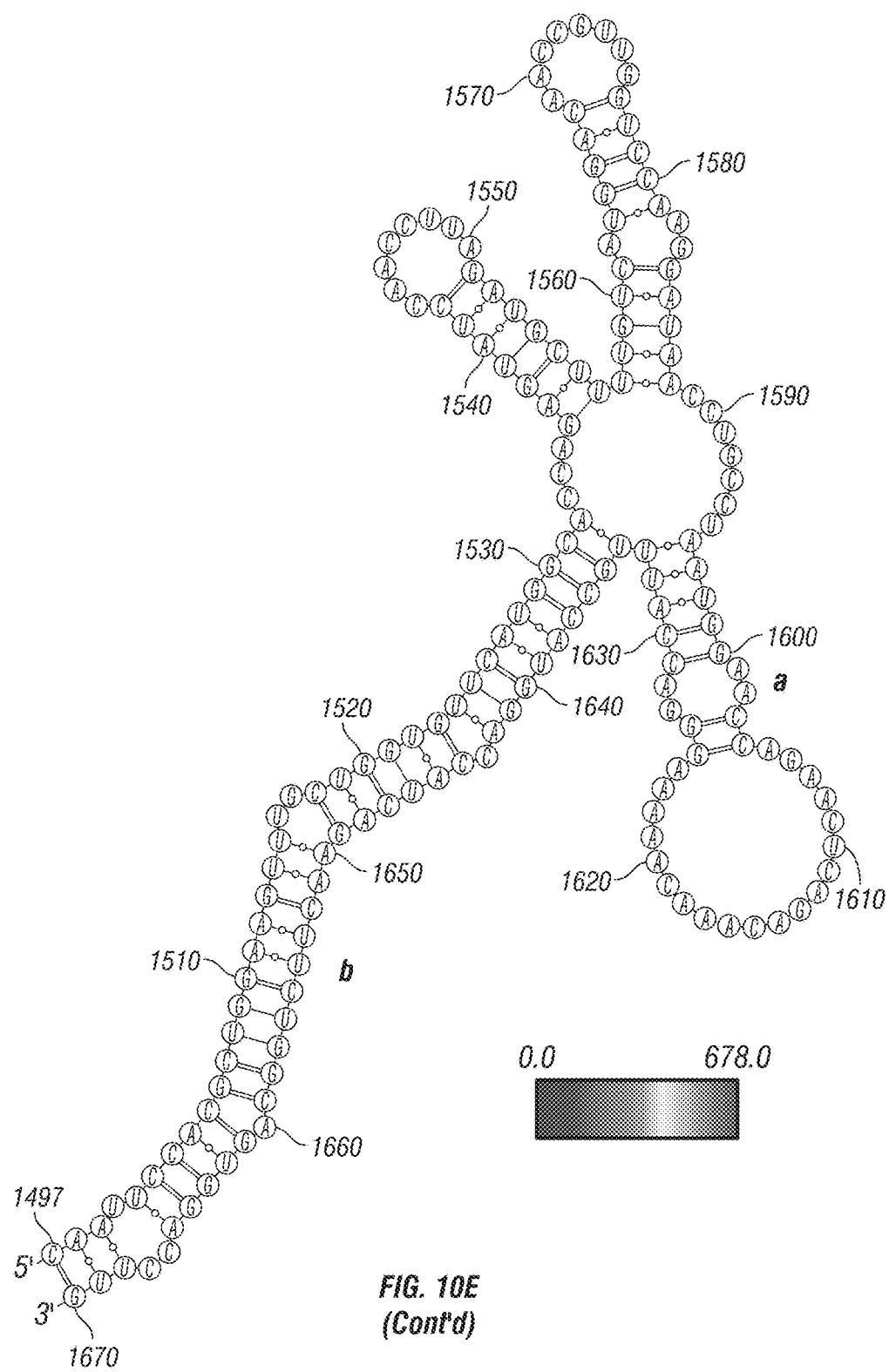

The symmetrical 5' and 3' EMCV reads mapped to the regions where dsRNA replication-intermediates (RIs) initiate during positive- and negative-strand synthesis. Similar to RI-derived siRNAs observed in virus-infected plants and invertebrates, abundant (+) and (−) reads at the EMCV 5' end formed contiguous and perfectly complementary duplexes with 2-nt 3' overhangs (see FIG. 7D). In addition, all EMCV-derived 21- to 23-nt reads defined a dominant, phased register initiated from the 5' end at a ~22-nt periodicity, in which complementary (+) and (−) strands were offset by 2 nt (see FIG. 7D and FIG. 8C-E). Northern analyses using oligonucleotide probes confirmed accumulation of the predicted 5'-end 22-nt siRNAs in EMCV-infected cells (see FIG. 7E). Phased, perfect duplexes with 2-nt 3' overhangs are signature products of sequential dicing of long dsRNA. The DCR-dependency of EMCV-derived vsRNAs was thus explored in Dcr knockout (Dcr$^{-/-}$) mESCs (see FIG. 9A and FIG. 10A), which, due to pleiotropy and reduced division rates, accumulated less EMCV than control Dcr cells. Viral inocula were thus precalibrated to produce comparable infection levels in both cell types (see FIG. 9A and FIG. 10A). Detected, as expected, in infected Dcr$^{Flx/Flx}$ mESCs, EMCV-derived 5'-end vsRNAs were below Northern detection limit in Dcr$^{-/-}$ mESCs (see FIG. 9A), which confirmed that they were bona fide siRNAs. Moreover, in wild-type (WT) mESCs, these were detected by Northern analysis of RNA from FLAG- and hemagglutinin (HA)-tagged human AGO2 (FLAGHA-hAGO2) immunoprecipitates (IPs) (see FIG. 9B and FIG. 10B) and by deep-sequencing RNA from endogenous mAGO2 IPs also containing cellular miRNAs (see FIG. 9C-D, and FIG. 10C-D). Abundant positive-strand reads also coincided with several peaks already observed in total RNA sequencing (see FIG. 9C, *), of which one mapped to the internal ribosomal entry site (IRES: nt 577 to 680) and another to a predicted dsRNA fold back (nt 1497 to 1670) (see FIG. 10E). Therefore, the AGO2-loading landscape of EMCV-infected mESCs comprised RI-derived and DCR-dependent siRNA duplexes, as well as other 21- to 23-nt vsRNAs generated from positive-strand secondary structures via an unidentified mechanism.

Figure 9G:
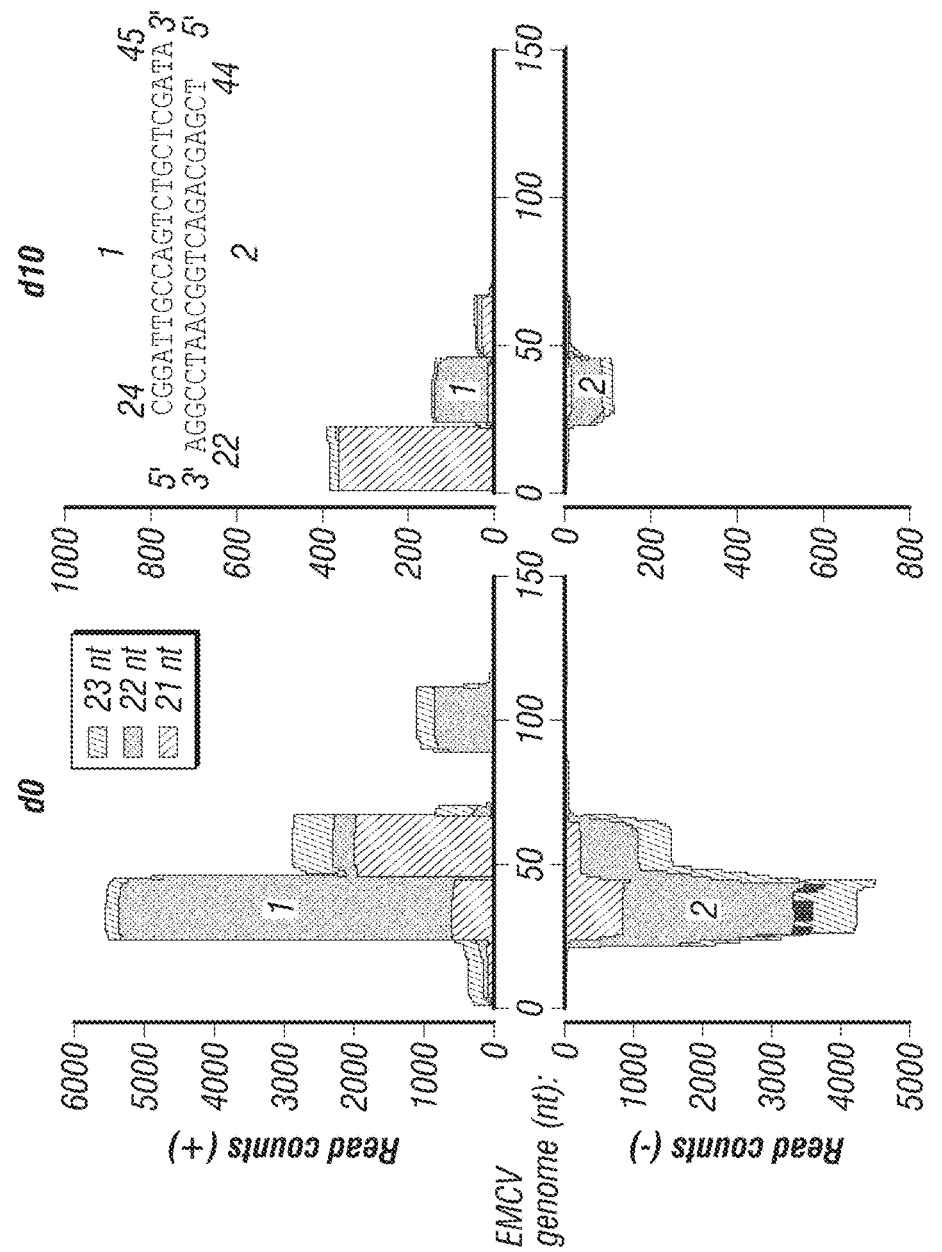
Figure 10F:
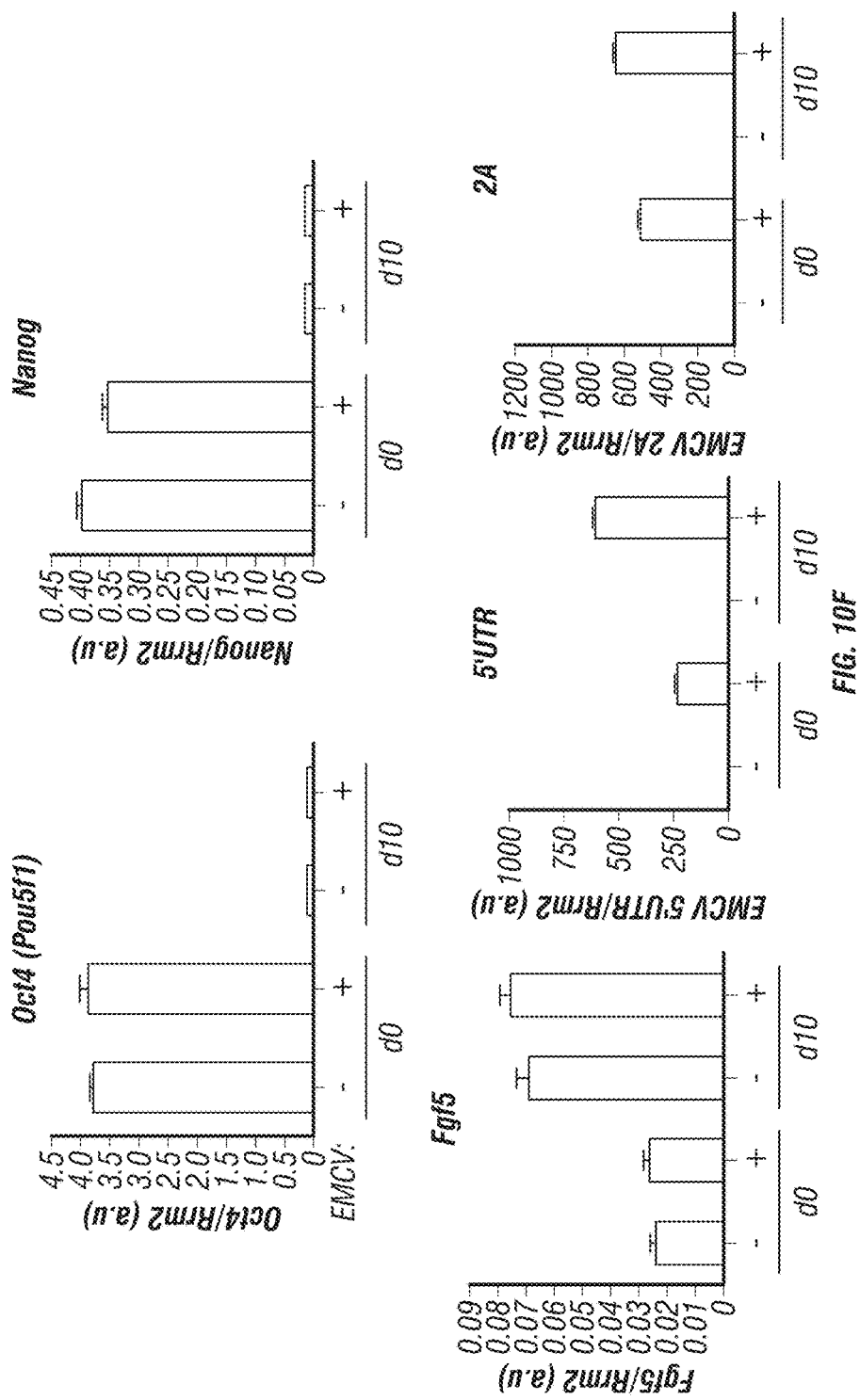

The use of mESCs granted an investigation of viral siRNA accumulation in genetically identical cells but under distinct differentiation states. Differentiation of E14-derived embryoid body was confirmed at day 10 by the loss of expression of pluripotency markers Nanog and Oct4 and gain in EMCV 5'-expression of the ectoderm-specific marker Fgf5 (see FIG. 9E and FIG. 10F). At 6 hpi, 5'-end siRNAs were below Northern detection in EMCV-infected day 10 compared with day 0 E14 cells, despite their similar infection levels (see FIG. 9E and FIG. 10F). Accordingly, EMCV-derived reads represented 0.15% of total deep-sequencing reads in infected day 10 cells, a nearly fivefold decrease compared to infected day 0 cells (see FIG. 9F). The 21- to 23-nt reads were also 10 times less abundant in day 10 cells as in day 0 cells but were still detectable, including in the first 5'-terminal 200 nt, representing 16% of all EMCV-derived reads (see FIG. 9G and TABLE 6). Therefore, EMCV siRNA accumulation was significantly reduced, albeit not abolished, by differentiation, unlike that of miRNAs (see FIG. 9E).

Figure 11A:
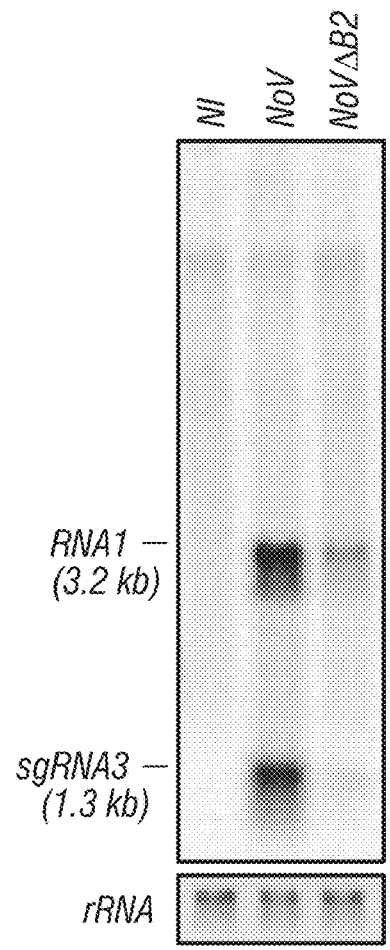
Figure 11B:
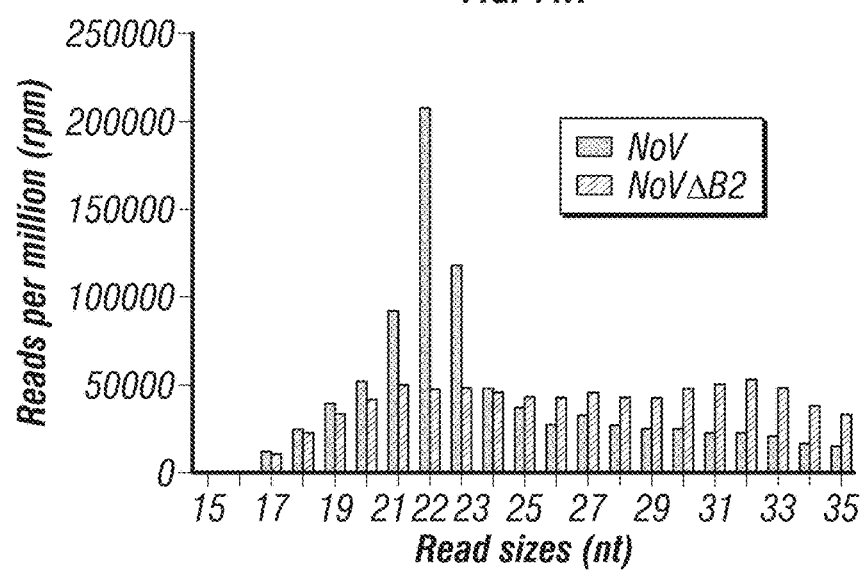
Figure 11C:
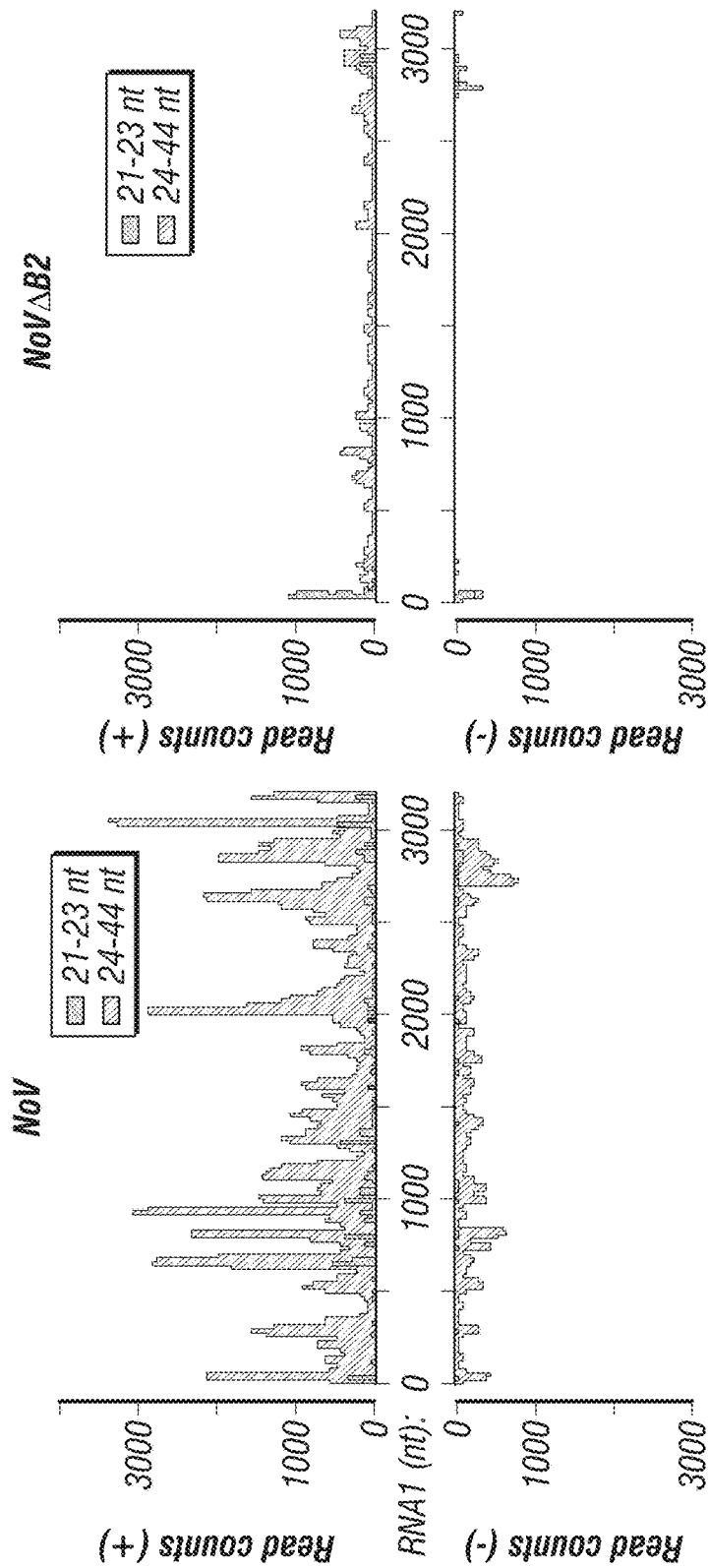
Figure 11E:
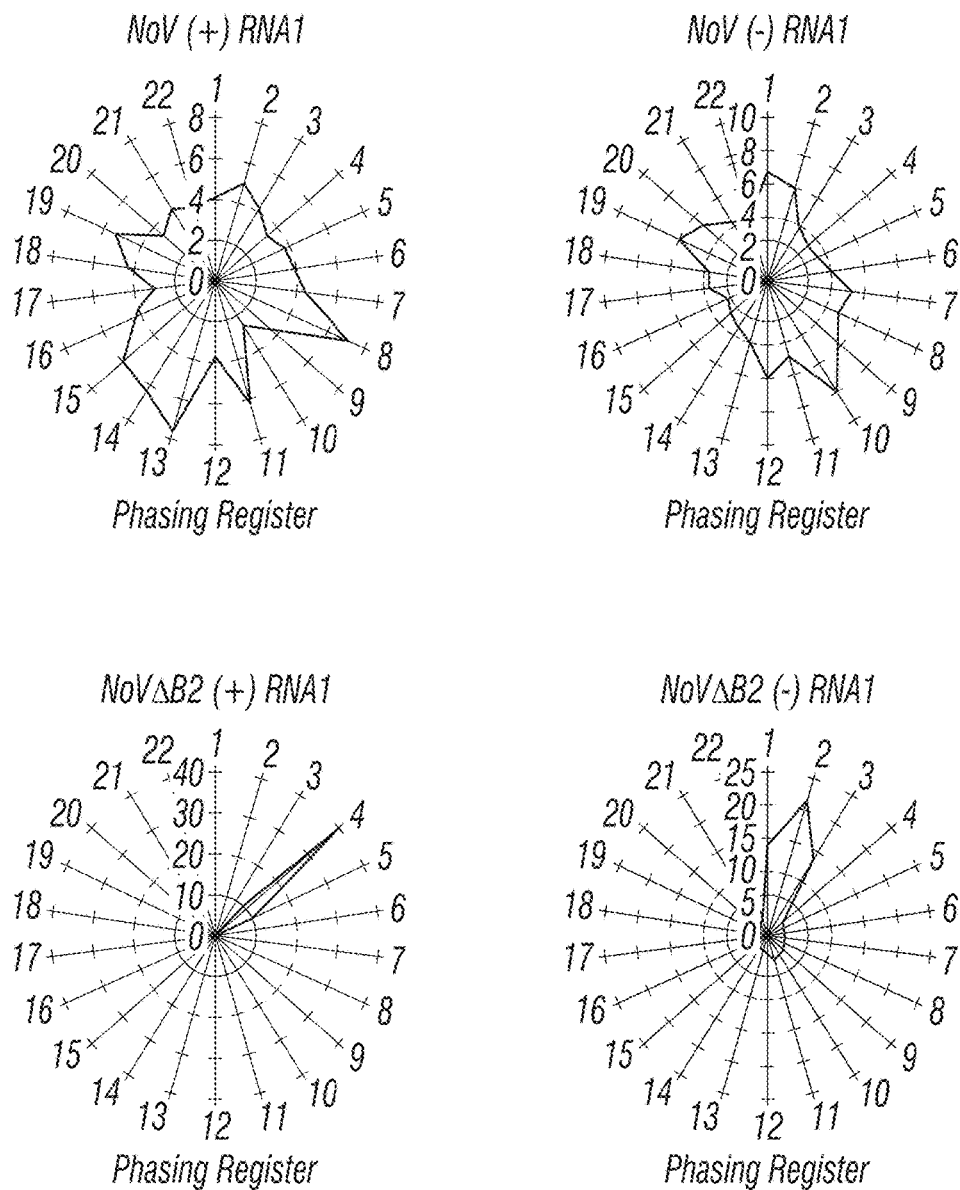
Figure 12A:
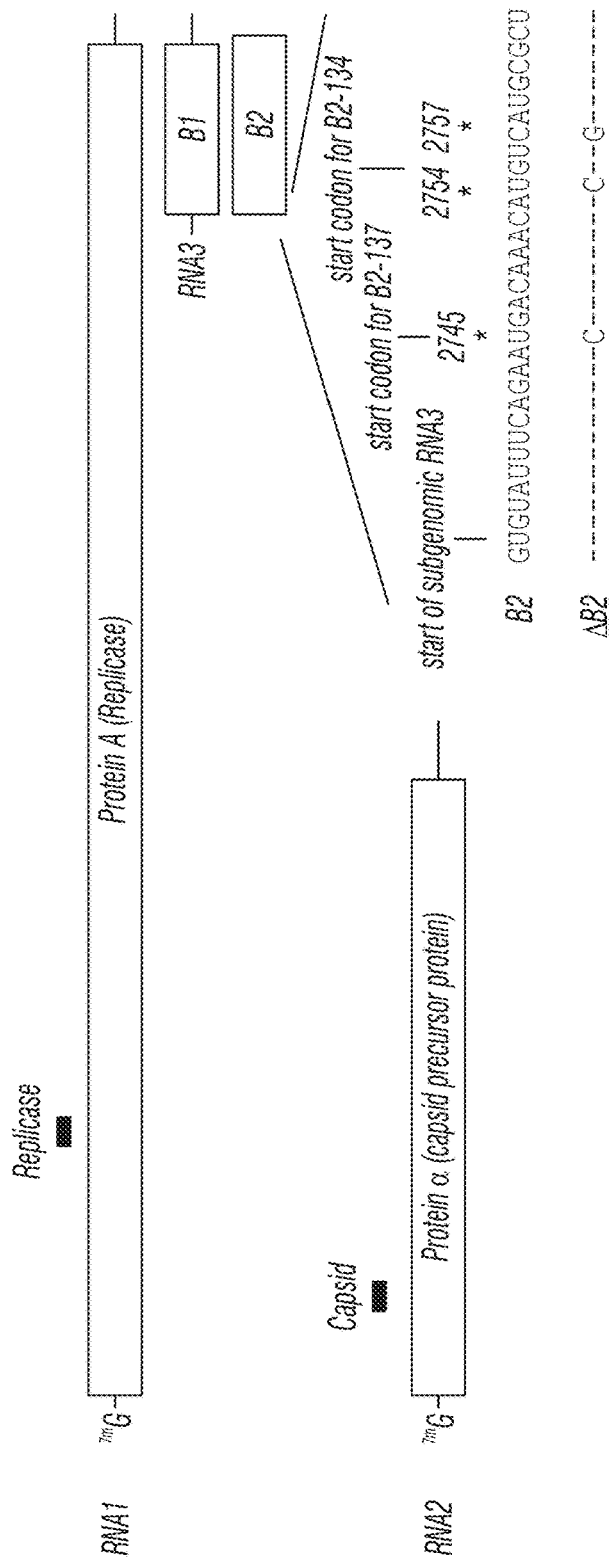
Figure 12C:
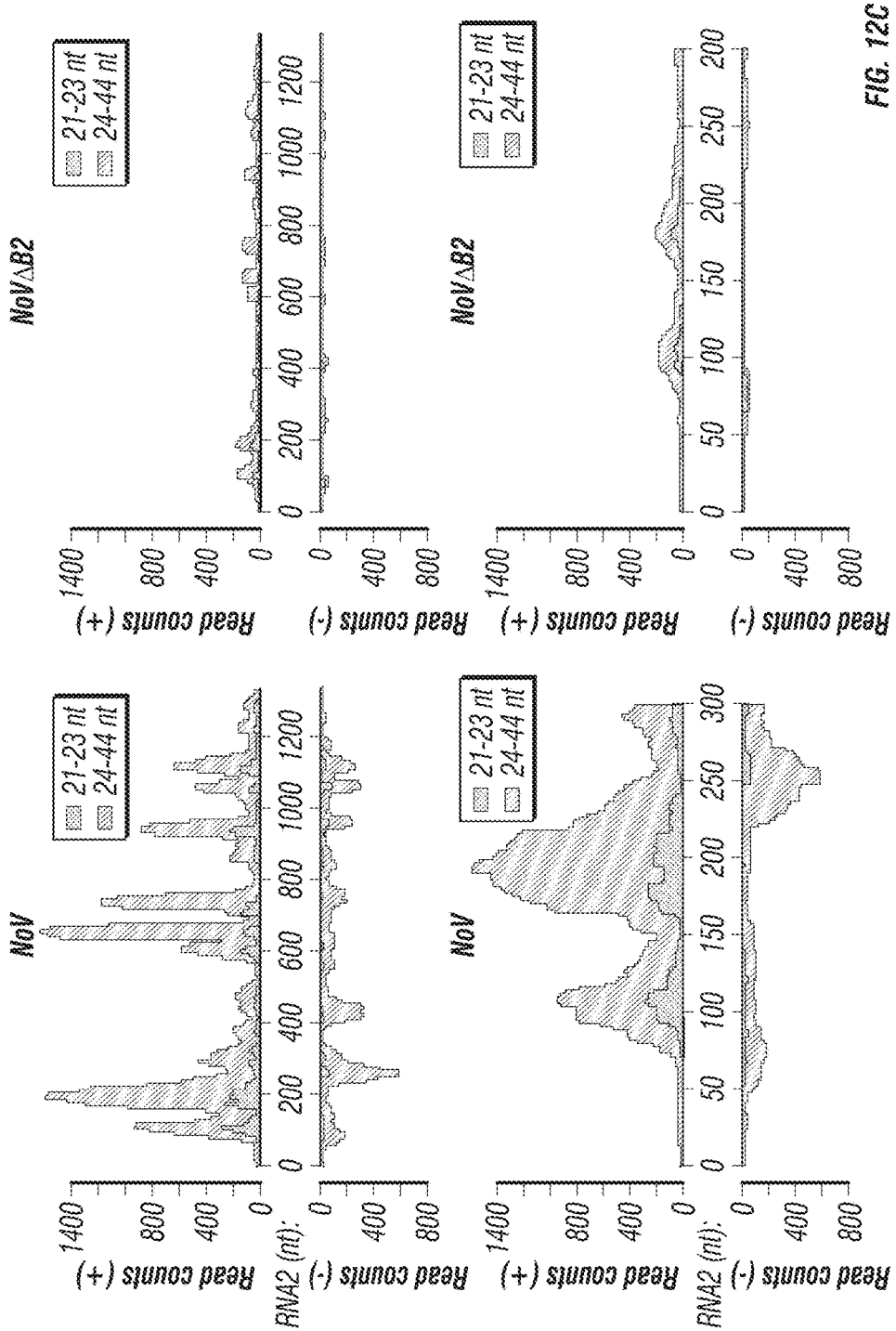
Figure 12D:
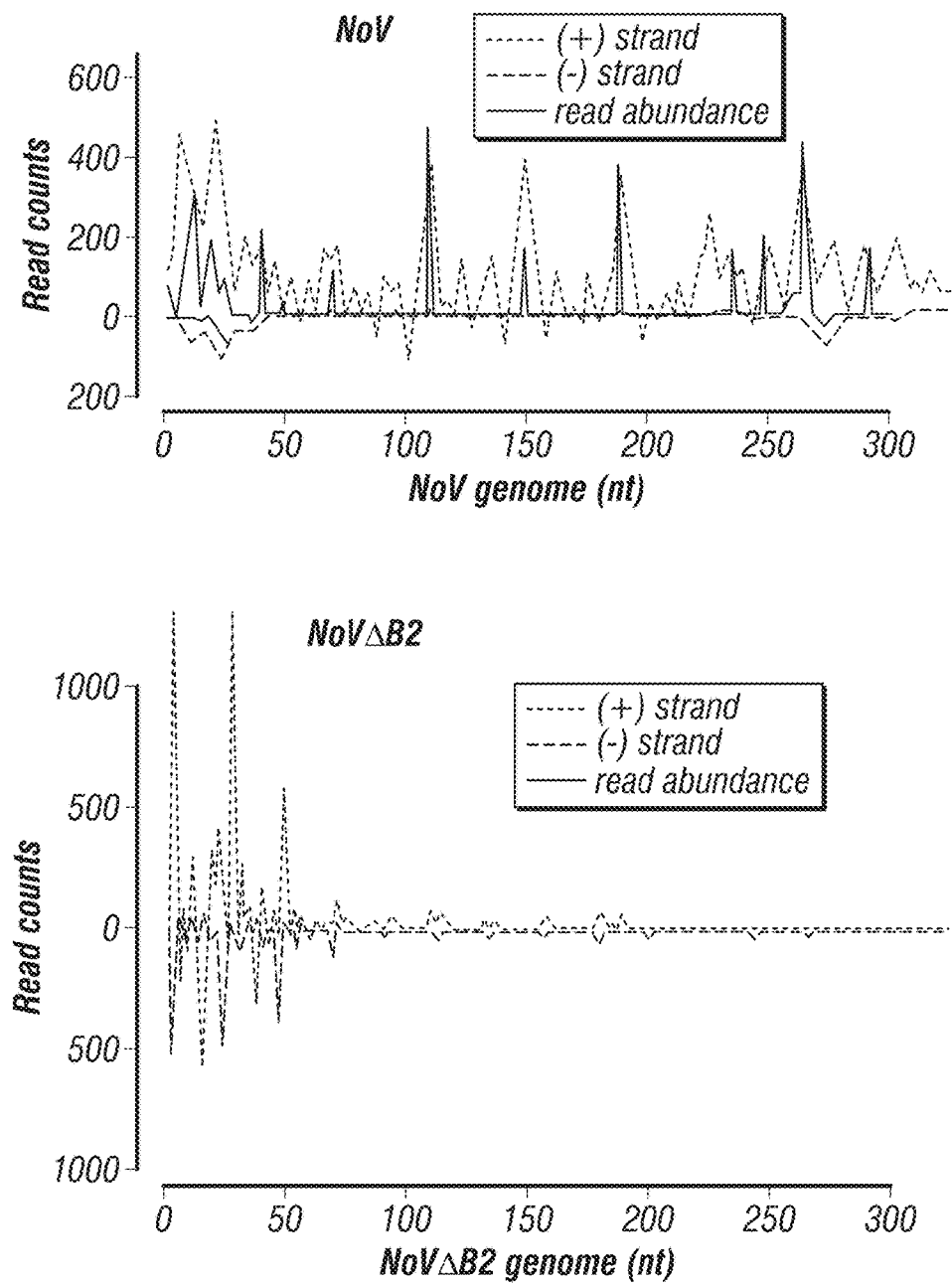
Figure 12E:
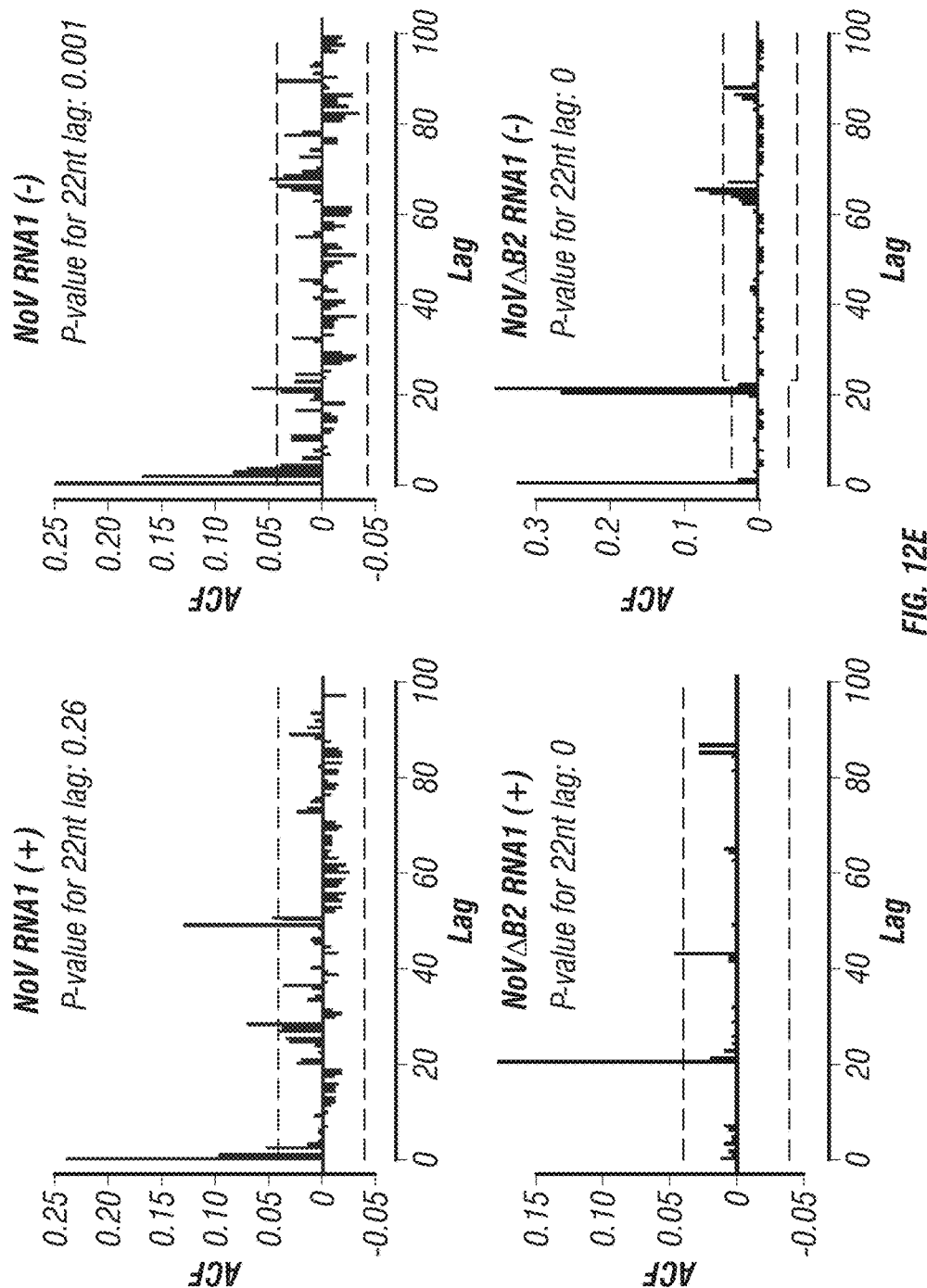

Genetic Rescue of VSR-Deficient Viruses in RNAi-Compromised Host Cells:

Demonstrating the antiviral activity of siRNAs entails the genetic rescue of VSR-deficient viruses in RNAi-compromised host cells, an approach not possible with EMCV for which a potential VSR awaits identification. The dsRNA binding B2 protein encoded by the bipartite, positive-sense ssRNA Nodamura virus (NoV) inhibits DCR activity during experimental mammalian RNAi, a property shared by its ortholog in the NoV-related Flock house nodavirus (FHV) in *Drosophila*. NoVor its B2-deficient counterpart, NoVΔB2, were titrated to similar levels in stable B2-expressing BHK-21 cells and subsequently used to infect E14 mESCs. NoVΔB2 accumulated considerably less than NoV at 3 dpi, and only the former infection was able to generate virus-derived 21- to 23-nt deep-sequencing reads (see FIG. 11A-B, and FIG. 12A-B), whereas global miRNA levels remained unchanged in both infections (TABLE 6). NoV-derived reads, heterogeneous in size, mapped mostly along the RNA-1 positive strand (see FIG. 11C, FIG. 12C, and TABLE 6). By contrast, those from NoVΔB2, nearly exclusively 21 to 23 nt in length, derived mainly from the 5' and 3' ends of RNA1 (+) and (−) strands (see FIG. 11C-D), which resembled the FHVDB2 siRNA pattern in *Drosophila*. Furthermore, NoVΔB2 5' end reads had a ~22-nt periodicity and formed contiguous, perfect duplexes with 2- to 3-nt 3' overhangs reminiscent of the DCR dependent EMCV siRNAs (see FIG. 11E-F). An identical set of phased, perfect duplexes was detected in both NoVΔB2-infected BHK-21 somatic cells and limbs of newborn mice but not upon infection with NoV (see FIG. 11F). Likewise, reads from the B2-proficient NoV displayed none of these features in mESCs despite their much higher abundance (see FIG. 11E-F, and FIG. 12D-E). Thus, mirroring the action of the FHV-encoded B2 VSR in *Drosophila*, DCR-dependent processing of RI-derived dsRNA was suppressed by the NoV-encoded B2 protein in mESCs. Furthermore, this B2-restricted mechanism operated almost identically in mESCs and suckling mice.

FHV B2 inhibits both siRNA processing and incorporation into AGO. Therefore, to explore antiviral RNAi in NoV-infected mESCs and to avoid functional redundancy with AGO1, AGO3, or AGO4, the quadruple Ago1,2,3,4 KO mESC line E7 was used, in which an ectopically expressed hAgo2 transgene is removable by tamoxifen application. hAgo2 depletion was confirmed 5 days after tamoxifen treatment (see FIG. 13A), upon which mESCs were infected with NoV or NoVΔB2 for 3 days. In two separate experiments, the NoV and NoVΔB2 RNA1 levels were respectively ~2 and ~8 times as high in tamoxifen-induced as in untreated mESCs (see FIG. 13B). Northern analyses further showed that NoVΔB2 accumulation was rescued in AGO2-deficient mESCs similarly to FHVΔB2 accumulation in Ago2-deficient *Drosophila* cells; the lower impact of AGO2 depletion on virulent NoV confirmed B2 VSR activity in authentic infections (see FIG. 13C). Combined with those obtained with EMCV, the results demonstrate that antiviral RNAi operates in mammalian cells.

Characterization of Viral siRNAs Loaded in Argonautes In Vivo:

Since siRNAs guide sequence-specific RNAi in RISC complexes, it is important to know if viral siRNAs are loaded in vivo into Ago complexes as was observed in cultured mouse ES cells. The data shows that total viral siRNAs produced at 1 and 2 dpi in mice infected with NoVΔB2 are enriched for duplexes with 2-nt 3' overhangs and exhibit no preference for any nucleotide at the 5' termini, which may reflect the population structure of viral siRNAs early in the induction of antiviral RNAi. It is hypothesized that viral siRNAs after loading into Argonaute complexes will show distinct differences because of the different accessibility and abundance of the positive and negative strands of the cognate viral RNAs before and after the target virus clearance. The total and Ago-coimmunoprecipitated (co-IP) small RNA populations from the hind limb tissues of suckling mice 1, 2, 3, 4, 7, 15, or 28 days post infection with NoVΔB2, is cloned, sequenced and compared. The anti-pan Ago monoclonal antibody from Millipore (Billerica, Mass.) is used for co-IP and TruSeq Small RNA sample Preparation Kit of Illumina to construct small RNA libraries. The unique barcodes added at the 5'-end of the primers used in the amplification of each library by PCR at the last step of library construction allow for sequencing up to 12 libraries in one lane of Illumina HiSeq 2000. ~10 million total reads for each library are generated. Since the two sequenced mouse small RNA libraries contained 0.11% (1 dpi) and 0.27% (2 dpi) virus reads, respectively, each library is predicted to include ~10,000 to 30,000 virus reads, which is sufficiently deep for analysis. The following properties of virus reads are compared among the libraries over the time course using computational algorithms: (i) the relative abundance of virus reads compared to total small RNA reads and total mouse mature miRNA reads; (ii) the length distribution pattern, strand ratio, nucleotide preference at each position of virus reads, (iii) densities of 21- to 23-nt viral siRNAs over the viral positive- and negative-strand RNAs 1 and 2, and (iv) enrichment for complementary pairs of viral siRNAs with 2-nt 3' overhangs. The studies indicate that NoVΔB2 is essentially cleared by 7 dpi. A further search will be performed for the viral genomic RNAs and for the infectious virions in the samples collected at late time points of infection.

Figure 15:
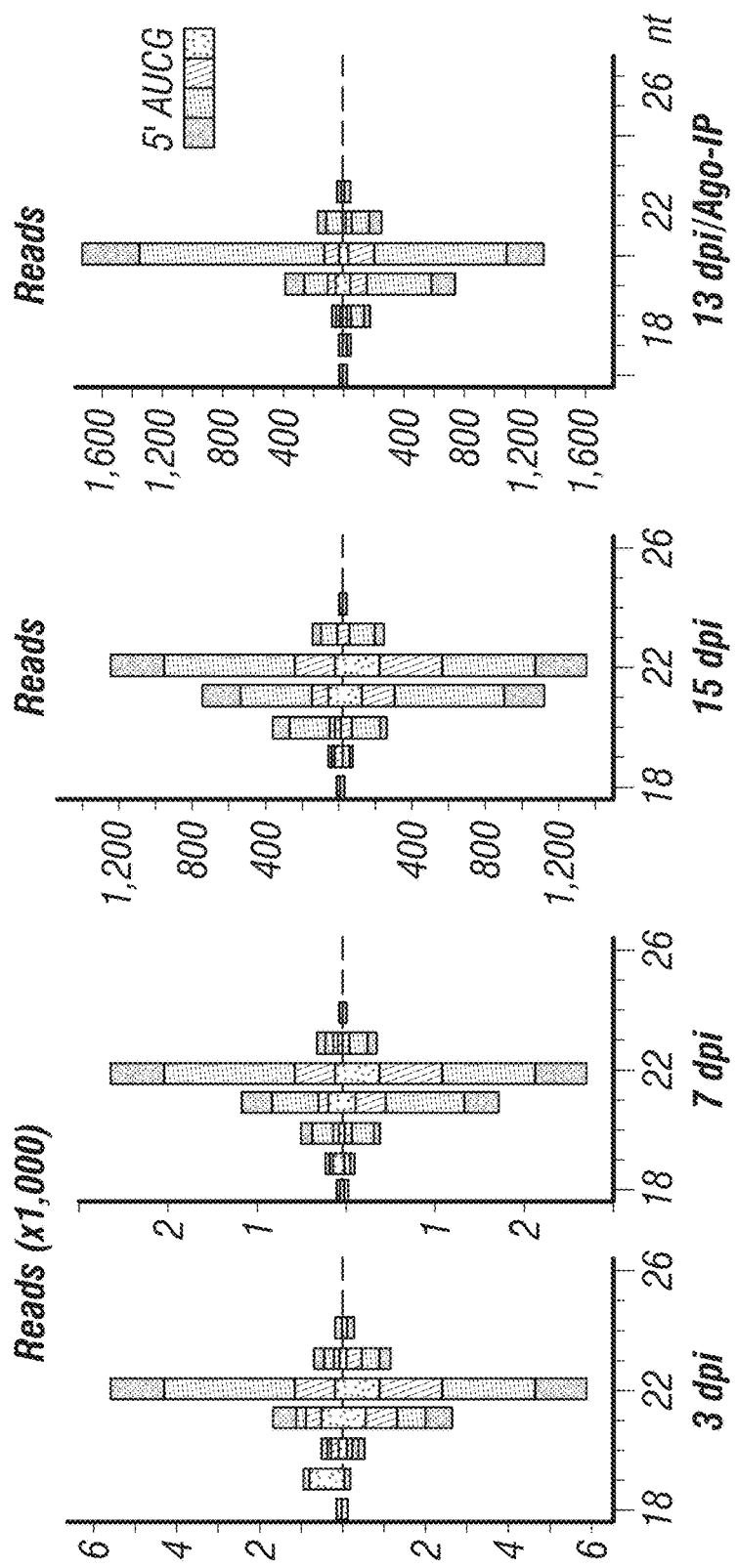
FIG. 15 presents the length distribution and the 5'-terminal nucleotide preference (indicated by colors) of the total positive (top) and negative (bottom) strand viral siRNAs from suckling mice 3, 7 or 15 days post-infection (dpi) with NoVΔB2 and of the viral siRNAs sequenced from Ago complexes co-immunoprecipitated by anti-pan Ago antibodies at 3 dpi from NoVΔB2-infected suckling mice (left 4 panels). The relative abundance of viral siRNAs in each library is normalized as reads per million mouse miRNAs. Shown at the right panel are the genome-wide distribution patterns of 21- to 23-nt positive (red) and negative (blue) strand viral siRNAs from NoVΔB2-infected suckling at 3 dpi before (top) and after (bottom) co-immunoprecipitation with Ago proteins. The genome organization and B2 expression strategy (via a subgenomic RNA) of NoV are shown.
Figure 15:
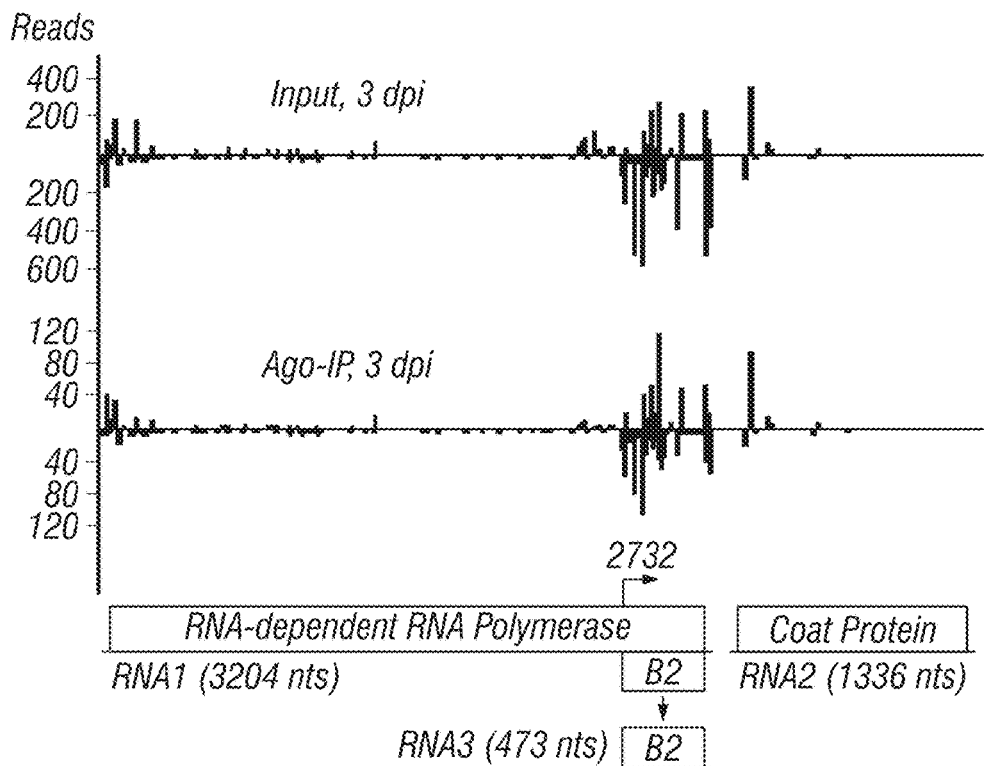

The total small RNAs from NoVΔB2-inoculated suckling mice at 3, 7 and 15 dpi and total small RNAs co-IPed by the anti-pan Ago monoclonal antibody from 3 dpi mice was constructed and sequenced. Analysis of the total viral siRNA in these mice revealed firstly an increased enrichment for viral siRNAs (21~23nt) with 5'-terminal uridine (1U) from 41.8% at 3 dpi, 56.5% at 7 dpi, to 60.5% at 15 dpi (see FIG. 15), all of which are higher than those at 1 (31.1%) and 2 (39.6%) dpi. It was found that the viral siRNAs remained detectable in mice at 15 dpi after NoVΔB2 clearance, but the total viral siRNAs gradually decreased (see FIG. 15) with the 21-23nt negative-strands equivalent to 1.2%, 0.7% and 0.5% of the total mouse miRNAs at 3, 7 and 15 dpi, respectively. Thus, the viral siRNAs at 15 dpi remain more abundant than ≥0.1% of the total miRNA population, the cut-off expression levels proposed for functionally relevant miRNAs. Since presence of multiple miRNA-binding sites enhances miRNA silencing of target genes, genome-wide targeting by siRNAs would predict highly effective antiviral RNAi. Interestingly, compared to 22-nt viral siRNAs, the relative content of 21-nt viral siRNAs increased in suckling mice over the time course from 1 to 15 dpi (see FIG. 15). The results indicate selective loading and/or stability of viral siRNAs in AGOs since 1U is a conserved feature of mammalian miRNAs and 21-nt is the preferred length for synthetic siRNAs in mammalian knockdown experiments. Moreover, deep sequencing verified in vivo Ago loading of viral siRNAs and the specific enrichment for 1U viral siRNAs in Ago complexes (see FIG. 15). It was also found similar distribution patterns of hot spot viral siRNAs over the two viral genomic RNAs in total input and Ago-coIPed complexes (see FIG. 15). Therefore, the small RNA libraries proposed are examined to determine if 21-nt viral siRNAs become more abundant in Ago complexes at later time points and if the additional 21-nt viral siRNAs are either due to 1-nt trimming at the 5' or 3' termini of the dominant 22-nt species or correspond to new species produced later during antiviral RNAi. A systematic view is generated from the population structure, relative abundance and persistence, selective loading and stability of viral siRNAs in mice at distinct stages of antiviral RNAi.

Figure 16:
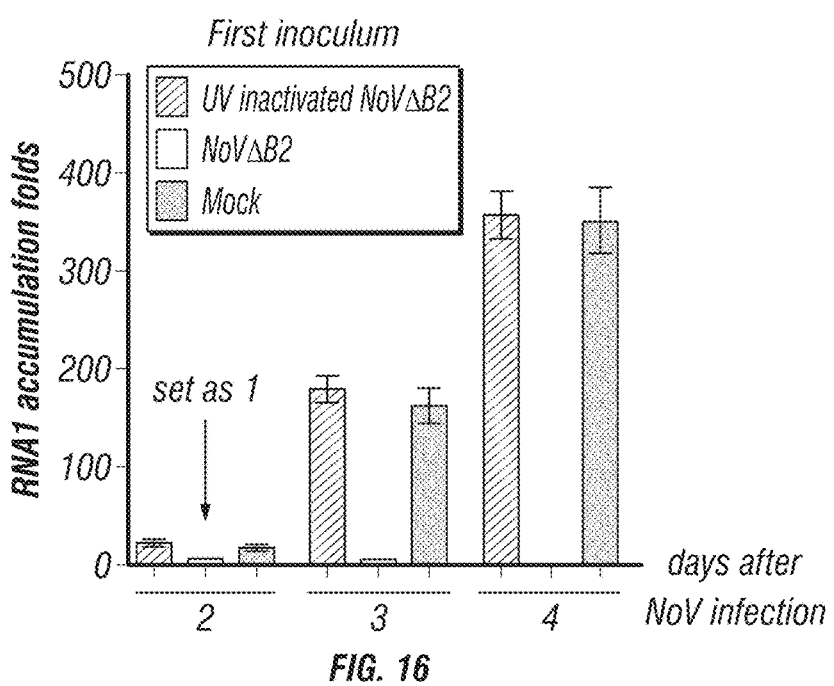
FIG. 16 presents the accumulation of NoV (shown as RNA-1 accumulation) folds by qRT-PCR in suckling mice 2, 3 or 4 days post NoV challenge after pre-inoculation with buffer, NoVΔB2 or UV-inactivated NoVΔB2.
Figure 17:
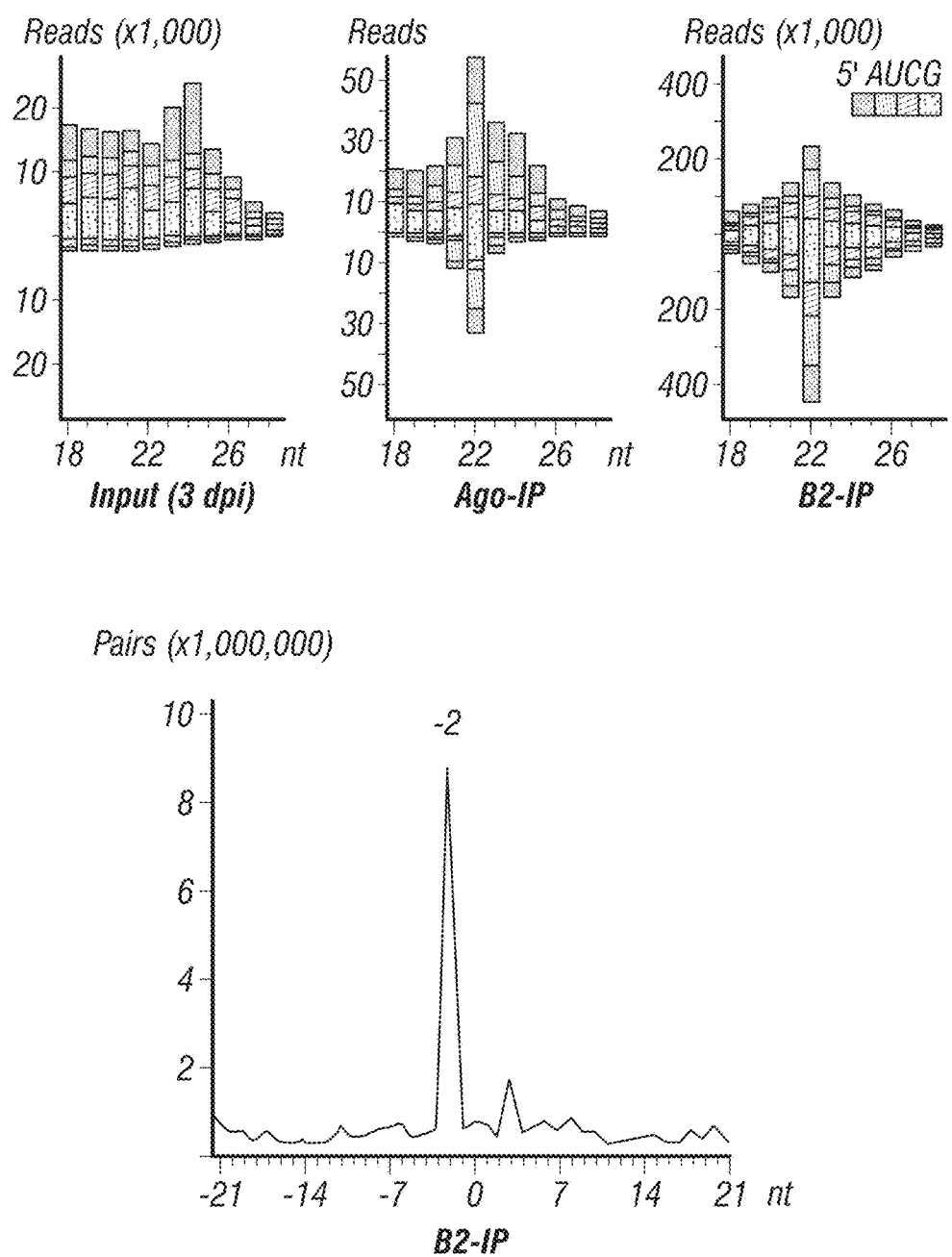
FIG. 17 shows that NoV B2 sequesters viral duplex siRNAs and suppresses their loading into Ago complexes. The relative abundance (reads per million mouse miRNAs), length distribution and the 5'-terminal nucleotide preference of the total positive (top) and negative (bottom) strand viral siRNAs from suckling mice 3 days post-infection (dpi) with NoV and those from Ago and B2 complexes. 22-nt viral RNAs in B2 complexes were enriched for canonical siRNAs shown as a peak at −2 position
Figure 18A:
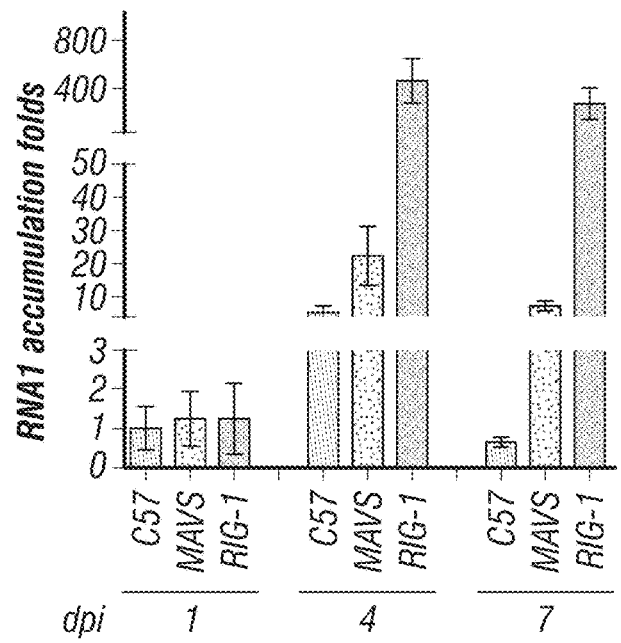
FIG. 18A-B shows that the aaccumulation of NoVΔB2 shown as RNA-1 accumulation folds by qRT-PCR (in the hind limp tissues of wt (C57) or MAVS/RIG-I knockout suckling mice 1, 4 or 7 days post inoculation (dpi) by I.P. (A). The RNA-1 level in C57BL/6 at 1 dpi was set as 1. (B) The relative abundance (reads per million mouse miRNAs), length distribution and the 5'-terminal nucleotide preference of the total positive (top) and negative (bottom) strand viral siRNAs from wt and knockout suckling mice at 4 dpi with NoVΔB2.
Figure 18B:
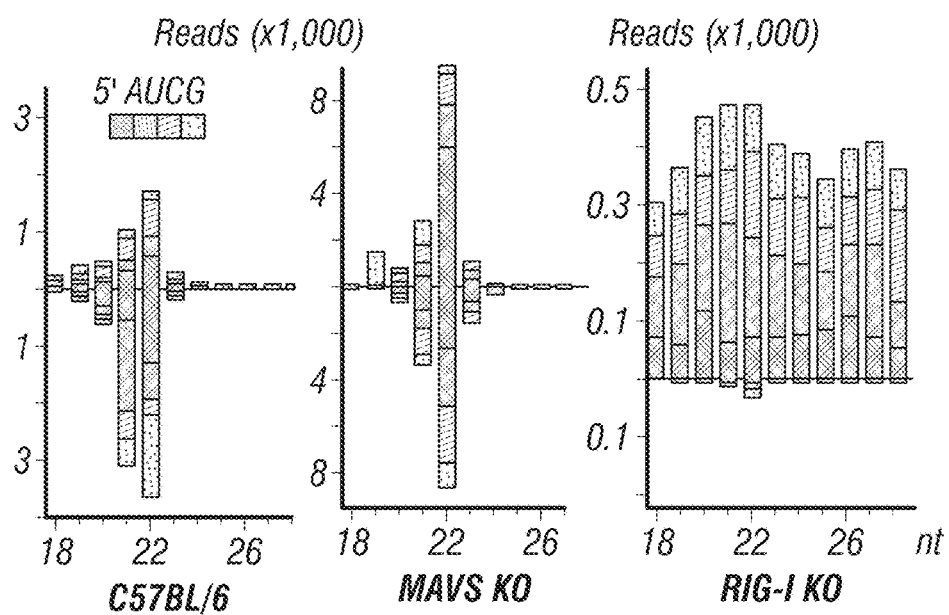
Figure 19:
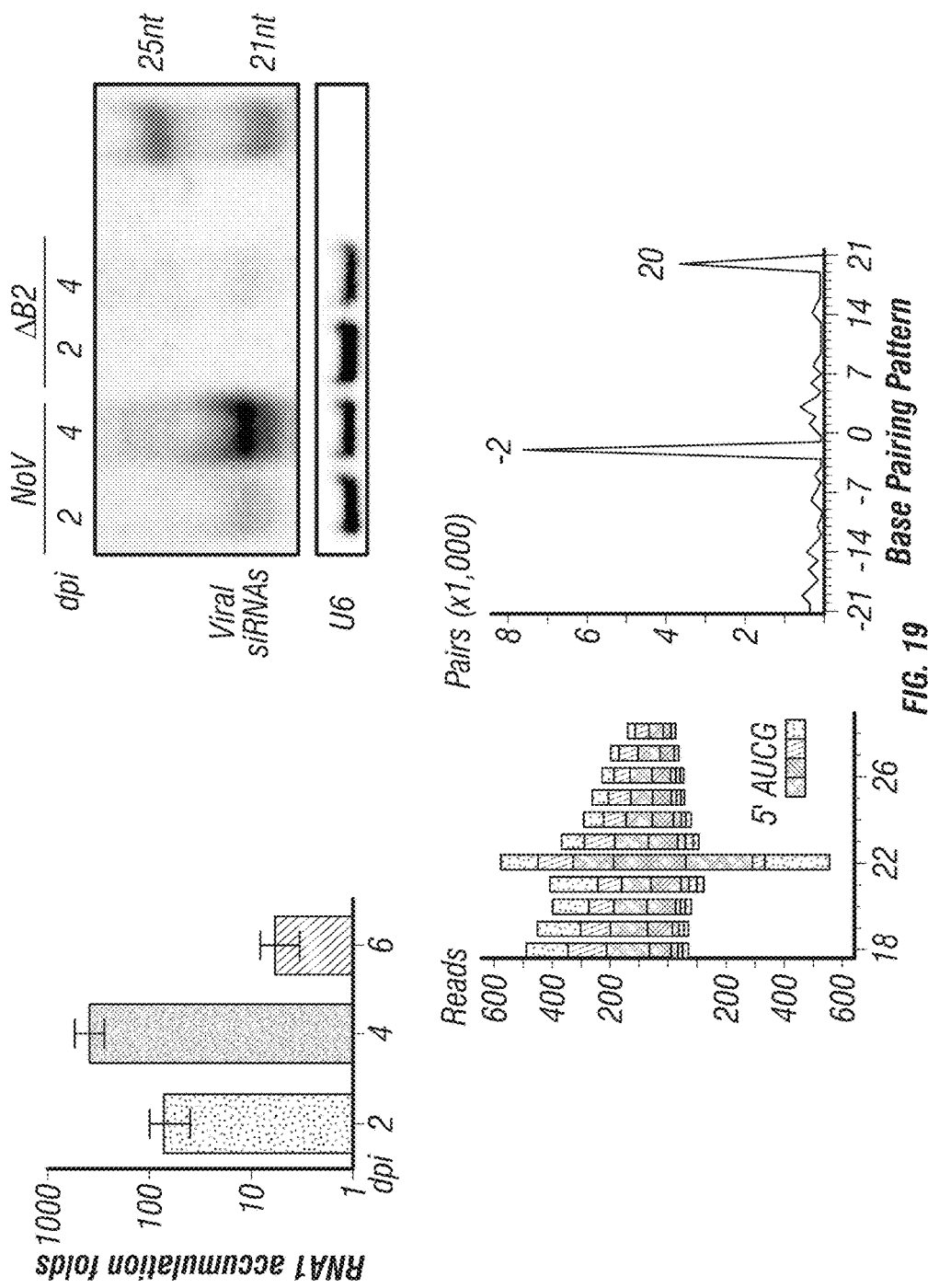
FIG. 19 provides for the characterization of NoV infection in adult mice. The $1^{st}$ panel from left showed the accumulation of NoV in young adult mouse hind limb tissues at 2, 4 and 6 dpi measured by real-time RT-PCR detection of the viral RNA1 (with the accumulation level of NoVΔB2 at 1 dpi in the hind limb set as 1). The $2^{nd}$ panel from left showed Northern blot detection of negative-strand viral siRNAs in young adult mouse hind limb tissues at 2 and 4 dpi with NoV or NoVΔB2 (ΔB2). The same filter was also probed for U6 RNA as a loading control. Synthetic 21- and 25-nt single-stranded RNAs were used as size markers. The $3^{rd}$ panel from left showed the relative abundance (reads per million mouse miRNAs), length distribution and the 5'-terminal nucleotide preference of the total positive (top) and negative (bottom) strand viral siRNAs from 6-week old Balb/c mice at 4 dpi with NoV. The right panel showed that the 22-nt viral RNAs from NoV-infected adult mice were enriched for canonical siRNAs shown as a peak at −2 position.

The density of viral siRNAs was the highest to target the 5'-terminal region of the viral genomic RNA-1 in *Drosophila* cells infected by FHVΔB2. Similar distribution patterns of viral siRNA hot spots were found in mouse ES cells infected by NoVΔB2. Interestingly, it was found higher densities of viral siRNAs to target the subgenomic RNA3-coding region of RNA-1 than the 5'-terminal viral siRNAs in NoVΔB2-infected BHK-21 cells and suckling mice. It is possible that RNA-3 transcriptional initiation internally from the negative-strand RNA1 templates triggers more efficient Dicer recognition and processing of the resulting viral dsRNA than the synthesis of the progeny positive-strand RNA1. The profiles of viral siRNAs in suckling mice infected by NoV mutants that do not produce or produce reduced levels of RNA-3 are determined, which was previously characterized for NoV/FHV.

siRNAs Confer Homology-Dependent Resistance Against Secondary Virus Infection:

The findings indicate that mammalian antiviral RNAi is mediated by the viral siRNAs produced de novo in response to NoVΔB2 infection. One approach to demonstrate the RNA silencing activity of the viral siRNAs is to determine if they confer immediate homology-dependent resistance against secondary infection, known as cross-protection in plants. As part of the proof-of-concept experiments, 6-day old mice were inoculated with NoVΔB2 as described, and two days later, challenged the mice with a lethal dose of NoV. NoV and NoVΔB2 differ only by three nucleotides so that most of NoVΔB2-derived siRNAs should be able to target NoV for RNAi. It was found that all of the 5 suckling mice pre-inoculated as controls with either buffer (mock) or UV inactivated NoVΔB2 accumulated high virus titers and developed hind limb paralysis 4 days after secondary inoculation by NoV before death by 5 dpi (see FIG. 16). By contrast, none of the 10 suckling mice pre-inoculated with NoVΔB2 supported detectable infection of NoV at 2, 3, and 4 dpi (FIG. 3), or exhibited any signs of disease up to 4 weeks after NoV challenge, indicating that pre-inoculation with NoVΔB2 provides immediate protection to suckling mice against secondary lethal infection by wildtype NoV.

Experiments to determine if suckling mice become protected against wt NoV infection 1, 3, 4, 6 and 8 days after inoculation with NoVΔB2 are provided as follows. Three 6-day old mice are inoculated with NoVΔB2 or UV inactivated NoVΔB2 and used for challenge inoculation with NoV at each of the 5 time points. 4 and 6 days after NoV inoculation, one mouse is sacrificed and the musculature of fore and hind limbs is frozen for extraction of RNAs and proteins whereas the third mouse is kept until 4 weeks after NoV inoculation when it is also sacrificed for RNA and protein extraction. Each experiment is repeated for two additional times. Virus titers at each time point are measured by qRT-PCR using β-actin mRNA as the internal control. Western blotting is used to detect the B2 protein in the singly and doubly inoculated mice, which serves to (i) verify the genotypes of NoV and NoVΔB2, (ii) monitor potential reversion of NoVΔB2 in the infected mice, and (iii) specifically determine the accumulation of NoV in the mice pre-inoculated with NoVΔB2. The experimental design ensures that both the survival rate and virus load data are obtained from independent biological replicates, but the number of mice are increased in each repeat if significant variation is detected between the replicates. These experiments determine if the sterilizing immunity is induced in suckling mice 24 hours after NoVΔB2 pre-inoculation, and/or remains effective 8 days after pre-immunization when NoVΔB2 is cleared. The accumulation of viral siRNAs by small RNA is analyzed by Northern blotting and time-course analysis of the viral siRNAs in NoVΔB2-infected mice is determined by deep sequencing so as to verify that protection is correlated with the abundance of the viral siRNAs.

Determining Whether Mammalian RNAi Antiviral Immunity Triggers Sequence-Specific RNAi:

Another approach to characterize the RNA silencing activity of the viral siRNAs is to determine if virus infection triggers homology-dependent RNA silencing of a cellular mRNA reporter, known as virus-induced gene silencing (VIGS) in plants and invertebrates. The viral siRNAs accumulate to ~1-2% of total cellular miRNA population in NoVΔB2-infected mice and are likely to mediate specific RNAi as synthetic siRNAs delivered in vivo. FHV RNA replication in BHK-21 cells without B2 expression was recently found to induce translational inhibition and formation of cytoplasmic granules, which may be mediated by the viral siRNAs since Argonaute-2 is localized in similar granules.

A luciferase mRNA containing 100-nt viral sequence is inserted in the 3'-untranslated region by an adeno-associated virus (AAV)-based vector and assayed for sequence-specific RNAi in NoVΔB2-infected suckling mice. An AAV vector with the capsid from serotype 8 has been engineered for lifelong stable in vivo expression of luciferase driven by a modified cytomegalovirus (CMV) promoter through single muscle injection. The unique BamHI site after the stop codon of the luciferase ORF in the AAV vector, pVIP-CMV-Luciferase-W-SV40, is used for cloning the 100-nt sequence from the 5'-terminal and RNA3-coding regions of the viral RNA1, or from the eGFP coding sequence as control. High density of viral siRNAs targeted these regions of viral RNA1 as shown by deep sequencing in NoVΔB2-inoculated suckling mice. Sensor AAV virus particles are produced, purified, and titrated in 293T cells co-transfected with the AAV backbone vector together with helper vectors pHELP and pAAV2/8 SEED as described. $1\times10^{11}$ genome copies of each AAV strain in a 40 μl volume are injected into the gastrocnemius muscle of mice previously inoculated with NoV or NoVΔB2. Bioluminescent imaging determines if the presence of the viral sequence specifically inhibits the expression of luciferase from the delivered chimeric luciferase mRNA in the viral siRNAs-producing mice.

The AAV delivery system addresses several key questions on the silencing activity of the mouse viral siRNAs produced in vivo. First, the sensor and control AAV particles are injected into uninfected mice (to verify reporter expression) or mice 2, 4, 7, 15 or 28 days post infection with NoVΔB2 in suckling mice. Comparing luciferase expression in these mice determines if and how long the luciferase sensor can be silenced and if the silencing activity is correlated with the abundance and population properties of the viral siRNA population and/or with the sterilizing immunity against wt NoV in suckling mice induced by NoVΔB2 inoculation. Second, the new AAV system maintains high level luciferase expression for more than 60 weeks after vector administration. How long the luciferase expression remains inhibited is determined after vector administration and the correlation of luciferase silencing with virus clearance and/or the accumulation level and population properties of viral siRNAs is determined. Third, silencing of the sensor luciferase mRNAs that contain the positive- or negative-strand viral sequences is compared to determine if positive and negative strand viral siRNAs are similarly effective in silencing cellular mRNA. Fourth, whether B2 expression interferes with VIGS in mice is determined by comparing luciferase expression between NoV and NoVΔB2 infections. The positive-strand mRNAs of RNA viruses appear to be susceptible to synthetic siRNAs in mammals although both polarities of plant viral siRNAs are capable of targeting complementary cellular mRNAs for silencing. VSRs usually do not block VIGS in plants possibly because cellular mRNAs are more susceptible to RNAi compared to the replicating viral RNAs.

Two successive pairs of 22-nt siRNAs targeting the 5'-terminal region of RNA1 (listed below) are among the most abundant cloned from NoVΔB2-inoculated suckling mice. The 2-nt 3' overhangs are highlighted by red and the numbers indicate the corresponding positions of the first and last nucleotide of each siRNA in the viral positive-strand (top, counting from the 5' end) or negative-strand (bottom, counting from the 3' end) RNA-1, with read numbers of each siRNA given in the bracket.

```
                                  (SEQ ID NO: 47)
(14)4-UUGAAUCCAAAACUCAAAAUGC-25

26-UGAACUACGAGACAAUCAUCAA-47 (229)

(SEQ ID NO: 48)
(375) 2-AUAACUUAGGUUUUGAGUUUUA-23

24-CGACUUGAUGCUCUGUUAGUAG-45 (716)
```

As the first step to determine the mechanism of viral siRNAs-directed RNA silencing in mice, AAV-Luc-$R_1$50 is constructed by inserting into the AAV-luciferase sensor the 5'-terminal 50-nucleotide sequence of the viral positive-strand RNA1,

```
                                  (SEQ ID NO: 49)
5'-GUAUUGAAUCCAAAACUCAAAAUGCUGAACUACGAGACAAUCAUCAA

CGG-3'
```

(the highlighted sequences are complementary to the two negative-strand viral siRNAs shown above). A randomized sequence of the same length and nucleotide composition is also inserted into the same position of the AAV-luciferase sensor as the control. Silencing of luciferase from AAV-Luc-$R_1$50, but not from the control sensor, indicates specific silencing activity of the first (nt 2-23) and/or second (nt 24-45) negative-strand viral siRNA in the infected mice. Mutations are further introduced to the 50-nt viral sequence in AAV-Luc-R150.

Determining the Role of AGOs in the RNAi-Mediated Immunity in Mice.

Four members (Ago1-4) in the Argonaute subfamily of mammalian AGOs have overlapping functions in miRNA silencing. Although Ago2 is the only AGO with the slicer activity and essential to mount an experimental response to synthetic siRNAs, miRNAs are randomly sorted to individual Argonautes in mammals, independent of the slicer activity. When Argonautes are ablated constitutively in mice, only the loss of Ago2 causes embryonic lethality, whereas single, double or triple losses of Ago1, Ago3, or Ago4 have no major impact on animal development. AGOs essential for RNAi-mediated antiviral immunity in plants and invertebrates retain the slicer activity, suggesting an antiviral role for Ago2. However, it was found that only two AGOs control antiviral silencing against the positive-strand RNA virus cucumber mosaic virus in *Arabidopsis* after examining 25 single, double and triple knockout mutants of nine distinct AGO genes, suggesting specificity of the AGO function in the defense response. The detection of in vivo Ago loading of viral siRNAs in the studies presented herein suggest an in vivo function of AGOs in mammals, which is investigated using the established NoV/mouse model.

Suckling mice knockout (KO) is infected singly for Ago1, Ago3 and Ago4 as well as double KO for Ago1/3 and triple KO for Ago1/3/4 by NoVΔB2, and determined if any of the KO strains losses virus resistance, accumulates higher virus titers, and/or develops signs of disease in contrast to wt littermate control mice. Since only Ago2 is functional in the triple KO strain, it can be concluded if Ago2 alone is sufficient for antiviral RNAi in mice as found in mES cells. Ago2 knockout mouse embryonic fibroblasts (MEFs) are used to determine if loss of Ago2 alone or its slicer activity is sufficient to rescue NoVΔB2 infection found in mouse ES cells. If differences are observed in virus susceptibility, the population of the total and Ago-loaded viral siRNAs is characterized in these mice to find out if loss of one, two or three AGOs has impact on the biogenesis of viral siRNAs. In addition, KO strains are used to determine (i) if NoVΔB2 inoculation in suckling mice induces sterilizing immunity against wt NoV and (ii) if the chimeric luciferase mRNA sensor is silenced in NoVΔB2-infected suckling mice.

Characterizing RNAi Suppression During Wt NoV Infection of Suckling Mice.

An in vivo model for understanding viral suppression of RNAi in the context of infection and infection-induced production of the cognate viral siRNAs is investigated. The findings indicate that NoV B2 suppresses the processing of long viral dsRNA into siRNAs in vivo as suggested by in vitro studies. However, it remains unclear if there is a physiological role for the observed in vitro activity of B2 to bind siRNA duplexes. Libraries of small RNAs co-immunoprecipitated by antibodies specific to either NoV B2 protein or mouse Argonautes from the hind limp tissues of suckling mice 3 days after NoV infection are constructed and sequenced (see FIG. 17). It was found that B2 formed complexes in vivo with NoV-derived small RNAs, which showed about equal ratios of positive and negative strands and were enriched with 22-nt small RNAs. Notably, the 22-nt viral RNAs found in B2 complexes exhibited canonical properties of siRNA (20nt perfect duplex region with 2-nt 3'-overhangs), but did not show 1U preference (see FIG. 17). Argonaute complexes in NoV-infected mice also contained 22-nt viral siRNAs (see FIG. 17), which compared to those from NoVΔB2-infected mice (see FIG. 15), however, were >30-fold less abundant after normalization by the miRNA content and did not show 1U preference. These findings indicate that B2 sequestered viral siRNA duplexes and inhibited their loading into Argonaute complexes in vivo. Presence of viral siRNA duplexes in B2 complexes in NoV-infected mice also demonstrate that B2 suppression of long dsRNA processing is incomplete, suggesting importance of dual modes of RNAi suppression in the viral counter defense.

The dual modes of RNAi suppression by NoV B2 require in addition to its dsRNA-binding activity, B2 to directly interact with the viral RNA-dependent RNA polymerase (RdRP) and/or any component of the host Dicer/RISC complex. Studies in *Drosophila* cells (see FIG. 14) indicate that such protein-protein interactions may enhance B2 access to the nascent viral dsRNA replicative intermediates either before or during their recognition by the antiviral Dicer. VSR as a structural component of the viral replication complex is known in certain plant viruses and direct interaction with the host dicing complex may suggest a viral adaptation strategy for potent inhibition of host dicing. Antibodies are generated to NoV RdRP and coat protein and Western blotting, co-IP and proteomics approaches are used to determine if B2 interacts in vivo with any other viral protein or with a component of the mouse RNAi pathway, including Dicer, TRBP, PACT, and AGO for which commercial antibodies are available. NoVmB2, which encodes a mutant B2 (R59Q mutant) defective in dsRNA-binding, is used to determine if dsRNA-binding is important for possible protein-to-protein interactions. Mutations are introduced into the genome of NoV to determine if specific C-terminal regions of B2 beyond the N-terminal dsRNA-binding domain are important for the protein interactions and its dual modes of RNAi suppression as described above.

The antibodies are also used with viral RdRP to titrate infectious NoV and NoVΔB2 in BHK-21 and BHK-B2 cells by immunofluorecence staining since NoV is noncytopathic. However, B2's dsRNA binding activity is also involved in the suppression of IFN-dependent antiviral responses although the dsRNA-binding B2 protein of a fish nodavirus does not block induction of interferon in fish cells. In 293T cells, co-transfection of a B2-expression plasmid with the reporter plasmid p-125Luc expressing luciferase from the natural INFβ promoter before Sendai virus infection is used to induce IFN signaling. An alternative strategy is to produce stable 293T cells expressing wt B2 or mutant B2(R59Q) and then assay for the suppression of IFN signaling in the stable cells in which expression levels of wt and mutant B2 proteins are verified by Western blotting.

Determining the Role of the Known dsRNA Sensors in Antiviral RNAi.

It is well established that diverse RNA viruses are targeted in mammals by a closely-related family of 3 RIG-I-like receptors (RLRs), including RIG-I, MDA5 and LGP2, which detect virus-specific dsRNA in the cytosol. In this form of innate immunity, recognition of viral dsRNA by the C-terminal domain of RLRs triggers the MAVS-dependent signaling cascade that leads to the production of type 1 IFNs. Recognition of viral dsRNA also occurs in the endosome by Toll-like receptor 3 (TLR3). Interestingly, *C. elegans* nematodes, which do not produce IFNs, encode a family of three RLRs, referred as Dicer-related helicase (DRH) 1 to 3, of which DRH-1 and DRH-3 are important for antiviral RNAi by regulating the biogenesis of the primary and secondary viral siRNAs, respectively. Based on their dsRNA-sensing activity in mammals and antiviral RNAi activity in nematodes, it is hypothesized that the mammalian dsRNA-sensing RLRs play a role in the initiation of RNAi-mediated antiviral immunity.

NoVΔB2 was inoculated into 7-day-old RIG-I and MAVS knockout mice by intraperitoneal injection (I.P.) using wild-type C57BL/6 mice (WT) as controls (see FIG. 18). There was rapid virus clearance in WT C57BL/6 mice as was previously found in Balb/c mice. NoVΔB2 was also gradually cleared in MAVS knockout mice, but accumulated to >300-fold higher levels in RIG-I knockout mice than in C57BL/6 mice at 7 dpi. Virus clearance in C57BL/6 mice and MAVS knockout mice was also associated with abundant production of 21-23nt viral siRNAs. Strikingly, RIG-I knockout mice exhibited a severe defect in the production of the canonical viral siRNAs even though without B2 suppression of dicing, viral dsRNA replicative intermediates from robust virus replication are expected to be processed into abundant siRNAs. These findings revealed a new, MAVS-independent activity of RIG-I in the biogenesis of viral siRNAs during the antiviral RNAi response of mice to NoVΔB2 infection.

The role and mechanism of the known mouse dsRNA sensors in antiviral RNAi is investigated. Virus infection and viral siRNA production in RIG-I, MAVS, LGP2, MDA5, TLR3 single knockout mice is compared on days 1, 4, 7, 14 and 28 after inoculation with NoV, NoVΔB2, or NoVmB2. These analyses will also indicate if C57BL/6 mice consistently produce higher content of 21-nt viral siRNAs (see FIG. 18). MDA5 and RIG-I double knockout mice are determined if they exhibit enhanced susceptibility to NoV and its mutants. Since viral siRNAs are detectable 6 hours post-infection (hpi), the early growth phenotypes of NoV and its mutants in wildtype and knockout mouse MEFs 0, 6, 12, 18, 24, 30, 36, 42 and 48 hpi are compared. It is known that human Dicer is found in a complex with dsRNA-binding protein partners TRBP and PACT for optimal activity in RNAi and previous studies detected protein interactions between PACT and RIG-I and between Dicer and LGP2. Accordingly, RIG-I is examined to see if it interacts with Dicer and/or TRBP/PACT to recruit the non-self viral dsRNA for dicing into siRNAs using Western blotting, co-IP and proteomics approaches under in vitro and in vivo infection models. Moreover, these knockout strains are used to determine (i) if NoVΔB2 inoculation in suckling mice can still induce sterilizing immunity against wt NoV and (ii) if the chimeric luciferase mRNA sensor can still be silenced in NoVΔB2-infected suckling mice.

Determining if Type 1 IFNs Regulate Antiviral RNAi.

Since RIG-I is one of the IFN-stimulated genes (ISGs), it is possible that the IFN signaling pathway regulates the new activity of RIG-I in the biogenesis of viral siRNAs. In the canonical type I IFN-induced signaling pathway, engagement of IFNs by IFN-α receptor (IFNAR) activates Janus kinase 1 and tyrosine kinase 2, which phosphorylate the latent cytoplasmic STAT1 and STAT2. Phosphorylated STAT1 and STAT2 dimerize, translocate to the nucleus, and assemble into ISG factor 3 complex to activate the transcription of ISGs, some of which may establish a cellular antiviral state by controlling the biogenesis and activity of viral siRNAs.

The role of IFN signaling in antiviral RNAi is determined by performing NoV/NoVΔB2 infection studies in IFNAR, STAT1 and STAT2 knockout suckling mice using wildtype C57BL/6 mice (WT) as controls. If loss of an IFN signaling component enhances mouse susceptibility to NoV or NoVΔB2, it will be further determined if the knockout gene influences the biogenesis, population structure and Ago loading or the silencing activities of viral siRNAs. Northern and Western blotting analyses are used to monitor potential differences in the induction of RIG-I. If IFNAR/STAT1/STAT2 knockout enhances NoVΔB2/NoV susceptibility without altering the biogenesis or activity of viral siRNAs, IFN signaling would not play a regulatory role in antiviral RNAi. If these analyses indeed indicate a regulatory role of IFN signaling in antiviral RNAi, the growth of NoV and NoVΔB2 in MEFs of the wildtype and knockout mouse strains will be analyzed before and after treatment with type 1 IFNs. If IFN pre-treatment potentiates antiviral RNAi in RIG-I-dependent manner, it is possible that enhanced production of viral siRNAs may de-repress B2 suppression and render wildtype MEFs resistant to NoV.

Characterizing Adult Mice Resistance to NoV Infection:

Although NoV lethally infects suckling mice, older mice such as those 21 days after birth survive viral inoculation with little or no paralysis or other signs of disease. 6-week old mice are inoculated with NoV and it was found that NoV replicated to moderate levels in mouse hind limb tissues at 2 and 4 dpi, but was reproducibly cleared in the same tissues by 6 dpi (see FIG. 19). Northern analysis indicated that NoV clearance in the young adult mice was associated with production of negative-strand viral siRNAs that appeared as a strong discrete band at 22 nucleotides at 4 dpi (see FIG. 19). By comparison, NoVΔB2 induced lower level accumulation of viral siRNAs in adult mice because it replicated to extremely low levels and thus would produce fewer dsRNA molecules for dicing. Thus, although wt NoV was lethal to suckling mice where production of viral siRNAs was suppressed, it was rapidly cleared in young adult mice in a process associated with the production of abundant viral siRNAs (see FIG. 19). The total small RNAs were sequenced in NoV-infected adult mice at 4 dpi and the results showed that NoV infection indeed triggered abundant production of canonical viral siRNAs, equivalent to 0.2% of total cellular miRNA reads (see FIG. 19). Strikingly, 71.5% of the total 22-nt negative-strand siRNAs of NoV corresponded to the two pairs of the previously identified 5'-terminal siRNAs of RNA1, which is similar to the pattern detected in NoVΔB2-infected mouse ES cells. By comparison, the same 2 pairs of the 5'-terminal siRNAs of NoVΔB2 were much less abundant in suckling mice, representing 11.7%, 1.9% and 1.5% of the total 22-nt negative-strand siRNAs of NoVΔB2 from suckling mice at 3, 7 and 15 dpi, respectively. These results indicate that the same sets of viral siRNAs are processed by the host Dicer in both suckling and adult mice, but dicing occurred primarily at the three positions to release the 2 pairs of siRNAs in adult mice even through NoV encodes the B2 gene Production of abundant viral siRNAs indicates that NoV fails to suppress viral siRNA biogenesis in adult mice unlike in suckling mice.

First, it was determined if the population structure, relative abundance and persistence of viral siRNAs in young adult mice by profiling total small RNAs from 6-week old mice 1, 2, 3, 4, 6, 8, 14, or 28 days post infection with NoV or NoVΔB2. The same set of RNA samples are also used for qRT-PCR analysis to document the time-course virus accumulation in adult mice after inoculation. Second, it is determined if the viral siRNAs are active in directing sequence-specific RNAi in NoV-infected adult mice using a sensor mRNA containing the 5'-terminal 50-nt sequence of NoV RNA1. The specific RNAi is analyzed depending on the abundance of the viral siRNAs at the later time points when NoV is completely cleared. Third, whether adult mice confer NoV resistance by directing an enhanced RIG-I-dependent biogenesis of viral siRNAs was investigated. 6-week old RIG-I, MDA5, LGP2, MAVS, IFNAR, STAT1 and STAT2 knockout mice as well as wt C57BL/6 mice are inoculated with NoV and characterized as described above. These experiments illustrate that enhanced NoV susceptibility is observed in the knockout mouse strains and is associated with loss or greatly reduced production of canonical viral siRNAs, and MAVS plays a more important role in the control of NoV or NoVΔB2 in adult mice than that observed in suckling mice (see FIG. 18). It is possible that induction of type 1 IFN production and IFN signaling is much stronger in adult mice than that observed previously in suckling mice. The possible differential induction of RLRs and IFNβ in suckling and adult mice before and after infection with NoV or NoVΔB2 is characterized by Northern and Western blotting analyses or total RNA-seq analysis. Fourth, production of the extremely abundant siRNAs to target the 5'-terminal region of RNA1 in both NoV-infected adult mice and NoVΔB2-infected mouse ES cells suggest an alternative idea, although not mutually exclusive to the enhanced antiviral RNAi hypothesis, that NoV loses its B2 function during adult mouse infection. For example, adult mice may direct reduced expression or enhanced turnover of the B2 protein or that B2 becomes inactive to suppress dicing and/or to sequester viral duplex siRNAs during adult mouse infection. The accumulation of NoV RNA1, RNA3 and B2 protein between suckling mice and adult mice is compared and sequenced. Small RNAs co-IPed with B2 from adult mice 1, 2, 3 and 4 days after NoV inoculation to find out if B2 sequesters perfect duplex viral siRNAs in adult mice. It will be determined if B2's interaction with viral RdRP or other host RNAi components is altered in adult mice.

Summary of Findings:

First, the findings demonstrate production of canonical viral siRNAs during infection in mammals. It was found that infection of cultured baby hamster kidney 21 (BHK-21) cells by the B2-deificient mutant of NoV (NoVΔB2) triggered accumulation of viral siRNAs as shown by deep sequencing. These viral siRNAs were predominantly 22-nt (more obvious for the negative-strands), were enriched for a population of 22-nt RNA pairs containing a 20-nt perfectly base-paired duplex region with 2-nt 3' overhangs, and included a more dominant population with patterns indicative of successive siRNA processing from the same viral dsRNA precursor. In contrast, viral small RNAs from wildtype NoV-infected BHK-21 cells did not exhibit properties of canonical siRNAs, indicating that B2 expression inhibited the biogenesis of viral siRNAs. Deep sequencing also revealed production of predominantly 22-nt, successive (also referred as "phased") viral siRNAs in mouse embryonic stem (ES) cells infected by either EMCV or NoVΔB2, but not by wildtype NoV. Moreover, siRNAs targeting EMCV became undetectable in Dicer knockout mouse ES cells, thus verifying the Dicer-dependent biogenesis of the viral siRNAs. Notably, predominantly 22-nt viral siRNAs accumulated to abundant levels in the limp tissues of suckling mice two days after intraperitoneal injection with NoVΔB2 and were readily detectable by either deep sequencing or Northern blot hybridization. In contrast, siRNAs targeting NoVΔB2 in BHK-21 cells were below the limit of detection by Northern blotting. These viral siRNAs produced in vivo also exhibited properties of canonical siRNAs and were divided approximately equally into positive and negative strands, indicating that they are processed from viral dsRNA replicative intermediates as shown for FHV siRNAs in Drosophila. Production of canonical viral siRNAs triggered by infection of mammalian cells by both NoVΔB2 and EMCV indicates presence of a conserved antiviral RNAi response to the infection of diverse RNA viruses in mammals. The findings also suggest that robust detection of mammalian viral siRNAs, which was previously unsuccessful, requires the use of in vivo infection models and/or viruses incapable of inhibiting siRNA biogenesis.

Second, EMCV siRNAs were loaded in human Argonaute-2 (hAgo2) stably expressed in mouse ES cells and in mouse Ago2 as shown by both Northern blotting and deep sequencing.

Third, it was found that unlike NoV, NoVΔB2 infection was defective in both BHK-21 cells and mouse ES cells, but was effectively rescued in BHK-21 cells stably expressing either B2 of NoV or a heterologous VSR, which is known to suppress experimental RNAi in mammalian cells. NoVΔB2 infection was also defective in hAgo2-expressing mouse ES cells after knockout of the four mouse endogenous Argonautes, but was efficiently rescued after hAgo2 was also depleted. These findings together indicate that in the absence of RNAi suppression, the induced mammalian antiviral RNAi response, characterized by production of 22-nt viral siRNAs, potently suppresses virus infection in an Argonaute-dependent manner. Furthermore, although the difference between NoV and NoVΔB2 accumulation levels in the limp tissues of suckling mice was small at 1 day post inoculation (dpi), it became progressively more pronounced at later infection times so that the accumulation of NoV was more than 1,000 times that of NoVΔB2 by 4 dpi. It was found that a NoV mutant (NoVmB2) expressing a mutant B2 (R59Q), shown defective in RNAi suppression previously, was also attenuated and rapidly cleared in suckling mice in a process associated with production of abundant viral siRNAs detectable by Northern blotting. Therefore, without viral suppression of RNAi, mice are able to launch an antiviral RNAi response sufficiently potent to terminate viral infection. The quantitative RT-PCR analysis on the expression of 84 key genes from the known innate antiviral pathways in suckling mice at 4 dpi detected no major differences between infection by NoVΔB2 and NoV, suggesting that rapid in vivo clearance of NoVΔB2 was not mediated by one of the known IFN-regulated pathways.

The biogenesis and distribution patterns of small RNA derived from ssRNA viruses are thus conserved among infections of plant, invertebrate, and mammalian cells; orthologous VSRs of insect- and mammalian-infecting viruses also suppress DCR action in genetically indistinguishable ways. Therefore, defensive, in addition to possible regulatory, functions likely underpin the evolutionary persistence of catalytic RNAi in mammals. The results provide clues as to why mammalian antiviral RNAi has remained elusive thus far. First, previous studies invariably involved virulent viruses, of which some probably encode VSRs that, like the NoV-encoded B2, prevent production of siRNAs, the diagnostic molecules of antiviral RNAi. Second, virus-derived siRNA levels were at least one order of magnitude higher in undifferentiated than in differentiated mESCs or BHK-21 cells. This probably relates to the distinctive efficacy of long dsRNA-triggered RNAi in undifferentiated cells derived from embryonic or adult tissues, which is possibly underpinned by their generally reduced ability to mount non-sequence specific immune responses, including the IFN response, against long dsRNA. Alternatively, or coincidently, DCR siRNA-processing activity might decrease during cell differentiation, perhaps via modification of its internal autoinhibitory helicase domain. In this context, the identical distribution, relative abundance, and biochemical features of NoVΔB2 siRNAs observed in mESCs and suckling mice suggest that multipotent progenitor cells, which abound in various mammalian tissues, might form the primary and most potent sites of antiviral RNAi in vivo. Nonetheless, long dsRNA-triggered RNAi was reported in somatic myoblasts, or even in fully differentiated myotubes and neural cells despite the possible activation of an IFN response.

A number of embodiments have been described herein. Nevertheless, it will be understood that various modifications may be made without departing from the spirit and scope of this disclosure. Accordingly, other embodiments are within the scope of the following claims.

What is claimed is:

1. A method for reducing likelihood of a subsequent infection by a virus in a mammal, the method comprising administering to the mammal an attenuated form of the virus that lacks a functional viral suppressor of RNA interference (VSR), wherein administration of the attenuated form of the virus that lacks a functional VSR confers resistance against subsequent infection by the virus.

2. The method of claim 1, wherein the attenuated virus comprises one or more mutations in the VSR coding sequence.

3. The method of claim 2, wherein the one or more mutations comprise one or more deletions, insertions, or substitutions.

4. The method of claim 3, wherein the one or more mutations are deletions.

5. The method of claim 1, wherein the VSR coding sequence is deleted in the attenuated virus.

6. The method of claim 1, wherein the attenuated virus is a Nodamura virus, Ebola virus, HIV-1, HIV-2, HCV, HBV, measles virus, influenza virus, papillomavirus, picornavirus, or hepadnavirus.

7. The method of claim 1, wherein the administering step is performed 2 days prior to the mammal being exposed to a virus.

8. The method of claim 1, wherein the mammal is a human.

9. The method of claim 1, wherein the virus is an Ebola virus lacking a functional VP35 gene.

10. The method of claim 1, wherein the attenuated virus is a Nodamura virus lacking a functional B2 gene.

11. The method of claim 1, wherein the attenuated virus further comprises a heterologous polynucleotide sequence.

* * * * *

SEQUENCE LISTING

<160> NUMBER OF SEQ ID NOS: 62

<210> SEQ ID NO 1
<211> LENGTH: 339
<212> TYPE: PRT
<213> ORGANISM: Ebola virus

<400> SEQUENCE: 1

Met Thr Thr Arg Thr Lys Gly Arg Gly His Thr Ala Ala Thr Thr Gln

-continued

```
1               5                   10                  15
Asn Asp Arg Met Pro Gly Pro Glu Leu Ser Gly Trp Ile Ser Glu Gln
            20                  25                  30

Leu Met Thr Gly Arg Ile Pro Val Ser Asp Ile Phe Cys Asp Ile Glu
        35                  40                  45

Asn Asn Pro Gly Leu Cys Tyr Ala Ser Gln Met Gln Gln Thr Lys Pro
    50                  55                  60

Asn Pro Lys Thr Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

Ser Ser Leu Asn Arg Val Cys Ala Glu Met Val Ala Lys Tyr Asp Leu
    130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asp Ser Thr Thr Ser
        195                 200                 205

Leu Thr Glu Glu Asn Phe Gly Lys Pro Asp Ile Ser Ala Lys Asp Leu
    210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys

<210> SEQ ID NO 2
<211> LENGTH: 137
<212> TYPE: PRT
<213> ORGANISM: Nodamura virus

<400> SEQUENCE: 2

Met Thr Asn Met Ser Cys Ala Tyr Glu Leu Ile Lys Ser Leu Pro Ala
1               5                   10                  15

Lys Leu Glu Gln Leu Ala Gln Glu Thr Gln Ala Thr Ile Gln Thr Leu
            20                  25                  30

Met Ile Ala Asp Pro Asn Val Asn Lys Asp Leu Arg Ala Phe Cys Glu
```

```
                    35                  40                  45
Phe Leu Thr Val Gln His Gln Arg Ala Tyr Arg Ala Thr Asn Ser Leu
 50                  55                  60

Leu Ile Lys Pro Arg Val Ala Ala Leu Arg Gly Glu Glu Leu Asp
 65                  70                  75                  80

Leu Gly Glu Ala Asp Val Ala Ala Arg Val Arg Gln Leu Lys Gln Gln
                 85                  90                  95

Leu Ala Glu Leu Glu Met Glu Ile Lys Pro Gly His Gln Gln Val Ala
                100                 105                 110

Gln Val Ser Gly Arg Arg Lys Ala Ala Ala Ala Pro Val Ala Gln
            115                 120                 125

Leu Gly Arg Val Gly Val Val Asn Glu
    130                 135

<210> SEQ ID NO 3
<211> LENGTH: 21
<212> TYPE: DNA
<213> ORGANISM: Artificial Sequence
<220> FEATURE:
<223> OTHER INFORMATION: miR-16

<400> SEQUENCE: 3
gccaatattt acgtgctgct a                                        21

<210> SEQ ID NO 4
<211> LENGTH: 30
<212> TYPE: DNA
<213> ORGANISM: Artificial Sequence
<220> FEATURE:
<223> OTHER INFORMATION: U6 probe

<400> SEQUENCE: 4
gcagggccca tgctaatctt ctctgtatcg                               30

<210> SEQ ID NO 5
<211> LENGTH: 22
<212> TYPE: DNA
<213> ORGANISM: Artificial Sequence
<220> FEATURE:
<223> OTHER INFORMATION: EMCV (+) viRNA probe

<400> SEQUENCE: 5
tatcgagcag actggcaatc cg                                       22

<210> SEQ ID NO 6
<211> LENGTH: 40
<212> TYPE: DNA
<213> ORGANISM: Artificial Sequence
<220> FEATURE:
<223> OTHER INFORMATION: NoV RNA1 and RNA3 probe

<400> SEQUENCE: 6
atcgttgctt gcgtctcctg agccagctgc tccagcttgg                    40

<210> SEQ ID NO 7
<211> LENGTH: 20
<212> TYPE: DNA
<213> ORGANISM: Artificial Sequence
<220> FEATURE:
<223> OTHER INFORMATION: NoV Repllicase forward primer

<400> SEQUENCE: 7
ccgttcatgg cttacacctt                                          20
```

<210> SEQ ID NO 8
<211> LENGTH: 20
<212> TYPE: DNA
<213> ORGANISM: Artificial Sequence
<220> FEATURE:
<223> OTHER INFORMATION: NoV Replicase Reverse primer

<400> SEQUENCE: 8
gcaccagtcc caaacttcat                                              20

<210> SEQ ID NO 9
<211> LENGTH: 24
<212> TYPE: DNA
<213> ORGANISM: Artificial Sequence
<220> FEATURE:
<223> OTHER INFORMATION: SUL Forward primer

<400> SEQUENCE: 9
atatcgaaaa ggctttgaca gaag                                         24

<210> SEQ ID NO 10
<211> LENGTH: 22
<212> TYPE: DNA
<213> ORGANISM: Artificial Sequence
<220> FEATURE:
<223> OTHER INFORMATION: SUL Reverse primer

<400> SEQUENCE: 10
aatctggtct tgaagcttgt cc                                           22

<210> SEQ ID NO 11
<211> LENGTH: 20
<212> TYPE: DNA
<213> ORGANISM: Artificial Sequence
<220> FEATURE:
<223> OTHER INFORMATION: Nov_AAF9_1 RNA1 Forward primer

<400> SEQUENCE: 11
ccgttcatgg cttacacctt                                              20

<210> SEQ ID NO 12
<211> LENGTH: 20
<212> TYPE: DNA
<213> ORGANISM: Artificial Sequence
<220> FEATURE:
<223> OTHER INFORMATION: Nov_AAF9_1 RNA1 Reverse primer

<400> SEQUENCE: 12
gcaccagtcc caaacttcat                                              20

<210> SEQ ID NO 13
<211> LENGTH: 20
<212> TYPE: DNA
<213> ORGANISM: Artificial Sequence
<220> FEATURE:
<223> OTHER INFORMATION: Nov_AAF9_1 RNA2 Forward primer

<400> SEQUENCE: 13
cccaagatgt caaggacgtt                                              20

<210> SEQ ID NO 14
<211> LENGTH: 20
<212> TYPE: DNA
<213> ORGANISM: Artificial Sequence
<220> FEATURE:

<223> OTHER INFORMATION: Nov_AAF9_2 RNA1 Reverse primer

<400> SEQUENCE: 14
tcattatccc ggttgatggt                                          20

<210> SEQ ID NO 15
<211> LENGTH: 20
<212> TYPE: DNA
<213> ORGANISM: Artificial Sequence
<220> FEATURE:
<223> OTHER INFORMATION: Nov_AF17_1 RNA2 Forward primer

<400> SEQUENCE: 15
cagagaatgg cagcaacaaa                                          20

<210> SEQ ID NO 16
<211> LENGTH: 20
<212> TYPE: DNA
<213> ORGANISM: Artificial Sequence
<220> FEATURE:
<223> OTHER INFORMATION: Nov_AF17_1 RNA2 Reverse primer

<400> SEQUENCE: 16
cggtaaaacg agaccctgaa                                          20

<210> SEQ ID NO 17
<211> LENGTH: 20
<212> TYPE: DNA
<213> ORGANISM: Artificial Sequence
<220> FEATURE:
<223> OTHER INFORMATION: Nov_AF17_2 RNA2 Forward primer

<400> SEQUENCE: 17
ttgaatttcc agggttcgac                                          20

<210> SEQ ID NO 18
<211> LENGTH: 20
<212> TYPE: DNA
<213> ORGANISM: Artificial Sequence
<220> FEATURE:
<223> OTHER INFORMATION: Nov_AF17_2 RNA2 Reverse primer

<400> SEQUENCE: 18
tgacccagca aattgcatta                                          20

<210> SEQ ID NO 19
<211> LENGTH: 19
<212> TYPE: DNA
<213> ORGANISM: Artificial Sequence
<220> FEATURE:
<223> OTHER INFORMATION: Actin Forward primer

<400> SEQUENCE: 19
attggcaacg agcggttcc                                           19

<210> SEQ ID NO 20
<211> LENGTH: 21
<212> TYPE: DNA
<213> ORGANISM: Artificial Sequence
<220> FEATURE:
<223> OTHER INFORMATION: Actin Reverse primer

<400> SEQUENCE: 20
agcactgtgt tggcatagag g                                        21

```
<210> SEQ ID NO 21
<211> LENGTH: 24
<212> TYPE: DNA
<213> ORGANISM: Artificial Sequence
<220> FEATURE:
<223> OTHER INFORMATION: EMC 2A Forward primer

<400> SEQUENCE: 21
aggcggttct aagagcagaa ccat                                              24

<210> SEQ ID NO 22
<211> LENGTH: 24
<212> TYPE: DNA
<213> ORGANISM: Artificial Sequence
<220> FEATURE:
<223> OTHER INFORMATION: EMCV 2A Reverse primer

<400> SEQUENCE: 22
agtgggcatt gaagatccgg taca                                              24

<210> SEQ ID NO 23
<211> LENGTH: 24
<212> TYPE: DNA
<213> ORGANISM: Artificial Sequence
<220> FEATURE:
<223> OTHER INFORMATION: EMCV VP3 Forward primer

<400> SEQUENCE: 23
ccatgcaggc gacttatgcg attt                                              24

<210> SEQ ID NO 24
<211> LENGTH: 24
<212> TYPE: DNA
<213> ORGANISM: Artificial Sequence
<220> FEATURE:
<223> OTHER INFORMATION: EMCV VP3 Reverse primer

<400> SEQUENCE: 24
taacccagcc atccgcatta gtga                                              24

<210> SEQ ID NO 25
<211> LENGTH: 24
<212> TYPE: DNA
<213> ORGANISM: Artificial Sequence
<220> FEATURE:
<223> OTHER INFORMATION: EMCV 5'UTR Forward primer

<400> SEQUENCE: 25
ttgaaagccg ggggtgggag atcc                                              24

<210> SEQ ID NO 26
<211> LENGTH: 23
<212> TYPE: DNA
<213> ORGANISM: Artificial Sequence
<220> FEATURE:
<223> OTHER INFORMATION: EMCV 5'UTR Reverse primer

<400> SEQUENCE: 26
gtttgttgtt gttttggggt ggc                                               23

<210> SEQ ID NO 27
<211> LENGTH: 20
<212> TYPE: DNA
<213> ORGANISM: Artificial Sequence
<220> FEATURE:
<223> OTHER INFORMATION: NoV Replicase Forward primer
```

<400> SEQUENCE: 27
ccgttcatgg cttacacctt                                          20

<210> SEQ ID NO 28
<211> LENGTH: 20
<212> TYPE: DNA
<213> ORGANISM: Artificial Sequence
<220> FEATURE:
<223> OTHER INFORMATION: NoV Replicase Reverse primer

<400> SEQUENCE: 28
gcaccagtcc caaacttcat                                          20

<210> SEQ ID NO 29
<211> LENGTH: 20
<212> TYPE: DNA
<213> ORGANISM: Artificial Sequence
<220> FEATURE:
<223> OTHER INFORMATION: NoV Capsid Forward primer

<400> SEQUENCE: 29
cagagaatgg cagcaacaaa                                          20

<210> SEQ ID NO 30
<211> LENGTH: 20
<212> TYPE: DNA
<213> ORGANISM: Artificial Sequence
<220> FEATURE:
<223> OTHER INFORMATION: NoV Capsid Reverse primer

<400> SEQUENCE: 30
cggtaaaacg agaccctgaa                                          20

<210> SEQ ID NO 31
<211> LENGTH: 20
<212> TYPE: DNA
<213> ORGANISM: Artificial Sequence
<220> FEATURE:
<223> OTHER INFORMATION: Rrm2 Forward primer

<400> SEQUENCE: 31
ccgagtcgga aagtaaagcg                                          20

<210> SEQ ID NO 32
<211> LENGTH: 20
<212> TYPE: DNA
<213> ORGANISM: Artificial Sequence
<220> FEATURE:
<223> OTHER INFORMATION: Rrm2 Reverse primer

<400> SEQUENCE: 32
atgggaaaga caacgaagcg                                          20

<210> SEQ ID NO 33
<211> LENGTH: 20
<212> TYPE: DNA
<213> ORGANISM: Artificial Sequence
<220> FEATURE:
<223> OTHER INFORMATION: Btg2 Forward primer

<400> SEQUENCE: 33
gcgagcagag actcaaggtt                                          20

<210> SEQ ID NO 34
<211> LENGTH: 20

```
<212> TYPE: DNA
<213> ORGANISM: Artificial Sequence
<220> FEATURE:
<223> OTHER INFORMATION: Btg2 Reverse primer

<400> SEQUENCE: 34
tagccagaac ctttggatgg                                           20

<210> SEQ ID NO 35
<211> LENGTH: 19
<212> TYPE: DNA
<213> ORGANISM: Artificial Sequence
<220> FEATURE:
<223> OTHER INFORMATION: Pou5f1 Forward primer

<400> SEQUENCE: 35
caactcccga ggagtccca                                            19

<210> SEQ ID NO 36
<211> LENGTH: 20
<212> TYPE: DNA
<213> ORGANISM: Artificial Sequence
<220> FEATURE:
<223> OTHER INFORMATION: Pou5f1 Reverse primer

<400> SEQUENCE: 36
ctgggtgtac cccaaggtga                                           20

<210> SEQ ID NO 37
<211> LENGTH: 26
<212> TYPE: DNA
<213> ORGANISM: Artificial Sequence
<220> FEATURE:
<223> OTHER INFORMATION: Nanog Reverse primer

<400> SEQUENCE: 37
cagaaaaacc agtggttgaa gactag                                    26

<210> SEQ ID NO 38
<211> LENGTH: 21
<212> TYPE: DNA
<213> ORGANISM: Artificial Sequence
<220> FEATURE:
<223> OTHER INFORMATION: Nanog Reverse primer

<400> SEQUENCE: 38
gcaatggatg ctgggatact c                                         21

<210> SEQ ID NO 39
<211> LENGTH: 20
<212> TYPE: DNA
<213> ORGANISM: Artificial Sequence
<220> FEATURE:
<223> OTHER INFORMATION: Fgf5 Forward primer

<400> SEQUENCE: 39
tgtactgcag agtgggcatc                                           20

<210> SEQ ID NO 40
<211> LENGTH: 20
<212> TYPE: DNA
<213> ORGANISM: Artificial Sequence
<220> FEATURE:
<223> OTHER INFORMATION: Fgf5 Reverse primer

<400> SEQUENCE: 40
```
acaatcccct gagacacagc                                              20

<210> SEQ ID NO 41

<400> SEQUENCE: 41

000

<210> SEQ ID NO 42
<211> LENGTH: 23
<212> TYPE: RNA
<213> ORGANISM: Artificial Sequence
<220> FEATURE:
<223> OTHER INFORMATION: miR-295

<400> SEQUENCE: 42
aaagugcuac uacuuugag ucu                                           23

<210> SEQ ID NO 43
<211> LENGTH: 22
<212> TYPE: RNA
<213> ORGANISM: Artificial Sequence
<220> FEATURE:
<223> OTHER INFORMATION: miR-21

<400> SEQUENCE: 43
uagcuuauca gacugauguu ga                                           22

<210> SEQ ID NO 44
<211> LENGTH: 21
<212> TYPE: DNA
<213> ORGANISM: Artificial Sequence
<220> FEATURE:
<223> OTHER INFORMATION: DICER 460 R

<400> SEQUENCE: 44
gtacgtctac aattgtctat g                                            21

<210> SEQ ID NO 45
<211> LENGTH: 24
<212> TYPE: DNA
<213> ORGANISM: Artificial Sequence
<220> FEATURE:
<223> OTHER INFORMATION: DICER 23 F

<400> SEQUENCE: 45
attgttacca gcgcttagaa ttcc                                         24

<210> SEQ ID NO 46
<211> LENGTH: 23
<212> TYPE: DNA
<213> ORGANISM: Artificial Sequence
<220> FEATURE:
<223> OTHER INFORMATION: DICER 458 F

<400> SEQUENCE: 46
tcggaatagg aacttcgtta aac                                          23

<210> SEQ ID NO 47
<211> LENGTH: 22
<212> TYPE: RNA
<213> ORGANISM: Artificial Sequence
<220> FEATURE:
<223> OTHER INFORMATION: RNA1 siRNA

<400> SEQUENCE: 47
ugaacuacga gacaaucauc aa                                      22

<210> SEQ ID NO 48
<211> LENGTH: 22
<212> TYPE: RNA
<213> ORGANISM: Artificial Sequence
<220> FEATURE:
<223> OTHER INFORMATION: RNA1 siRNA

<400> SEQUENCE: 48
cgacuugaug cucuguuagu ag                                      22

<210> SEQ ID NO 49
<211> LENGTH: 50
<212> TYPE: RNA
<213> ORGANISM: Artificial Sequence
<220> FEATURE:
<223> OTHER INFORMATION: RNA1 nucleic acid fragment

<400> SEQUENCE: 49
guauugaauc caaaacucaa aaugcugaac uacgagacaa ucaucaacgg         50

<210> SEQ ID NO 50
<211> LENGTH: 22
<212> TYPE: RNA
<213> ORGANISM: Artificial Sequence
<220> FEATURE:
<223> OTHER INFORMATION: RNA1 siRNA

<400> SEQUENCE: 50
uugaauccaa aacucaaaau gc                                      22

<210> SEQ ID NO 51
<211> LENGTH: 22
<212> TYPE: RNA
<213> ORGANISM: Artificial Sequence
<220> FEATURE:
<223> OTHER INFORMATION: RNA1 siRNA

<400> SEQUENCE: 51
auaacuuagg uuuugaguuu ua                                      22

<210> SEQ ID NO 52
<211> LENGTH: 43
<212> TYPE: DNA
<213> ORGANISM: Artificial Sequence
<220> FEATURE:
<223> OTHER INFORMATION: EMCV fragment

<400> SEQUENCE: 52
cggattgcca gtctgctcga tatcgcaggc tgggtccgtg act                43

<210> SEQ ID NO 53
<211> LENGTH: 44
<212> TYPE: DNA
<213> ORGANISM: Artificial Sequence
<220> FEATURE:
<223> OTHER INFORMATION: EMCV fragment

<400> SEQUENCE: 53
gtcacggacc cagcctgcga tatcgagcag actggcaatc cgga              44

<210> SEQ ID NO 54
<211> LENGTH: 92
<212> TYPE: DNA
<213> ORGANISM: Artificial Sequence

```
<220> FEATURE:
<223> OTHER INFORMATION: NoV RNA1 fragment

<400> SEQUENCE: 54
gtattgaatc caaaactcaa aatgctgaac tacgagacaa tcatcaacgg cgcatcgagc    60
gctctgaaca tcgtttcgcg tgcgttagga ta                                  92

<210> SEQ ID NO 55
<211> LENGTH: 92
<212> TYPE: DNA
<213> ORGANISM: Artificial Sequence
<220> FEATURE:
<223> OTHER INFORMATION: NoV RNA1 fragment

<400> SEQUENCE: 55
tatcctaacg cacgcgaaac gatgttcaga gcgctcgatg cgccgttgat gattgtctcg    60
tagttcagca ttttgagttt tggattcaat ac                                  92

<210> SEQ ID NO 56
<211> LENGTH: 90
<212> TYPE: DNA
<213> ORGANISM: Artificial Sequence
<220> FEATURE:
<223> OTHER INFORMATION: NoV RNA2 fragment

<400> SEQUENCE: 56
taccgcgtgc cactagccaa atcgctggcg ctggtcgcgg ggtcctgcgt ggtgtacaaa    60
ataatcgtgc atcgacgcac gctcgtggcg                                     90

<210> SEQ ID NO 57
<211> LENGTH: 90
<212> TYPE: DNA
<213> ORGANISM: Artificial Sequence
<220> FEATURE:
<223> OTHER INFORMATION: NoV RNA2 fragment

<400> SEQUENCE: 57
cgccacgagc gtgcgtcgat gcacgattat tttgtacacc acgcaggacc ccgcgaccag    60
cgccagcgat ttggctagtg gcacgcggta                                     90

<210> SEQ ID NO 58
<211> LENGTH: 22
<212> TYPE: DNA
<213> ORGANISM: Artificial Sequence
<220> FEATURE:
<223> OTHER INFORMATION: Positive strand siDuplex

<400> SEQUENCE: 58
cggattgcca gtctgctcga ta                                             22

<210> SEQ ID NO 59
<211> LENGTH: 22
<212> TYPE: DNA
<213> ORGANISM: Artificial Sequence
<220> FEATURE:
<223> OTHER INFORMATION: Negative Strand siDuplex

<400> SEQUENCE: 59
tcgagcagac tggcaatccg ga                                             22

<210> SEQ ID NO 60
<211> LENGTH: 33
<212> TYPE: RNA
```

```
<213> ORGANISM: Artificial Sequence
<220> FEATURE:
<223> OTHER INFORMATION: NoV subgenomic RNA3 fragment

<400> SEQUENCE: 60
guguauuuca gaaugacaaa caugucaugc gcu                                33

<210> SEQ ID NO 61
<211> LENGTH: 111
<212> TYPE: DNA
<213> ORGANISM: Artificial Sequence
<220> FEATURE:
<223> OTHER INFORMATION: EMCV positive fragment

<400> SEQUENCE: 61
ttgaaagccg ggggtgggag atccggattg ccagtctgct cgatatcgca ggctgggtcc    60
gtgactaccc actcccctt tcaacgtgaa ggctacgata gtgccagggc g              111

<210> SEQ ID NO 62
<211> LENGTH: 111
<212> TYPE: DNA
<213> ORGANISM: Artificial Sequence
<220> FEATURE:
<223> OTHER INFORMATION: EMCV negative strand fragment

<400> SEQUENCE: 62
cgccctggca ctatcgtagc cttcacgttg aaaggggag tgggtagtca cggacccagc     60
ctgcgatatc gagcagactg gcaatccgga tctcccaccc ccggctttca a             111
```